US012674198B2

(12) United States Patent
Chakraborty et al.

(10) Patent No.: US 12,674,198 B2
(45) Date of Patent: Jul. 7, 2026

(54) METHOD AND KIT FOR DETECTION OF POLYNUCLEOTIDE

(71) Applicant: Council of Scientific & Industrial Research, New Delhi (IN)

(72) Inventors: Debojyoti Chakraborty, Delhi (IN); Souvik Maiti, Delhi (IN); Mohammad Azhar, Delhi (IN); Rhythm Phutela, Delhi (IN); Namrata Sharma, Delhi (IN); Dipanjali Sinha, Delhi (IN); Saumya Sharma, Delhi (IN); Arpit Mishra, Delhi (IN); Asgar Hussain Ansari, Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 998 days.

(21) Appl. No.: 17/781,726

(22) PCT Filed: Dec. 1, 2020

(86) PCT No.: PCT/IN2020/050993
§ 371 (c)(1),
(2) Date: Jun. 2, 2022

(87) PCT Pub. No.: WO2021/111466
PCT Pub. Date: Jun. 10, 2021

(65) Prior Publication Data

US 2023/0031670 A1 Feb. 2, 2023

(30) Foreign Application Priority Data

Dec. 2, 2019 (IN) ............................ 201911049432
Mar. 27, 2020 (IN) ............................ 202011013418

(51) Int. Cl.

*C07K 14/195* (2006.01)
*C12Q 1/686* (2018.01)
*C12Q 1/6883* (2018.01)
*C12Q 1/70* (2006.01)

(52) U.S. Cl.
CPC ............ *C12Q 1/686* (2013.01); *C07K 14/195* (2013.01); *C12Q 1/6883* (2013.01); *C12Q 1/701* (2013.01)

(58) Field of Classification Search
None
See application file for complete search history.

(56) References Cited

FOREIGN PATENT DOCUMENTS

| | | | | |
|---|---|---|---|---|
| CN | 1453363 | * | 11/2011 | |
| CN | 105420233 | * | 3/2016 | |
| KR | 20170063399 A | | 6/2017 | |
| WO | WO-2008032205 A2 | * | 3/2008 | ........... C12Q 1/6834 |
| WO | WO 2014018423 A2 | | 1/2014 | |
| WO | WO 2014093595 | | 6/2014 | |
| WO | WO-2016057961 A1 | * | 4/2016 | ........... C12N 15/625 |
| WO | WO 2017091630 | | 6/2017 | |
| WO | WO 2018107129 | | 6/2018 | |
| WO | WO-2019126577 A2 | * | 6/2019 | ........... C12Q 1/6876 |

OTHER PUBLICATIONS

Hirano, H., Gootenberg, J.S., Horii, T., Abudayyeh, O.O., Kimura, M., Hsu, P.D., Nakane, T., Ishitani, R., Hatada, I., Zhang, F. and Nishimasu, H., 2016. Structure and engineering of Francisella novicida Cas9. Cell, 164(5), pp. 950-961. (Year: 2016).*
Ahern H., The Scientist (Jul. 24 1995) p. 5 (Year: 1995).*
Zhao, Yongxi et al., Isothermal Amplification of Nucleic Acids, Chemical Reviews, © 2015 American Chemical Society, ACS Publications, Chem. Rev. 2015, 115, 12491-12545.
Ribeiro, Marcel L. et al, Annals of Clinical Microbiology and Antimicrobials 2003, 2:11, pp. 1-4, http://www.ann-clinmicrob.com/content/2/1/11.
Andrieu-Soler et al., When basic science reaches into rational therapeutic design: from historical to novel leads for the treatment of β-globinopathies, pp. 141-148, Current Pinion, Copyright © 2020 Wolters Kluwer Health, Inc., www.co-hematology.com.
Azhar, Modh et al., Rapid and accurate nucleobase detection using FnCas9 and its application in COVID-19 diagnois, pp. 1-8, Biosensors and Bioelectronics 183 (2021) 113207, Published by Elsevier B.V.
Biesecker, Leslie G., M.D.et al., Diagnostic Clinical Genome and Exome Sequencing, The New England Journal of Medicine, 2418-2425, N Engl J Med 370;25, Jun. 19, 2014.
Dong De et al., The crystal structure of Cph1 in complex with CRISPR RNA, pp. 1-16, 00 Month 2026, vol. 000, Nature, © 2016 Macmillan Publishers Limited.

(Continued)

*Primary Examiner* — Heather Calamita
(74) *Attorney, Agent, or Firm* — Blank Rome LLP

(57) ABSTRACT

The invention describes a kit for detection of a target polynucleotide using a CRISPR effector system that comprises CAS9 from *Francisella novicida*, a synthetic sgRNA and a detection scheme based on binding and subsequent enzymatic cleavage of the target polynucleotide. The invention also describes a method for detection of a target polynucleotide using the kit. The kit can be applied to both pathogenic and non-pathogenic polynucleotides and can be used to distinguish polynucleotides different by a single mismatch without the need for sequencing. The kit can also be used for detection of COVID-19. The kit is economical, easy to assemble and provides a robust and rapid readout that can be appropriately adapted for point of care applications.

16 Claims, 27 Drawing Sheets

Specification includes a Sequence Listing.

(56) References Cited

OTHER PUBLICATIONS

Binkowska, Aldona et al., Molecular Patterns of Resistance Among Helicobacter pylori Strains in South-Western Poland, Frontiers in Microbiology, pp. 1-10, Dec. 2018, vol. 9, Article 3154.
Landrum, Melissa J. et al., ClinVar: public archive of relationships among sequence variation and human phenotype, pp. D980-D985, Nucleic Acids Research, 2014, vol. 42, Database issue, published Sep. 13, 2013.
Hsu, Patrick D. et al., DNA targeting specificity of RNA-guided Cas9 nucleases, pp. 827-834, Nature Biotechnology, vol. 31, No. 9, Sep. 2013.
Jinek, Martin et al., A Programmable Dual-RNA-Guided DNA Endonuclease in Adaptive Bacterial Immunity, Research Article, pp. 816-821, Aug. 17, 2012, vol. 337, Science.
Yi, Li et al., Crisper/Cas Systems towards Next-Generation Biosensing, CellPress Reviews, pp. 730-743, Trends in Biotechnology, Jul. 2019, vol. 37, No., © 2019 Elsevier Ltd.
Lobato, Ivan Magriñá et al., Recombinase Polymersase Amplification: Basics, applications and recent advances, Accepted Manuscript, to appear in Trends in Analytical Chemistry, (2017), doi: 10.1016/j.trac.2017.10.015.
Mojica, Francisco J.M. et al., Intervening Sequences of Regularly Spaced Prokaryotic Repeats Derive from Foreign Genetic Elements, Accepted Oct. 1, 2004, pp. 174-182, Journal of Molecular Evolution, © Springer Science+Business Media, Inc. 20025, J Mol Evol (2005) 60: 174-182, DOI: 10.1007/s00239-004-0046-3.
Nayak, Samiksha et al., Point-of-Care Diagnostics: Recent Developments in a Connected Age., Analytical Chemistry, Special Issue: Fundamental and Applied Reviews in Analytical Chemistry 2017.
Piel, Frèdèric et al., Sickle Cell Disease, The New England Journal of Medicine, pp. 1561-1573, N Engl J Med 376;16, Apr. 20, 2027, copyright © 2017 Massachusetts Medical Society.
Beware of the second wave of COVID-19, Published Online Apr. 8, 2020, https:/doi.org/10.1016/S0140-6736(20) 30845-X, www.thelancet.com, vol. 395, Apr. 25, 2020, pp. 1321-1322.
Terns, Michael P., Crisper-Based Technologies: Impact of RNA-Targeting Systems, Molecular Cell, pp. 404-412, Molecular Cell 72, Nov. 1, 2018 © 2018 Elsevier Inc.
Wienken, Christoph J. et al, Protein-binding assays in biological liquids using microscale thermophoresis, Article, published Oct. 19, 2010, Nature Communications, DOI: 10.1038/ncomms1093, www.nature.com/naturecommunications, © 2010 Macillan Publishers Limited.

* cited by examiner

SEQ ID NO: 1

SEQ ID NO: 3

$K_d$=53.8nM±25.9nM

WT sgRNA: SEQ ID NO: 31 sgRNA_2_6 : SEQ ID NO: 32

Mismatched target_1 : SEQ ID NO: 33

Mismatched target_2 : SEQ ID NO: 34

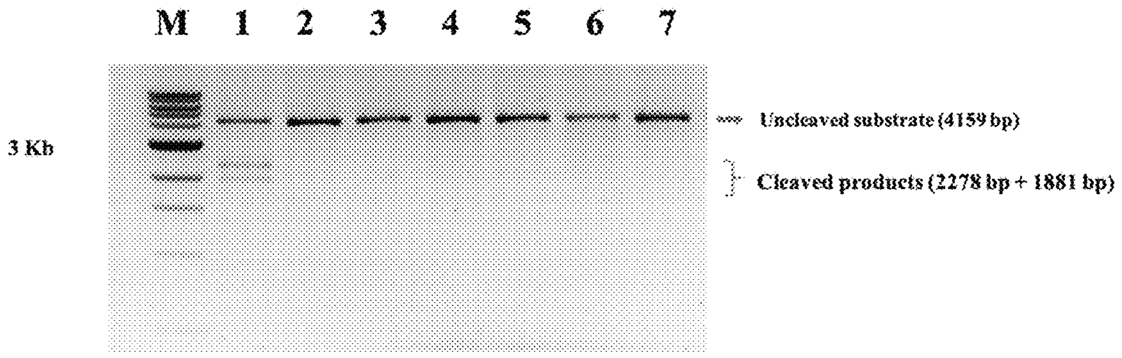

Fig. 13

Detection of the SCD and Heterozygous 410bp PCR amplicon by the IVC assay(400nM FnCas9:800nM sgRNA)

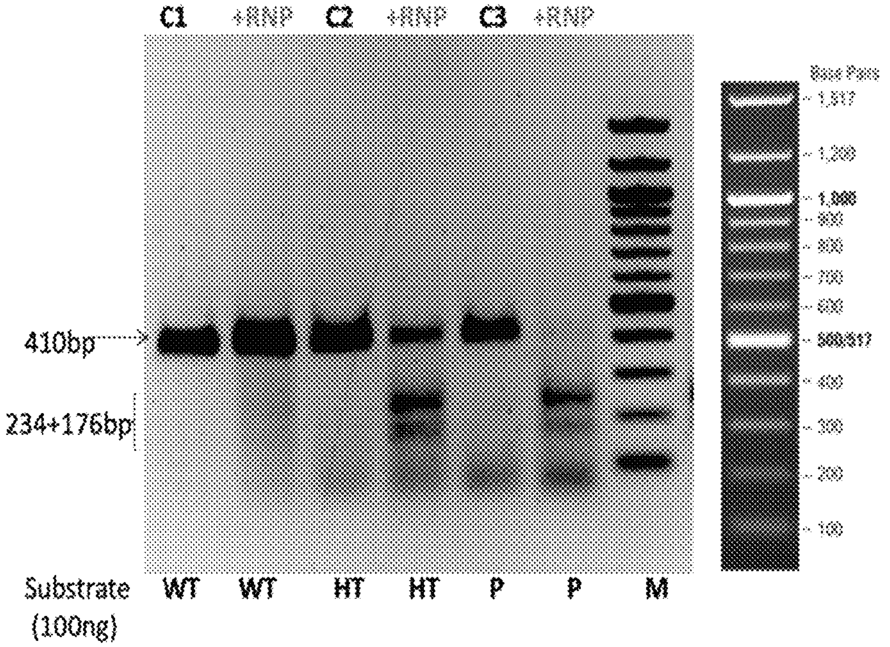

Wild Type DNA sequence PAM 5'- GAGGAGAAGTCTGCCGTTAC -3' (SEQ ID NO: 81)
Hbb(2&6) sgRNA PAM 3'- CACCTATTCAGACGGCAATG- 5 (2MM with WT type and 1MM for patient) (SEQ ID NO: 82)
SCD sequence PAM 5'- GTGGAGAAGTCTGCCGTTAC- 3' (SEQ ID NO: 83)

In Heterozygous condition approximately 50% of cleavage is observed as compared to the WT(NO CLEAVAGE) and the SCD(COMPLETE CLEAVAGE) when incubated with Hbb(2&6) sgRNA

Fig. 14

| FELUDA (2 gene) | qPCR Pos | qPCR Neg | qPCR Total |
|---|---|---|---|
| Pos | 21 | 2 | 23 |
| Neg | 0 | 58 | 58 |
| Total | 21 | 60 | |
| | Sens. 100 | Spec. 96.7 | |

Row 1 – SEQ ID NO: 19
Row 2 – SEQ ID NO: 20
Row 3 – SEQ ID NO: 21
Row 4 – SEQ ID NO: 22
Row 5 – SEQ ID NO: 23
Row 6 – SEQ ID NO: 24
Row 7 – SEQ ID NO: 25
Row 8 – SEQ ID NO: 26
Row 9 – SEQ ID NO: 27
Row 10 – SEQ ID NO: 28
Row 11 – SEQ ID NO: 29
Row 12 – SEQ ID NO: 30
Row 13 – SEQ ID NO: 31

1. WT Glanzmann's Thrombasthenia 2. mut Glanzmann's Thrombasthenia

3. WT Hemophilia A (Factor VIII deficiency)

4. mut Hemophilia A (Factor VIII deficiency)

5. WT Glycogen Storage Disease Type I 6. mut Glycogen Storage Disease Type I

7. WT X- linked myotubular myopathy 8. mut X- linked myotubular myopathy

GTGGAGAAGTCTGCCGTTAC
CACCTXTTCAGACGGCAATG (SEQ ID NO: 84)

WT strain
GACGGAAAGACCCCGTGGAC   (SEQ ID NO: 85)

A2142G strain
GACGGGAAGACCCCGTGGAC   (SEQ ID NO: 86)

A2143G strain
GACGGAGAGACCCCGTGGAC   (SEQ ID NO: 87)

A2142G sgRNA

GTCCACGGGGTCTTCCCGGC   (SEQ ID NO: 88)

A2143G sgRNA

GTCCACGGGGTCTCTCCGGC   (SEQ ID NO: 89)

Mismatches away from PAM

M   -RNP   0   16   17   18   19

Uncut   6.3 kb
Cut   3.7 kb
       2.6 kb

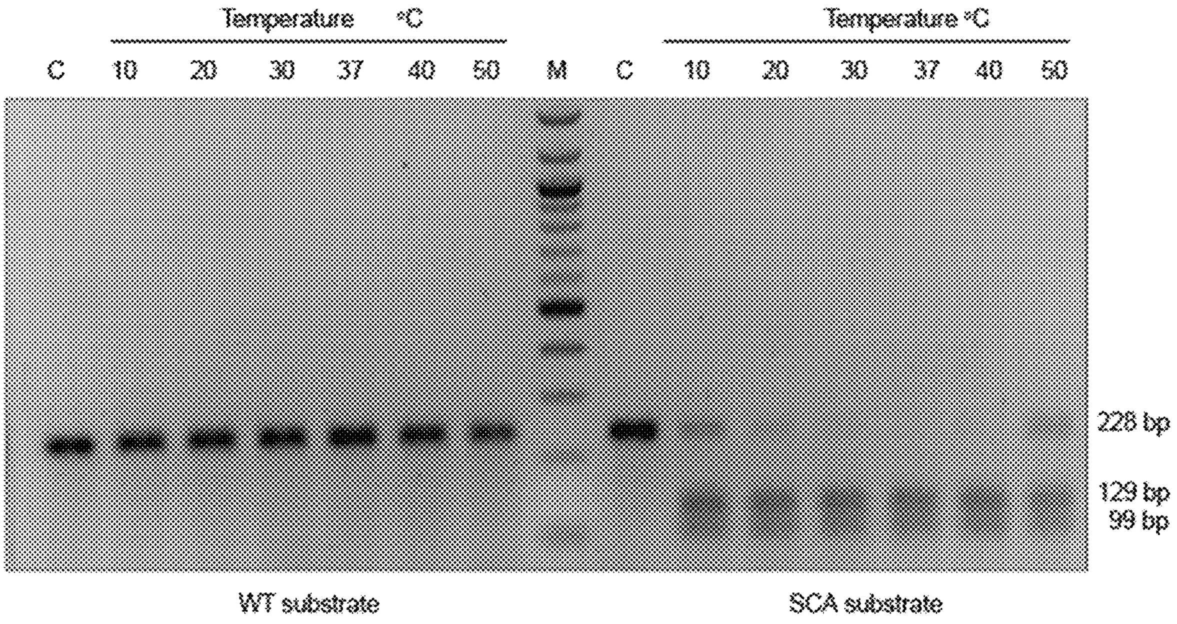

Fig. 41

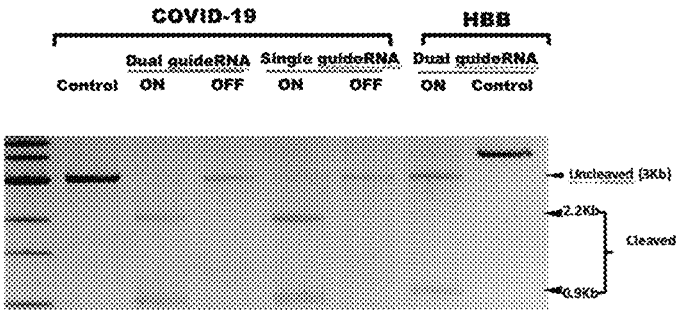

COVID-19-
Uncleaved (3kb)
Cleaved ( 2.1kb and 0.9kb)

HBB-
Uncleaved (4.1kb)
Cleaved ( 3kb and 1.1kb)

Control- Only substrate without RNP

ON- On target for the crRNA/sgRNA.

OFF- Off target for the crRNA/sgRNA.

Dual guideRNA (Chimeric gRNA)- crRNA:TracrRNA annealed complex

Single guideRNA- 19 nucleotide sgRNA starting with " G".

COVID-19- target and Off target cloned in pJET vector (3kb).

HBB- Hbb locus cloned in TOPO vector (4.1 kb)

Fig. 42

SEQUENCE LISTING

<160> NUMBER OF SEQ ID NOS: 93

<210> SEQ ID NO 1
<211> LENGTH: 1629
<212> TYPE: PRT

```
<213> ORGANISM: Francisella novicida

<400> SEQUENCE: 1

Met Asn Phe Lys Ile Leu Pro Ile Ala Ile Asp Leu Gly Val Lys Asn
1               5                   10                  15

Thr Gly Val Phe Ser Ala Phe Tyr Gln Lys Gly Thr Ser Leu Glu Arg
            20                  25                  30

Leu Asp Asn Lys Asn Gly Lys Val Tyr Glu Leu Ser Lys Asp Ser Tyr
        35                  40                  45

Thr Leu Leu Met Asn Asn Arg Thr Ala Arg Arg His Gln Arg Arg Gly
    50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Pro Glu Tyr Leu Asn Ile Val Pro Glu Gln Val Lys Ala Ile Leu Met
        115                 120                 125

Asp Ile Phe Asp Asp Tyr Asn Gly Glu Asp Asp Leu Asp Ser Tyr Leu
    130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Met Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
        195                 200                 205

Leu Lys Thr Gln Lys Phe Ser Tyr Thr Asp Lys Gln Gly Asn Leu Lys
    210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Arg Ile Leu Asp Thr Leu Leu Thr
                245                 250                 255

Asp Asp Leu Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Ile Gln
        275                 280                 285

Ala His Leu His His Phe Val Phe Ala Val Asn Lys Ile Lys Ser Glu
    290                 295                 300

Met Ala Ser Gly Gly Arg His Arg Ser Gln Tyr Phe Gln Glu Ile Thr
305                 310                 315                 320

Asn Val Leu Asp Glu Asn Asn His Gln Glu Gly Tyr Leu Lys Asn Phe
                325                 330                 335

Cys Glu Asn Leu His Asn Lys Lys Tyr Ser Asn Leu Ser Val Lys Asn
            340                 345                 350

Leu Val Asn Leu Ile Gly Asn Leu Ser Asn Leu Glu Leu Lys Pro Leu
        355                 360                 365

Arg Lys Tyr Phe Asn Asp Lys Ile His Ala Lys Ala Asp His Trp Asp
    370                 375                 380

Glu Gln Lys Phe Thr Glu Thr Tyr Cys His Trp Ile Leu Gly Glu Trp
385                 390                 395                 400
```

-continued

```
Arg Val Gly Val Lys Asp Gln Asp Lys Lys Asp Gly Ala Lys Tyr Ser
                405                 410                 415

Tyr Lys Asp Leu Cys Asn Glu Leu Lys Gln Lys Val Thr Lys Ala Gly
            420                 425                 430

Leu Val Asp Phe Leu Leu Glu Leu Asp Pro Cys Arg Thr Ile Pro Pro
        435                 440                 445

Tyr Leu Asp Asn Asn Asn Arg Lys Pro Pro Lys Cys Gln Ser Leu Ile
    450                 455                 460

Leu Asn Pro Lys Phe Leu Asp Asn Gln Tyr Pro Asn Trp Gln Gln Tyr
465                 470                 475                 480

Leu Gln Glu Leu Lys Lys Leu Gln Ser Ile Gln Asn Tyr Leu Asp Ser
                485                 490                 495

Phe Glu Thr Asp Leu Lys Val Leu Lys Ser Ser Lys Asp Gln Pro Tyr
            500                 505                 510

Phe Val Glu Tyr Lys Ser Ser Asn Gln Gln Ile Ala Ser Gly Gln Arg
        515                 520                 525

Asp Tyr Lys Asp Leu Asp Ala Arg Ile Leu Gln Phe Ile Phe Asp Arg
    530                 535                 540

Val Lys Ala Ser Asp Glu Leu Leu Leu Asn Glu Ile Tyr Phe Gln Ala
545                 550                 555                 560

Lys Lys Leu Lys Gln Lys Ala Ser Ser Glu Leu Glu Lys Leu Glu Ser
                565                 570                 575

Ser Lys Lys Leu Asp Glu Val Ile Ala Asn Ser Gln Leu Ser Gln Ile
            580                 585                 590

Leu Lys Ser Gln His Thr Asn Gly Ile Phe Glu Gln Gly Thr Phe Leu
        595                 600                 605

His Leu Val Cys Lys Tyr Tyr Lys Gln Arg Gln Arg Ala Arg Asp Ser
    610                 615                 620

Arg Leu Tyr Ile Met Pro Glu Tyr Arg Tyr Asp Lys Lys Leu His Lys
625                 630                 635                 640

Tyr Asn Asn Thr Gly Arg Phe Asp Asp Asp Asn Gln Leu Leu Thr Tyr
                645                 650                 655

Cys Asn His Lys Pro Arg Gln Lys Arg Tyr Gln Leu Leu Asn Asp Leu
            660                 665                 670

Ala Gly Val Leu Gln Val Ser Pro Asn Phe Leu Lys Asp Lys Ile Gly
        675                 680                 685

Ser Asp Asp Asp Leu Phe Ile Ser Lys Trp Leu Val Glu His Ile Arg
    690                 695                 700

Gly Phe Lys Lys Ala Cys Glu Asp Ser Leu Lys Ile Gln Lys Asp Asn
705                 710                 715                 720

Arg Gly Leu Leu Asn His Lys Ile Asn Ile Ala Arg Asn Thr Lys Gly
                725                 730                 735

Lys Cys Glu Lys Glu Ile Phe Asn Leu Ile Cys Lys Ile Glu Gly Ser
            740                 745                 750

Glu Asp Lys Lys Gly Asn Tyr Lys His Gly Leu Ala Tyr Glu Leu Gly
        755                 760                 765

Val Leu Leu Phe Gly Glu Pro Asn Glu Ala Ser Lys Pro Glu Phe Asp
    770                 775                 780

Arg Lys Ile Lys Lys Phe Asn Ser Ile Tyr Ser Phe Ala Gln Ile Gln
785                 790                 795                 800

Gln Ile Ala Phe Ala Glu Arg Lys Gly Asn Ala Asn Thr Cys Ala Val
                805                 810                 815

Cys Ser Ala Asp Asn Ala His Arg Met Gln Gln Ile Lys Ile Thr Glu
```

-continued

```
            820                 825                 830

Pro Val Glu Asp Asn Lys Asp Lys Ile Ile Leu Ser Ala Lys Ala Gln
        835                 840                 845

Arg Leu Pro Ala Ile Pro Thr Arg Ile Val Asp Gly Ala Val Lys Lys
    850                 855                 860

Met Ala Thr Ile Leu Ala Lys Asn Ile Val Asp Asp Asn Trp Gln Asn
865                 870                 875                 880

Ile Lys Gln Val Leu Ser Ala Lys His Gln Leu His Ile Pro Ile Ile
                885                 890                 895

Thr Glu Ser Asn Ala Phe Glu Phe Glu Pro Ala Leu Ala Asp Val Lys
            900                 905                 910

Gly Lys Ser Leu Lys Asp Arg Arg Lys Lys Ala Leu Glu Arg Ile Ser
        915                 920                 925

Pro Glu Asn Ile Phe Lys Asp Lys Asn Asn Arg Ile Lys Glu Phe Ala
    930                 935                 940

Lys Gly Ile Ser Ala Tyr Ser Gly Ala Asn Leu Thr Asp Gly Asp Phe
945                 950                 955                 960

Asp Gly Ala Lys Glu Glu Leu Asp His Ile Ile Pro Arg Ser His Lys
                965                 970                 975

Lys Tyr Gly Thr Leu Asn Asp Glu Ala Asn Leu Ile Cys Val Thr Arg
            980                 985                 990

Gly Asp Asn Lys Asn Lys Gly Asn  Arg Ile Phe Cys Leu  Arg Asp Leu
        995                 1000                1005

Ala Asp  Asn Tyr Lys Leu Lys  Gln Phe Glu Thr Thr  Asp Asp Leu
    1010                 1015                 1020

Glu Ile  Glu Lys Lys Ile Ala  Asp Thr Ile Trp Asp  Ala Asn Lys
    1025                 1030                 1035

Lys Asp  Phe Lys Phe Gly Asn  Tyr Arg Ser Phe Ile  Asn Leu Thr
    1040                 1045                 1050

Pro Gln  Glu Gln Lys Ala Phe  Arg His Ala Leu Phe  Leu Ala Asp
    1055                 1060                 1065

Glu Asn  Pro Ile Lys Gln Ala  Val Ile Arg Ala Ile  Asn Asn Arg
    1070                 1075                 1080

Asn Arg  Thr Phe Val Asn Gly  Thr Gln Arg Tyr Phe  Ala Glu Val
    1085                 1090                 1095

Leu Ala  Asn Asn Ile Tyr Leu  Arg Ala Lys Lys Glu  Asn Leu Asn
    1100                 1105                 1110

Thr Asp  Lys Ile Ser Phe Asp  Tyr Phe Gly Ile Pro  Thr Ile Gly
    1115                 1120                 1125

Asn Gly  Arg Gly Ile Ala Glu  Ile Arg Gln Leu Tyr  Glu Lys Val
    1130                 1135                 1140

Asp Ser  Asp Ile Gln Ala Tyr  Ala Lys Gly Asp Lys  Pro Gln Ala
    1145                 1150                 1155

Ser Tyr  Ser His Leu Ile Asp  Ala Met Leu Ala Phe  Cys Ile Ala
    1160                 1165                 1170

Ala Asp  Glu His Arg Asn Asp  Gly Ser Ile Gly Leu  Glu Ile Asp
    1175                 1180                 1185

Lys Asn  Tyr Ser Leu Tyr Pro  Leu Asp Lys Asn Thr  Gly Glu Val
    1190                 1195                 1200

Phe Thr  Lys Asp Ile Phe Ser  Gln Ile Lys Ile Thr  Asp Asn Glu
    1205                 1210                 1215

Phe Ser  Asp Lys Lys Leu Val  Arg Lys Lys Ala Ile  Glu Gly Phe
    1220                 1225                 1230
```

-continued

```
Asn Thr  His Arg Gln Met Thr  Arg Asp Gly Ile Tyr  Ala Glu Asn
    1235                 1240                 1245

Tyr Leu  Pro Ile Leu Ile His  Lys Glu Leu Asn Glu  Val Arg Lys
    1250                 1255                 1260

Gly Tyr  Thr Trp Lys Asn Ser  Glu Glu Ile Lys Ile  Phe Lys Gly
    1265                 1270                 1275

Lys Lys  Tyr Asp Ile Gln Gln  Leu Asn Asn Leu Val  Tyr Cys Leu
    1280                 1285                 1290

Lys Phe  Val Asp Lys Pro Ile  Ser Ile Asp Ile Gln  Ile Ser Thr
    1295                 1300                 1305

Leu Glu  Glu Leu Arg Asn Ile  Leu Thr Thr Asn Asn  Ile Ala Ala
    1310                 1315                 1320

Thr Ala  Glu Tyr Tyr Tyr Ile  Asn Leu Lys Thr Gln  Lys Leu His
    1325                 1330                 1335

Glu Tyr  Tyr Ile Glu Asn Tyr  Asn Thr Ala Leu Gly  Tyr Lys Lys
    1340                 1345                 1350

Tyr Ser  Lys Glu Met Glu Phe  Leu Arg Ser Leu Ala  Tyr Arg Ser
    1355                 1360                 1365

Glu Arg  Val Lys Ile Lys Ser  Ile Asp Asp Val Lys  Gln Val Leu
    1370                 1375                 1380

Asp Lys  Asp Ser Asn Phe Ile  Ile Gly Lys Ile Thr  Leu Pro Phe
    1385                 1390                 1395

Lys Lys  Glu Trp Gln Arg Leu  Tyr Arg Glu Trp Gln  Asn Thr Thr
    1400                 1405                 1410

Ile Lys  Asp Asp Tyr Glu Phe  Leu Lys Ser Phe Phe  Asn Val Lys
    1415                 1420                 1425

Ser Ile  Thr Lys Leu His Lys  Lys Val Arg Lys Asp  Phe Ser Leu
    1430                 1435                 1440

Pro Ile  Ser Thr Asn Glu Gly  Lys Phe Leu Val Lys  Arg Lys Thr
    1445                 1450                 1455

Trp Asp  Asn Asn Phe Ile Tyr  Gln Ile Leu Asn Asp  Ser Asp Ser
    1460                 1465                 1470

Arg Ala  Asp Gly Thr Lys Pro  Phe Ile Pro Ala Phe  Asp Ile Ser
    1475                 1480                 1485

Lys Asn  Glu Ile Val Glu Ala  Ile Ile Asp Ser Phe  Thr Ser Lys
    1490                 1495                 1500

Asn Ile  Phe Trp Leu Pro Lys  Asn Ile Glu Leu Gln  Lys Val Asp
    1505                 1510                 1515

Asn Lys  Asn Ile Phe Ala Ile  Asp Thr Ser Lys Trp  Phe Glu Val
    1520                 1525                 1530

Glu Thr  Pro Ser Asp Leu Arg  Asp Ile Gly Ile Ala  Thr Ile Gln
    1535                 1540                 1545

Tyr Lys  Ile Asp Asn Asn Ser  Arg Pro Lys Val Arg  Val Lys Leu
    1550                 1555                 1560

Asp Tyr  Val Ile Asp Asp Asp  Ser Lys Ile Asn Tyr  Phe Met Asn
    1565                 1570                 1575

His Ser  Leu Leu Lys Ser Arg  Tyr Pro Asp Lys Val  Leu Glu Ile
    1580                 1585                 1590

Leu Lys  Gln Ser Thr Ile Ile  Glu Phe Glu Ser Ser  Gly Phe Asn
    1595                 1600                 1605

Lys Thr  Ile Lys Glu Met Leu  Gly Met Lys Leu Ala  Gly Ile Tyr
    1610                 1615                 1620
```

-continued

```
Asn Glu  Thr Ser Asn Asn
    1625


<210> SEQ ID NO 2
<211> LENGTH: 1629
<212> TYPE: PRT
<213> ORGANISM: Artificial Sequence
<220> FEATURE:
<223> OTHER INFORMATION: Protein sequence of recombinant dFnCas9 from
      Francisella novicida

<400> SEQUENCE: 2

Met Asn Phe Lys Ile Leu Pro Ile Ala Ile Ala Leu Gly Val Lys Asn
1               5                   10                  15

Thr Gly Val Phe Ser Ala Phe Tyr Gln Lys Gly Thr Ser Leu Glu Arg
            20                  25                  30

Leu Asp Asn Lys Asn Gly Lys Val Tyr Glu Leu Ser Lys Asp Ser Tyr
        35                  40                  45

Thr Leu Leu Met Asn Asn Arg Thr Ala Arg Arg His Gln Arg Arg Gly
    50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Pro Glu Tyr Leu Asn Ile Val Pro Glu Gln Val Lys Ala Ile Leu Met
        115                 120                 125

Asp Ile Phe Asp Asp Tyr Asn Gly Glu Asp Asp Leu Asp Ser Tyr Leu
    130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Met Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
        195                 200                 205

Leu Lys Thr Gln Lys Phe Ser Tyr Thr Asp Lys Gln Gly Asn Leu Lys
    210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Arg Ile Leu Asp Thr Leu Leu Thr
                245                 250                 255

Asp Asp Leu Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Ile Gln
        275                 280                 285

Ala His Leu His His Phe Val Phe Ala Val Asn Lys Ile Lys Ser Glu
    290                 295                 300

Met Ala Ser Gly Gly Arg His Arg Ser Gln Tyr Phe Gln Glu Ile Thr
305                 310                 315                 320

Asn Val Leu Asp Glu Asn Asn His Gln Glu Gly Tyr Leu Lys Asn Phe
                325                 330                 335

Cys Glu Asn Leu His Asn Lys Lys Tyr Ser Asn Leu Ser Val Lys Asn
            340                 345                 350
```

-continued

```
Leu Val Asn Leu Ile Gly Asn Leu Ser Asn Leu Glu Leu Lys Pro Leu
        355                 360                 365

Arg Lys Tyr Phe Asn Asp Lys Ile His Ala Lys Ala Asp His Trp Asp
    370                 375                 380

Glu Gln Lys Phe Thr Glu Thr Tyr Cys His Trp Ile Leu Gly Glu Trp
385                 390                 395                 400

Arg Val Gly Val Lys Asp Gln Asp Lys Lys Asp Gly Ala Lys Tyr Ser
                405                 410                 415

Tyr Lys Asp Leu Cys Asn Glu Leu Lys Gln Lys Val Thr Lys Ala Gly
            420                 425                 430

Leu Val Asp Phe Leu Leu Glu Leu Asp Pro Cys Arg Thr Ile Pro Pro
        435                 440                 445

Tyr Leu Asp Asn Asn Asn Arg Lys Pro Pro Lys Cys Gln Ser Leu Ile
    450                 455                 460

Leu Asn Pro Lys Phe Leu Asp Asn Gln Tyr Pro Asn Trp Gln Gln Tyr
465                 470                 475                 480

Leu Gln Glu Leu Lys Lys Leu Gln Ser Ile Gln Asn Tyr Leu Asp Ser
                485                 490                 495

Phe Glu Thr Asp Leu Lys Val Leu Lys Ser Ser Lys Asp Gln Pro Tyr
            500                 505                 510

Phe Val Glu Tyr Lys Ser Ser Asn Gln Gln Ile Ala Ser Gly Gln Arg
        515                 520                 525

Asp Tyr Lys Asp Leu Asp Ala Arg Ile Leu Gln Phe Ile Phe Asp Arg
    530                 535                 540

Val Lys Ala Ser Asp Glu Leu Leu Leu Asn Glu Ile Tyr Phe Gln Ala
545                 550                 555                 560

Lys Lys Leu Lys Gln Lys Ala Ser Ser Glu Leu Glu Lys Leu Glu Ser
                565                 570                 575

Ser Lys Lys Leu Asp Glu Val Ile Ala Asn Ser Gln Leu Ser Gln Ile
            580                 585                 590

Leu Lys Ser Gln His Thr Asn Gly Ile Phe Glu Gln Gly Thr Phe Leu
        595                 600                 605

His Leu Val Cys Lys Tyr Tyr Lys Gln Arg Gln Arg Ala Arg Asp Ser
    610                 615                 620

Arg Leu Tyr Ile Met Pro Glu Tyr Arg Tyr Asp Lys Lys Leu His Lys
625                 630                 635                 640

Tyr Asn Asn Thr Gly Arg Phe Asp Asp Asp Asn Gln Leu Leu Thr Tyr
                645                 650                 655

Cys Asn His Lys Pro Arg Gln Lys Arg Tyr Gln Leu Leu Asn Asp Leu
            660                 665                 670

Ala Gly Val Leu Gln Val Ser Pro Asn Phe Leu Lys Asp Lys Ile Gly
        675                 680                 685

Ser Asp Asp Asp Leu Phe Ile Ser Lys Trp Leu Val Glu His Ile Arg
    690                 695                 700

Gly Phe Lys Lys Ala Cys Glu Asp Ser Leu Lys Ile Gln Lys Asp Asn
705                 710                 715                 720

Arg Gly Leu Leu Asn His Lys Ile Asn Ile Ala Arg Asn Thr Lys Gly
                725                 730                 735

Lys Cys Glu Lys Glu Ile Phe Asn Leu Ile Cys Lys Ile Glu Gly Ser
            740                 745                 750

Glu Asp Lys Lys Gly Asn Tyr Lys His Gly Leu Ala Tyr Glu Leu Gly
        755                 760                 765
```

-continued

```
Val Leu Leu Phe Gly Glu Pro Asn Glu Ala Ser Lys Pro Glu Phe Asp
    770                 775                 780

Arg Lys Ile Lys Lys Phe Asn Ser Ile Tyr Ser Phe Ala Gln Ile Gln
785                 790                 795                 800

Gln Ile Ala Phe Ala Glu Arg Lys Gly Asn Ala Asn Thr Cys Ala Val
                805                 810                 815

Cys Ser Ala Asp Asn Ala His Arg Met Gln Gln Ile Lys Ile Thr Glu
            820                 825                 830

Pro Val Glu Asp Asn Lys Asp Lys Ile Ile Leu Ser Ala Lys Ala Gln
        835                 840                 845

Arg Leu Pro Ala Ile Pro Thr Arg Ile Val Asp Gly Ala Val Lys Lys
    850                 855                 860

Met Ala Thr Ile Leu Ala Lys Asn Ile Val Asp Asp Asn Trp Gln Asn
865                 870                 875                 880

Ile Lys Gln Val Leu Ser Ala Lys His Gln Leu His Ile Pro Ile Ile
                885                 890                 895

Thr Glu Ser Asn Ala Phe Glu Phe Glu Pro Ala Leu Ala Asp Val Lys
            900                 905                 910

Gly Lys Ser Leu Lys Asp Arg Arg Lys Lys Ala Leu Glu Arg Ile Ser
        915                 920                 925

Pro Glu Asn Ile Phe Lys Asp Lys Asn Asn Arg Ile Lys Glu Phe Ala
    930                 935                 940

Lys Gly Ile Ser Ala Tyr Ser Gly Ala Asn Leu Thr Asp Gly Asp Phe
945                 950                 955                 960

Asp Gly Ala Lys Glu Glu Leu Asp Ala Ile Ile Pro Arg Ser His Lys
                965                 970                 975

Lys Tyr Gly Thr Leu Asn Asp Glu Ala Asn Leu Ile Cys Val Thr Arg
            980                 985                 990

Gly Asp Asn Lys Asn Lys Gly Asn  Arg Ile Phe Cys Leu  Arg Asp Leu
        995                 1000                1005

Ala Asp  Asn Tyr Lys Leu Lys  Gln Phe Glu Thr Thr  Asp Asp Leu
    1010                1015                1020

Glu Ile  Glu Lys Lys Ile Ala  Asp Thr Ile Trp Asp  Ala Asn Lys
    1025                1030                1035

Lys Asp  Phe Lys Phe Gly Asn  Tyr Arg Ser Phe Ile  Asn Leu Thr
    1040                1045                1050

Pro Gln  Glu Gln Lys Ala Phe  Arg His Ala Leu Phe  Leu Ala Asp
    1055                1060                1065

Glu Asn  Pro Ile Lys Gln Ala  Val Ile Arg Ala Ile  Asn Asn Arg
    1070                1075                1080

Asn Arg  Thr Phe Val Asn Gly  Thr Gln Arg Tyr Phe  Ala Glu Val
    1085                1090                1095

Leu Ala  Asn Asn Ile Tyr Leu  Arg Ala Lys Lys Glu  Asn Leu Asn
    1100                1105                1110

Thr Asp  Lys Ile Ser Phe Asp  Tyr Phe Gly Ile Pro  Thr Ile Gly
    1115                1120                1125

Asn Gly  Arg Gly Ile Ala Glu  Ile Arg Gln Leu Tyr  Glu Lys Val
    1130                1135                1140

Asp Ser  Asp Ile Gln Ala Tyr  Ala Lys Gly Asp Lys  Pro Gln Ala
    1145                1150                1155

Ser Tyr  Ser His Leu Ile Asp  Ala Met Leu Ala Phe  Cys Ile Ala
    1160                1165                1170

Ala Asp  Glu His Arg Asn Asp  Gly Ser Ile Gly Leu  Glu Ile Asp
```

-continued

```
    1175                1180                1185

Lys Asn  Tyr Ser Leu Tyr Pro  Leu Asp Lys Asn Thr  Gly Glu Val
    1190                1195                1200

Phe Thr  Lys Asp Ile Phe Ser  Gln Ile Lys Ile Thr  Asp Asn Glu
    1205                1210                1215

Phe Ser  Asp Lys Lys Leu Val  Arg Lys Lys Ala Ile  Glu Gly Phe
    1220                1225                1230

Asn Thr  His Arg Gln Met Thr  Arg Asp Gly Ile Tyr  Ala Glu Asn
    1235                1240                1245

Tyr Leu  Pro Ile Leu Ile His  Lys Glu Leu Asn Glu  Val Arg Lys
    1250                1255                1260

Gly Tyr  Thr Trp Lys Asn Ser  Glu Glu Ile Lys Ile  Phe Lys Gly
    1265                1270                1275

Lys Lys  Tyr Asp Ile Gln Gln  Leu Asn Asn Leu Val  Tyr Cys Leu
    1280                1285                1290

Lys Phe  Val Asp Lys Pro Ile  Ser Ile Asp Ile Gln  Ile Ser Thr
    1295                1300                1305

Leu Glu  Glu Leu Arg Asn Ile  Leu Thr Thr Asn Asn  Ile Ala Ala
    1310                1315                1320

Thr Ala  Glu Tyr Tyr Tyr Ile  Asn Leu Lys Thr Gln  Lys Leu His
    1325                1330                1335

Glu Tyr  Tyr Ile Glu Asn Tyr  Asn Thr Ala Leu Gly  Tyr Lys Lys
    1340                1345                1350

Tyr Ser  Lys Glu Met Glu Phe  Leu Arg Ser Leu Ala  Tyr Arg Ser
    1355                1360                1365

Glu Arg  Val Lys Ile Lys Ser  Ile Asp Asp Val Lys  Gln Val Leu
    1370                1375                1380

Asp Lys  Asp Ser Asn Phe Ile  Ile Gly Lys Ile Thr  Leu Pro Phe
    1385                1390                1395

Lys Lys  Glu Trp Gln Arg Leu  Tyr Arg Glu Trp Gln  Asn Thr Thr
    1400                1405                1410

Ile Lys  Asp Asp Tyr Glu Phe  Leu Lys Ser Phe Phe  Asn Val Lys
    1415                1420                1425

Ser Ile  Thr Lys Leu His Lys  Lys Val Arg Lys Asp  Phe Ser Leu
    1430                1435                1440

Pro Ile  Ser Thr Asn Glu Gly  Lys Phe Leu Val Lys  Arg Lys Thr
    1445                1450                1455

Trp Asp  Asn Asn Phe Ile Tyr  Gln Ile Leu Asn Asp  Ser Asp Ser
    1460                1465                1470

Arg Ala  Asp Gly Thr Lys Pro  Phe Ile Pro Ala Phe  Asp Ile Ser
    1475                1480                1485

Lys Asn  Glu Ile Val Glu Ala  Ile Ile Asp Ser Phe  Thr Ser Lys
    1490                1495                1500

Asn Ile  Phe Trp Leu Pro Lys  Asn Ile Glu Leu Gln  Lys Val Asp
    1505                1510                1515

Asn Lys  Asn Ile Phe Ala Ile  Asp Thr Ser Lys Trp  Phe Glu Val
    1520                1525                1530

Glu Thr  Pro Ser Asp Leu Arg  Asp Ile Gly Ile Ala  Thr Ile Gln
    1535                1540                1545

Tyr Lys  Ile Asp Asn Asn Ser  Arg Pro Lys Val Arg  Val Lys Leu
    1550                1555                1560

Asp Tyr  Val Ile Asp Asp Asp  Ser Lys Ile Asn Tyr  Phe Met Asn
    1565                1570                1575
```

-continued

His Ser Leu Leu Lys Ser Arg Tyr Pro Asp Lys Val Leu Glu Ile
1580 1585 1590

Leu Lys Gln Ser Thr Ile Ile Glu Phe Glu Ser Ser Gly Phe Asn
1595 1600 1605

Lys Thr Ile Lys Glu Met Leu Gly Met Lys Leu Ala Gly Ile Tyr
1610 1615 1620

Asn Glu Thr Ser Asn Asn
1625

<210> SEQ ID NO 3
<211> LENGTH: 1899
<212> TYPE: PRT
<213> ORGANISM: Artificial Sequence
<220> FEATURE:
<223> OTHER INFORMATION: Protein sequence of recombinant dFnCas9 from Francisella novicida coupled with Green Fluorescent Protein

<400> SEQUENCE: 3

Val Ser Lys Gly Glu Glu Leu Phe Thr Gly Val Val Pro Ile Leu Val
1 5 10 15

Glu Leu Asp Gly Asp Val Asn Gly His Lys Phe Ser Val Arg Gly Glu
20 25 30

Gly Glu Gly Asp Ala Thr Asn Gly Lys Leu Thr Leu Lys Phe Ile Cys
35 40 45

Thr Thr Gly Lys Leu Pro Val Pro Trp Pro Thr Leu Val Thr Thr Leu
50 55 60

Thr Tyr Gly Val Gln Cys Phe Ser Arg Tyr Pro Asp His Met Lys Gln
65 70 75 80

His Asp Phe Phe Lys Ser Ala Met Pro Glu Gly Tyr Val Gln Glu Arg
85 90 95

Thr Ile Ser Phe Lys Asp Asp Gly Thr Tyr Lys Thr Arg Ala Glu Val
100 105 110

Lys Phe Glu Gly Asp Thr Leu Val Asn Arg Ile Glu Leu Lys Gly Ile
115 120 125

Asp Phe Lys Glu Asp Gly Asn Ile Leu Gly His Lys Leu Glu Tyr Asn
130 135 140

Phe Asn Ser His Asn Val Tyr Ile Thr Ala Asp Lys Gln Lys Asn Gly
145 150 155 160

Ile Lys Ala Asn Phe Lys Ile Arg His Asn Val Glu Asp Gly Ser Val
165 170 175

Gln Leu Ala Asp His Tyr Gln Gln Asn Thr Pro Ile Gly Asp Gly Pro
180 185 190

Val Leu Leu Pro Asp Asn His Tyr Leu Ser Thr Gln Ser Lys Leu Ser
195 200 205

Lys Asp Pro Asn Glu Lys Arg Asp His Met Val Leu Leu Glu Phe Val
210 215 220

Thr Ala Ala Gly Ile Thr Leu Gly Met Asp Glu Leu Tyr Lys Gly Ile
225 230 235 240

Glu Glu Asn Leu Tyr Phe Gln Ser Asn Ala Met Tyr Pro Tyr Asp Val
245 250 255

Pro Asp Tyr Ala Ser Pro Lys Lys Lys Arg Lys Val Glu Ala Ser Asn
260 265 270

Phe Lys Ile Leu Pro Ile Ala Ile Ala Leu Gly Val Lys Asn Thr Gly
275 280 285

Val Phe Ser Ala Phe Tyr Gln Lys Gly Thr Ser Leu Glu Arg Leu Asp

-continued

```
    290                 295                 300

Asn Lys Asn Gly Lys Val Tyr Glu Leu Ser Lys Asp Ser Tyr Thr Leu
305                 310                 315                 320

Leu Met Asn Asn Arg Thr Ala Arg Arg His Gln Arg Arg Gly Ile Asp
                325                 330                 335

Arg Lys Gln Leu Val Lys Arg Leu Phe Lys Leu Ile Trp Thr Glu Gln
            340                 345                 350

Leu Asn Leu Glu Trp Asp Lys Asp Thr Gln Gln Ala Ile Ser Phe Leu
        355                 360                 365

Phe Asn Arg Arg Gly Phe Ser Phe Ile Thr Asp Gly Tyr Ser Pro Glu
    370                 375                 380

Tyr Leu Asn Ile Val Pro Glu Gln Val Lys Ala Ile Leu Met Asp Ile
385                 390                 395                 400

Phe Asp Asp Tyr Asn Gly Glu Asp Asp Leu Asp Ser Tyr Leu Lys Leu
                405                 410                 415

Ala Thr Glu Gln Glu Ser Lys Ile Ser Glu Ile Tyr Asn Lys Leu Met
            420                 425                 430

Gln Lys Ile Leu Glu Phe Lys Leu Met Lys Leu Cys Thr Asp Ile Lys
        435                 440                 445

Asp Asp Lys Val Ser Thr Lys Thr Leu Lys Glu Ile Thr Ser Tyr Glu
    450                 455                 460

Phe Glu Leu Leu Ala Asp Tyr Leu Ala Asn Tyr Ser Glu Ser Leu Lys
465                 470                 475                 480

Thr Gln Lys Phe Ser Tyr Thr Asp Lys Gln Gly Asn Leu Lys Glu Leu
                485                 490                 495

Ser Tyr Tyr His His Asp Lys Tyr Asn Ile Gln Glu Phe Leu Lys Arg
            500                 505                 510

His Ala Thr Ile Asn Asp Arg Ile Leu Asp Thr Leu Leu Thr Asp Asp
        515                 520                 525

Leu Asp Ile Trp Asn Phe Asn Phe Glu Lys Phe Asp Phe Asp Lys Asn
    530                 535                 540

Glu Glu Lys Leu Gln Asn Gln Glu Asp Lys Asp His Ile Gln Ala His
545                 550                 555                 560

Leu His His Phe Val Phe Ala Val Asn Lys Ile Lys Ser Glu Met Ala
                565                 570                 575

Ser Gly Gly Arg His Arg Ser Gln Tyr Phe Gln Glu Ile Thr Asn Val
            580                 585                 590

Leu Asp Glu Asn Asn His Gln Glu Gly Tyr Leu Lys Asn Phe Cys Glu
        595                 600                 605

Asn Leu His Asn Lys Lys Tyr Ser Asn Leu Ser Val Lys Asn Leu Val
    610                 615                 620

Asn Leu Ile Gly Asn Leu Ser Asn Leu Glu Leu Lys Pro Leu Arg Lys
625                 630                 635                 640

Tyr Phe Asn Asp Lys Ile His Ala Lys Ala Asp His Trp Asp Glu Gln
                645                 650                 655

Lys Phe Thr Glu Thr Tyr Cys His Trp Ile Leu Gly Glu Trp Arg Val
            660                 665                 670

Gly Val Lys Asp Gln Asp Lys Lys Asp Gly Ala Lys Tyr Ser Tyr Lys
        675                 680                 685

Asp Leu Cys Asn Glu Leu Lys Gln Lys Val Thr Lys Ala Gly Leu Val
    690                 695                 700

Asp Phe Leu Leu Glu Leu Asp Pro Cys Arg Thr Ile Pro Pro Tyr Leu
705                 710                 715                 720
```

-continued

```
Asp Asn Asn Asn Arg Lys Pro Pro Lys Cys Gln Ser Leu Ile Leu Asn
                725                 730                 735

Pro Lys Phe Leu Asp Asn Gln Tyr Pro Asn Trp Gln Gln Tyr Leu Gln
            740                 745                 750

Glu Leu Lys Lys Leu Gln Ser Ile Gln Asn Tyr Leu Asp Ser Phe Glu
        755                 760                 765

Thr Asp Leu Lys Val Leu Lys Ser Ser Lys Asp Gln Pro Tyr Phe Val
    770                 775                 780

Glu Tyr Lys Ser Ser Asn Gln Gln Ile Ala Ser Gly Gln Arg Asp Tyr
785                 790                 795                 800

Lys Asp Leu Asp Ala Arg Ile Leu Gln Phe Ile Phe Asp Arg Val Lys
                805                 810                 815

Ala Ser Asp Glu Leu Leu Leu Asn Glu Ile Tyr Phe Gln Ala Lys Lys
            820                 825                 830

Leu Lys Gln Lys Ala Ser Ser Glu Leu Glu Lys Leu Glu Ser Ser Lys
        835                 840                 845

Lys Leu Asp Glu Val Ile Ala Asn Ser Gln Leu Ser Gln Ile Leu Lys
    850                 855                 860

Ser Gln His Thr Asn Gly Ile Phe Glu Gln Gly Thr Phe Leu His Leu
865                 870                 875                 880

Val Cys Lys Tyr Tyr Lys Gln Arg Gln Arg Ala Arg Asp Ser Arg Leu
                885                 890                 895

Tyr Ile Met Pro Glu Tyr Arg Tyr Asp Lys Lys Leu His Lys Tyr Asn
            900                 905                 910

Asn Thr Gly Arg Phe Asp Asp Asp Asn Gln Leu Leu Thr Tyr Cys Asn
        915                 920                 925

His Lys Pro Arg Gln Lys Arg Tyr Gln Leu Leu Asn Asp Leu Ala Gly
    930                 935                 940

Val Leu Gln Val Ser Pro Asn Phe Leu Lys Asp Lys Ile Gly Ser Asp
945                 950                 955                 960

Asp Asp Leu Phe Ile Ser Lys Trp Leu Val Glu His Ile Arg Gly Phe
                965                 970                 975

Lys Lys Ala Cys Glu Asp Ser Leu Lys Ile Gln Lys Asp Asn Arg Gly
            980                 985                 990

Leu Leu Asn His Lys Ile Asn Ile  Ala Arg Asn Thr Lys  Gly Lys Cys
        995                 1000                1005

Glu Lys  Glu Ile Phe Asn Leu  Ile Cys Lys Ile Glu  Gly Ser Glu
    1010                1015                1020

Asp Lys  Lys Gly Asn Tyr Lys  His Gly Leu Ala Tyr  Glu Leu Gly
    1025                1030                1035

Val Leu  Leu Phe Gly Glu Pro  Asn Glu Ala Ser Lys  Pro Glu Phe
    1040                1045                1050

Asp Arg  Lys Ile Lys Lys Phe  Asn Ser Ile Tyr Ser  Phe Ala Gln
    1055                1060                1065

Ile Gln  Gln Ile Ala Phe Ala  Glu Arg Lys Gly Asn  Ala Asn Thr
    1070                1075                1080

Cys Ala  Val Cys Ser Ala Asp  Asn Ala His Arg Met  Gln Gln Ile
    1085                1090                1095

Lys Ile  Thr Glu Pro Val Glu  Asp Asn Lys Asp Lys  Ile Ile Leu
    1100                1105                1110

Ser Ala  Lys Ala Gln Arg Leu  Pro Ala Ile Pro Thr  Arg Ile Val
    1115                1120                1125
```

-continued

```
Asp Gly  Ala Val Lys Lys Met  Ala Thr Ile Leu Ala  Lys Asn Ile
    1130                 1135                 1140

Val Asp  Asp Asn Trp Gln Asn  Ile Lys Gln Val Leu  Ser Ala Lys
    1145                 1150                 1155

His Gln  Leu His Ile Pro Ile  Ile Thr Glu Ser Asn  Ala Phe Glu
    1160                 1165                 1170

Phe Glu  Pro Ala Leu Ala Asp  Val Lys Gly Lys Ser  Leu Lys Asp
    1175                 1180                 1185

Arg Arg  Lys Lys Ala Leu Glu  Arg Ile Ser Pro Glu  Asn Ile Phe
    1190                 1195                 1200

Lys Asp  Lys Asn Asn Arg Ile  Lys Glu Phe Ala Lys  Gly Ile Ser
    1205                 1210                 1215

Ala Tyr  Ser Gly Ala Asn Leu  Thr Asp Gly Asp Phe  Asp Gly Ala
    1220                 1225                 1230

Lys Glu  Glu Leu Asp Ala Ile  Ile Pro Arg Ser His  Lys Lys Tyr
    1235                 1240                 1245

Gly Thr  Leu Asn Asp Glu Ala  Asn Leu Ile Cys Val  Thr Arg Gly
    1250                 1255                 1260

Asp Asn  Lys Asn Lys Gly Asn  Arg Ile Phe Cys Leu  Arg Asp Leu
    1265                 1270                 1275

Ala Asp  Asn Tyr Lys Leu Lys  Gln Phe Glu Thr Thr  Asp Asp Leu
    1280                 1285                 1290

Glu Ile  Glu Lys Lys Ile Ala  Asp Thr Ile Trp Asp  Ala Asn Lys
    1295                 1300                 1305

Lys Asp  Phe Lys Phe Gly Asn  Tyr Arg Ser Phe Ile  Asn Leu Thr
    1310                 1315                 1320

Pro Gln  Glu Gln Lys Ala Phe  Arg His Ala Leu Phe  Leu Ala Asp
    1325                 1330                 1335

Glu Asn  Pro Ile Lys Gln Ala  Val Ile Arg Ala Ile  Asn Asn Arg
    1340                 1345                 1350

Asn Arg  Thr Phe Val Asn Gly  Thr Gln Arg Tyr Phe  Ala Glu Val
    1355                 1360                 1365

Leu Ala  Asn Asn Ile Tyr Leu  Arg Ala Lys Lys Glu  Asn Leu Asn
    1370                 1375                 1380

Thr Asp  Lys Ile Ser Phe Asp  Tyr Phe Gly Ile Pro  Thr Ile Gly
    1385                 1390                 1395

Asn Gly  Arg Gly Ile Ala Glu  Ile Arg Gln Leu Tyr  Glu Lys Val
    1400                 1405                 1410

Asp Ser  Asp Ile Gln Ala Tyr  Ala Lys Gly Asp Lys  Pro Gln Ala
    1415                 1420                 1425

Ser Tyr  Ser His Leu Ile Asp  Ala Met Leu Ala Phe  Cys Ile Ala
    1430                 1435                 1440

Ala Asp  Glu His Arg Asn Asp  Gly Ser Ile Gly Leu  Glu Ile Asp
    1445                 1450                 1455

Lys Asn  Tyr Ser Leu Tyr Pro  Leu Asp Lys Asn Thr  Gly Glu Val
    1460                 1465                 1470

Phe Thr  Lys Asp Ile Phe Ser  Gln Ile Lys Ile Thr  Asp Asn Glu
    1475                 1480                 1485

Phe Ser  Asp Lys Lys Leu Val  Arg Lys Lys Ala Ile  Glu Gly Phe
    1490                 1495                 1500

Asn Thr  His Arg Gln Met Thr  Arg Asp Gly Ile Tyr  Ala Glu Asn
    1505                 1510                 1515

Tyr Leu  Pro Ile Leu Ile His  Lys Glu Leu Asn Glu  Val Arg Lys
```

```
    1520                1525                1530

Gly Tyr  Thr Trp Lys Asn Ser  Glu Glu Ile Lys Ile  Phe Lys Gly
    1535                1540                1545

Lys Lys  Tyr Asp Ile Gln Gln  Leu Asn Asn Leu Val  Tyr Cys Leu
    1550                1555                1560

Lys Phe  Val Asp Lys Pro Ile  Ser Ile Asp Ile Gln  Ile Ser Thr
    1565                1570                1575

Leu Glu  Glu Leu Arg Asn Ile  Leu Thr Thr Asn Asn  Ile Ala Ala
    1580                1585                1590

Thr Ala  Glu Tyr Tyr Tyr Ile  Asn Leu Lys Thr Gln  Lys Leu His
    1595                1600                1605

Glu Tyr  Tyr Ile Glu Asn Tyr  Asn Thr Ala Leu Gly  Tyr Lys Lys
    1610                1615                1620

Tyr Ser  Lys Glu Met Glu Phe  Leu Arg Ser Leu Ala  Tyr Arg Ser
    1625                1630                1635

Glu Arg  Val Lys Ile Lys Ser  Ile Asp Asp Val Lys  Gln Val Leu
    1640                1645                1650

Asp Lys  Asp Ser Asn Phe Ile  Ile Gly Lys Ile Thr  Leu Pro Phe
    1655                1660                1665

Lys Lys  Glu Trp Gln Arg Leu  Tyr Arg Glu Trp Gln  Asn Thr Thr
    1670                1675                1680

Ile Lys  Asp Asp Tyr Glu Phe  Leu Lys Ser Phe Phe  Asn Val Lys
    1685                1690                1695

Ser Ile  Thr Lys Leu His Lys  Lys Val Arg Lys Asp  Phe Ser Leu
    1700                1705                1710

Pro Ile  Ser Thr Asn Glu Gly  Lys Phe Leu Val Lys  Arg Lys Thr
    1715                1720                1725

Trp Asp  Asn Asn Phe Ile Tyr  Gln Ile Leu Asn Asp  Ser Asp Ser
    1730                1735                1740

Arg Ala  Asp Gly Thr Lys Pro  Phe Ile Pro Ala Phe  Asp Ile Ser
    1745                1750                1755

Lys Asn  Glu Ile Val Glu Ala  Ile Ile Asp Ser Phe  Thr Ser Lys
    1760                1765                1770

Asn Ile  Phe Trp Leu Pro Lys  Asn Ile Glu Leu Gln  Lys Val Asp
    1775                1780                1785

Asn Lys  Asn Ile Phe Ala Ile  Asp Thr Ser Lys Trp  Phe Glu Val
    1790                1795                1800

Glu Thr  Pro Ser Asp Leu Arg  Asp Ile Gly Ile Ala  Thr Ile Gln
    1805                1810                1815

Tyr Lys  Ile Asp Asn Asn Ser  Arg Pro Lys Val Arg  Val Lys Leu
    1820                1825                1830

Asp Tyr  Val Ile Asp Asp Asp  Ser Lys Ile Asn Tyr  Phe Met Asn
    1835                1840                1845

His Ser  Leu Leu Lys Ser Arg  Tyr Pro Asp Lys Val  Leu Glu Ile
    1850                1855                1860

Leu Lys  Gln Ser Thr Ile Ile  Glu Phe Glu Ser Ser  Gly Phe Asn
    1865                1870                1875

Lys Thr  Ile Lys Glu Met Leu  Gly Met Lys Leu Ala  Gly Ile Tyr
    1880                1885                1890

Asn Glu  Thr Ser Asn Asn
    1895
```

<210> SEQ ID NO 4

-continued

<211> LENGTH: 502
<212> TYPE: DNA
<213> ORGANISM: Artificial Sequence
<220> FEATURE:
<223> OTHER INFORMATION: Synthetic DNA containing portion of human gene encoding for Glycogen storage disease type I

<400> SEQUENCE: 4
agcataggag atggaatttg ttaaataaat gaattatgga taacgaatgg atggtaagat 60
gggtggatgg atggggggtg aacggatgga tggggggtga atggatggat gaatgggtag 120
atgggtggat agggggatgg ctgggtggct gggtagatga tgcactgtct cccagatgag 180 gacctttca cctttactcc attctctttc ctgcccttta gggagcccct ctggccatgc 240
catgggcaca acaggtgtat actacgtgat ggtcacatct actctttcca tctttcaggg 300
aaagataaag ccgacctaca gatttcggta agaactcacc actggggtgt aggtggtgga 360
gggcaggagg cagctctctc tgtagctgac acaccacgta ttcttcctca catcccccta 420
gcccgctccc acacctgggc agccgctgat taagagttgt ggcactttgg atagggataa 480
acctcagagt cagggaatgt tt 502

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA for SgRNA seq.1 against Glycogen storage disease type I

<400> SEQUENCE: 5
ggccatgcca tgggaacaac 20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA for SgRNA seq.2 against Glycogen storage disease type I

<400> SEQUENCE: 6
ggccatgcca tgagcacaac 20

<210> SEQ ID NO 7
<211> LENGTH: 502
<212> TYPE: DNA
<213> ORGANISM: Artificial Sequence
<220> FEATURE:
<223> OTHER INFORMATION: Synthetic DNA containing portion of human gene encoding for Glanzmann thrombosthenia

<400> SEQUENCE: 7
tcccagggac caagcgtggc ccacagaggc ccacagcaca cccggacccc tctccctcct 60
cccatcccct ctgccccgtg ggtcccgggg aggccgggcc agagaccaga gagcctgctc 120
actacgagaa ctggatcctg aagcctcgag ggctgctcgg gctctggcag gaagatctgt 180
ctgcgatccc gcttgtgatg ggccgggtga atgggggagg ggctggggat gggcagcccc 240
cagtccacct cggggggcaa aggagtggtc aggcccaggt ctcccccgaa ccccagccca 300
cagaggtgcc ccggtggttg gtctggggcc gccttcccag gtctttcttc cacccagctc 360
ttaccttgag agggttgaca ggaggctgtg ggaagcactg aaggccccccc tggggctgta 420 tatccaggat gtagagcagg tcggagggct gggactgtcc cggaaggtgg atgctgaggt 480
gaagaccatt cacagtccca gg 502

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA for SgRNA seq.1 against Glanzmann thrombasthenia

<400> SEQUENCE: 8
gcagccccca gtccgcctcg 20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA for SgRNA seq.2 against Glanzmann thrombasthenia

<400> SEQUENCE: 9
gcagccccca gtacacctcg 20

<210> SEQ ID NO 10
<211> LENGTH: 500
<212> TYPE: DNA
<213> ORGANISM: Artificial Sequence
<220> FEATURE:
<223> OTHER INFORMATION: Synthetic DNA containing portion of human gene encoding for X-linked myotubular myopathy

<400> SEQUENCE: 10
catggaagta tatattattt cctctctgag aaacttggca tttagaaggc acattgctga 60
attgtattgt cacattttgt gttatatgct ttctcagttt tgtacccatt aattaaaaca 120
aattatcttc atcaatttat tcagcgaata ggtcatggtg ataaaaacca caccgatgct 180
gaccgttctc ctatttttct ccagtttatt gattgtgtgt ggcaaatgtc aaaacaggca 240
aggaatatga gggatgaaaa tacattcaac tcattgttta aattaaacat tttaatataa 300
tgattgggat ttgaccccaa aataatacag ggtagagcta gagatgaagc aagactgggc 360
atgtgtgaat acttgcagaa gccaggtaca tgagcgttca cctttttatt cctgctacta 420
ttgatatatc tgggattttc cctaataaag ttttaaaaat taagtattta actctgatgt 480
ctctactagt ggaattgaca 500

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA for SgRNA seq.1 against X-linked myotubular myopathy

<400> SEQUENCE: 11
ggcaaatgtc aaaaaaggca 20

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA for SgRNA seq.2 against X-linked myotubular myopathy

<400> SEQUENCE: 12
ggcaaatgtc aagacaggca 20

<210> SEQ ID NO 13
<211> LENGTH: 502
<212> TYPE: DNA
<213> ORGANISM: Artificial Sequence
<220> FEATURE:
<223> OTHER INFORMATION: Synthetic DNA containing portion of human gene encoding for Hereditary Factor VIII deficiency disease(HA)

<400> SEQUENCE: 13
tgcaggactg atgatagtta attcaggagg cttcaaggca gtgtctgcta ggatttagca 60
caaaggtaga aggcaagcca gggagggaca ctgccctgga gctgaggagg gagaggtgac 120
ggcagtggca ggtgctgcag tggccaccct cagtagaggt cctgtgcctc gcagcccaga 180
acctccatcc tcagggcaat ctggtgcacc caactctggg ggtgaattcg aaggtagcga 240
gtcagtaacg atgggtctag agagttcacc acaggtgtga aggagtcttg atttccctga 300
aaaacctgaa agaggaaaga tagcatttat tggttgtctg acaggacaat ggtcactgca 360
aagcacagac gcttttctca cttctagttg tttccagtag tccaggatta aaccctggaa 420
gatgactaga tgactctgtc ctacgcatct gggacatcta gaattaagag caccctgctt 480
tggaggcctt cactctagct ag 502

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA for SgRNA seq 1 against Hereditary factor VIII deficiency disease(HA)

<400> SEQUENCE: 14
ggtagcgagt cagtgacgat 20

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA for SgRNA seq.2 against Hereditary factor VIII deficiency disease(HA)

<400> SEQUENCE: 15
ggtagcgagt caataacgat 20

<210> SEQ ID NO 16
<211> LENGTH: 550
<212> TYPE: DNA
<213> ORGANISM: Artificial Sequence
<220> FEATURE:
<223> OTHER INFORMATION: Synthetic DNA containing portion of human gene encoding for Sickle Cell Anemia

<400> SEQUENCE: 16
actcctaagc cagtgccaga agagccaagg acaggtacgg ctgtcatcac ttagacctca 60
ccctgtggag ccacacccta gggttggcca atctactccc aggagcaggg agggcaggag 120
ccagggctgg gcataaaagt cagggcagag ccatctattg cttacatttg cttctgacac 180
aactgtgttc actagcaacc tcaaacagac accatggtgc atctgactcc tgaggagaag 240

-continued tctgccgtta ctgccctgtg gggcaaggtg aacgtggatg aagttggtgg tgaggccctg 300
ggcaggttgg tatcaaggtt acaagacagg tttaaggaga ccaatagaaa ctgggcatgt 360
ggagacagag aagactcttg ggtttctgat aggcactgac tctctctgcc tattggtcta 420
ttttcccacc cttaggctgc tggtggtcta cccttggacc cagaggttct ttgagtcctt 480
tggggatctg tccactcctg atgctgttat gggcaaccct aaggtgaagg ctcatggcaa 540
gaaagtgctc 550

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA for SgRNA seq.1 against Sickle cell Anemia (SCA)

<400> SEQUENCE: 17
gtaacggcag acttctcctc 20

<210> SEQ ID NO 18
<211> LENGTH: 20
<212> TYPE: DNA
<213> ORGANISM: Artificial Sequence
<220> FEATURE:
<223> OTHER INFORMATION: Synthetic DNA for SgRNA seq.2 against Sickle cell Anemia (SCA)

<400> SEQUENCE: 18
gtaacggcag acttatccac 20

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA for double mismatch at HBB locus 1

<400> SEQUENCE: 19
gtaacggcag acttctcaac 20

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA for double mismatch at HBB locus 2

<400> SEQUENCE: 20
gtaacggcag acttctacac 20

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA for double mismatch at HBB locus 3

<400> SEQUENCE: 21
gtaacggcag acttcaccac 20

<210> SEQ ID NO 22

-continued

<211> LENGTH: 20
<212> TYPE: DNA
<213> ORGANISM: Artificial Sequence
<220> FEATURE:
<223> OTHER INFORMATION: Synthetic DNA for double mismatch at HBB locus
4

<400> SEQUENCE: 22
gtaacggcag acttatccac 20

<210> SEQ ID NO 23
<211> LENGTH: 20
<212> TYPE: DNA
<213> ORGANISM: Artificial Sequence
<220> FEATURE:
<223> OTHER INFORMATION: Synthetic DNA for double mismatch at HBB locus
5

<400> SEQUENCE: 23
gtaacggcag actactccac 20

<210> SEQ ID NO 24
<211> LENGTH: 20
<212> TYPE: DNA
<213> ORGANISM: Artificial Sequence
<220> FEATURE:
<223> OTHER INFORMATION: Synthetic DNA for double mismatch at HBB locus
6

<400> SEQUENCE: 24
gtaacggcag acatctccac 20

<210> SEQ ID NO 25
<211> LENGTH: 20
<212> TYPE: DNA
<213> ORGANISM: Artificial Sequence
<220> FEATURE:
<223> OTHER INFORMATION: Synthetic DNA for double mismatch at HBB locus
7

<400> SEQUENCE: 25
gtaacggcag aattctccac 20

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA for double mismatch at HBB locus
8

<400> SEQUENCE: 26
gtaacggcag ccttctccac 20

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA for double mismatch at HBB locus
9

<400> SEQUENCE: 27
gtaactgcag acttctccac 20

<210> SEQ ID NO 28
<211> LENGTH: 20

```
<212> TYPE: DNA
<213> ORGANISM: Artificial Sequence
<220> FEATURE:
<223> OTHER INFORMATION: Synthetic DNA for double mismatch at HBB locus
      10

<400> SEQUENCE: 28

gtaaaggcag acttctccac                                                20


<210> SEQ ID NO 29
<211> LENGTH: 20
<212> TYPE: DNA
<213> ORGANISM: Artificial Sequence
<220> FEATURE:
<223> OTHER INFORMATION: Synthetic DNA for double mismatch at HBB locus
      11

<400> SEQUENCE: 29

gtaccggcag acttctccac                                                20


<210> SEQ ID NO 30
<211> LENGTH: 20
<212> TYPE: DNA
<213> ORGANISM: Artificial Sequence
<220> FEATURE:
<223> OTHER INFORMATION: Synthetic DNA for double mismatch at HBB locus
      12

<400> SEQUENCE: 30

gtcacggcag acttctccac                                                20


<210> SEQ ID NO 31
<211> LENGTH: 20
<212> TYPE: DNA
<213> ORGANISM: Artificial Sequence
<220> FEATURE:
<223> OTHER INFORMATION: Synthetic DNA for double mismatch at HBB locus
      13

<400> SEQUENCE: 31

gaaacggcag acttctccac                                                20


<210> SEQ ID NO 32
<211> LENGTH: 20
<212> TYPE: DNA
<213> ORGANISM: Artificial Sequence
<220> FEATURE:
<223> OTHER INFORMATION: Synthetic WT sgRNA sequence for human HBB locus

<400> SEQUENCE: 32

gtaacggcag acttctcctc                                                20


<210> SEQ ID NO 33
<211> LENGTH: 20
<212> TYPE: DNA
<213> ORGANISM: Artificial Sequence
<220> FEATURE:
<223> OTHER INFORMATION: Synthetic sgRNA sequence with mismatches at PAM
      proximal 2 and 6 positions

<400> SEQUENCE: 33

gtaacggcag acttatccac                                                20


<210> SEQ ID NO 34
<211> LENGTH: 20
<212> TYPE: DNA
<213> ORGANISM: Artificial Sequence
```

-continued

<220> FEATURE:
<223> OTHER INFORMATION: Synthetic DNA sequence for HBB mismatched target 1

<400> SEQUENCE: 34
gaagaaaagt ctgccgttac 20

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA sequence for HBB mismatched target 2

<400> SEQUENCE: 35
gaggagaagt ctgccattgc 20

<210> SEQ ID NO 36
<211> LENGTH: 72
<212> TYPE: DNA
<213> ORGANISM: Artificial Sequence
<220> FEATURE:
<223> OTHER INFORMATION: sgRNA with 1 mismatch for Glycogen Storage disease type I SNV and 2 mismatch for wild type sequence at 6th and 2nd position

<400> SEQUENCE: 36
taatacgact cactataggc catgccatgg gaacaacgtt tcagttgcgc cgaaaggcgc 60
tctgtaatca tt 72

<210> SEQ ID NO 37
<211> LENGTH: 24
<212> TYPE: DNA
<213> ORGANISM: Artificial Sequence
<220> FEATURE:
<223> OTHER INFORMATION: PCR primer for Glycogen storage disease type I

<400> SEQUENCE: 37
gcataggaga tggaatttgt taaa 24

<210> SEQ ID NO 38
<211> LENGTH: 22
<212> TYPE: DNA
<213> ORGANISM: Artificial Sequence
<220> FEATURE:
<223> OTHER INFORMATION: TCCCTGACTCTGAGGTTTATCC

<400> SEQUENCE: 38
tccctgactc tgaggtttat cc 22

<210> SEQ ID NO 39
<211> LENGTH: 72
<212> TYPE: DNA
<213> ORGANISM: Artificial Sequence
<220> FEATURE:
<223> OTHER INFORMATION: sgRNA with 1 mismatch for Glanzman ThRombasthenia SNV and 2 mismatch for wild type sequence at 6th and 2nd position

<400> SEQUENCE: 39
taatacgact cactatagca gcccccagtc cgcctcggtt tcagttgcgc cgaaaggcgc 60
tctgtaatca tt 72

<210> SEQ ID NO 40

-continued

<211> LENGTH: 19
<212> TYPE: DNA
<213> ORGANISM: Artificial Sequence
<220> FEATURE:
<223> OTHER INFORMATION: PCR primer for Glanzmann thrombasthenia disease

<400> SEQUENCE: 40
acagaggccc acagcacac 19

<210> SEQ ID NO 41
<211> LENGTH: 20
<212> TYPE: DNA
<213> ORGANISM: Artificial Sequence
<220> FEATURE:
<223> OTHER INFORMATION: PCR primer for Glanzmann thrombasthenia disease

<400> SEQUENCE: 41
cctgggactg tgaatggtct 20

<210> SEQ ID NO 42
<211> LENGTH: 72
<212> TYPE: DNA
<213> ORGANISM: Artificial Sequence
<220> FEATURE:
<223> OTHER INFORMATION: sgRNA with 1 mismatch for X-Linked myotubular myopathy SNV and 2 mismatch for wild type sequence at 6th and 2nd position

<400> SEQUENCE: 42
taatacgact cactataggc aaatgtcaag acaggcagtt tcagttgcgc cgaaaggcgc 60
tctgtaatca tt 72

<210> SEQ ID NO 43
<211> LENGTH: 22
<212> TYPE: DNA
<213> ORGANISM: Artificial Sequence
<220> FEATURE:
<223> OTHER INFORMATION: PCR primer for X-linked myotubular myopathy disease

<400> SEQUENCE: 43
cctctctgag aaacttggca tt 22

<210> SEQ ID NO 44
<211> LENGTH: 26
<212> TYPE: DNA
<213> ORGANISM: Artificial Sequence
<220> FEATURE:
<223> OTHER INFORMATION: PCR primer for X-linked myotubular myopathy disease

<400> SEQUENCE: 44
tgtcaattcc actagtagag acatca 26

<210> SEQ ID NO 45
<211> LENGTH: 72
<212> TYPE: DNA
<213> ORGANISM: Artificial Sequence
<220> FEATURE:
<223> OTHER INFORMATION: sgRNA with 1 mismatch for Hemophilia A(FactoR VIII) deficiency SNV and 2 mismatch for wild type sequence at 6th and 2nd position

<400> SEQUENCE: 45
taatacgact cactataggt agcgagtcag tgacgatgtt tcagttgcgc cgaaaggcgc 60
tctgtaatca tt 72

<210> SEQ ID NO 46
<211> LENGTH: 25
<212> TYPE: DNA
<213> ORGANISM: Artificial Sequence
<220> FEATURE:
<223> OTHER INFORMATION: PCR primer for hereditory FactoR VIII deficiency disease

<400> SEQUENCE: 46
gcaggactga tgatagttaa ttcag 25

<210> SEQ ID NO 47
<211> LENGTH: 20
<212> TYPE: DNA
<213> ORGANISM: Artificial Sequence
<220> FEATURE:
<223> OTHER INFORMATION: PCR primer for hereditory FactoR VIII deficiency disease

<400> SEQUENCE: 47
gagtgaaggc ctccaaagca 20

<210> SEQ ID NO 48
<211> LENGTH: 72
<212> TYPE: DNA
<213> ORGANISM: Artificial Sequence
<220> FEATURE:
<223> OTHER INFORMATION: sgRNA sequence for IVC against plasmid containing HBB sequence

<400> SEQUENCE: 48
taatacgact cactatagta acggcagact tctcctcgtt tcagttgcgc cgaaaggcgc 60
tctgtaatca tt 72

<210> SEQ ID NO 49
<211> LENGTH: 20
<212> TYPE: DNA
<213> ORGANISM: Artificial Sequence
<220> FEATURE:
<223> OTHER INFORMATION: PCR primer for 228bp HBB locus amplicon

<400> SEQUENCE: 49
tctccacatg cccagtttct 20

<210> SEQ ID NO 50
<211> LENGTH: 20
<212> TYPE: DNA
<213> ORGANISM: Artificial Sequence
<220> FEATURE:
<223> OTHER INFORMATION: PCR primer for 228bp HBB locus amplicon

<400> SEQUENCE: 50
agtcagggca gagccatcta 20

<210> SEQ ID NO 51
<211> LENGTH: 72
<212> TYPE: DNA
<213> ORGANISM: Artificial Sequence
<220> FEATURE:
<223> OTHER INFORMATION: sgRNA with 2 mismatches with Respect to HBB locus sgRNA keeping mismatch at 2nd and 3Rd position of sgRNA

<400> SEQUENCE: 51
taatacgact cactatagta acggcagact tctcaacgtt tcagttgcgc cgaaaggcgc 60

-continued

```
tctgtaatca tt                                                          72


<210> SEQ ID NO 52
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 4th position of sgRNA

<400> SEQUENCE: 52

taatacgact cactatagta acggcagact tctacacgtt tcagttgcgc cgaaaggcgc     60

tctgtaatca tt                                                          72


<210> SEQ ID NO 53
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 5th position of sgRNA

<400> SEQUENCE: 53

taatacgact cactatagta acggcagact tcaccacgtt tcagttgcgc cgaaaggcgc     60

tctgtaatca tt                                                          72


<210> SEQ ID NO 54
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 6th position of sgRNA

<400> SEQUENCE: 54

taatacgact cactatagta acggcagact tatccacgtt tcagttgcgc cgaaaggcgc     60

tctgtaatca tt                                                          72


<210> SEQ ID NO 55
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 7th position of sgRNA

<400> SEQUENCE: 55

taatacgact cactatagta acggcagact actccacgtt tcagttgcgc cgaaaggcgc     60

tctgtaatca tt                                                          72


<210> SEQ ID NO 56
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 8th position of sgRNA

<400> SEQUENCE: 56

taatacgact cactatagta acggcagaca tctccacgtt tcagttgcgc cgaaaggcgc     60

tctgtaatca tt                                                          72


<210> SEQ ID NO 57
```

-continued

```
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 9th position of sgRNA

<400> SEQUENCE: 57

taatacgact cactatagta acggcagaat tctccacgtt tcagttgcgc cgaaaggcgc     60

tctgtaatca tt                                                         72


<210> SEQ ID NO 58
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 10th position of sgRNA

<400> SEQUENCE: 58

taatacgact cactatagta acggcagcct tctccacgtt tcagttgcgc cgaaaggcgc     60

tctgtaatca tt                                                         72


<210> SEQ ID NO 59
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 15th position of sgRNA

<400> SEQUENCE: 59

taatacgact cactatagta actgcagact tctccacgtt tcagttgcgc cgaaaggcgc     60

tctgtaatca tt                                                         72


<210> SEQ ID NO 60
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 16th position of sgRNA

<400> SEQUENCE: 60

taatacgact cactatagta aaggcagact tctccacgtt tcagttgcgc cgaaaggcgc     60

tctgtaatca tt                                                         72


<210> SEQ ID NO 61
<211> LENGTH: 72
<212> TYPE: DNA
<213> ORGANISM: Artificial Sequence
<220> FEATURE:
<223> OTHER INFORMATION: sgRNA with 2 mismatches with Respect to HBB
      locus sgRNA keeping mismatch at 2nd and 17th position of sgRNA

<400> SEQUENCE: 61

taatacgact cactatagta ccggcagact tctccacgtt tcagttgcgc cgaaaggcgc     60

tctgtaatca tt                                                         72


<210> SEQ ID NO 62
<211> LENGTH: 72
<212> TYPE: DNA
<213> ORGANISM: Artificial Sequence
<220> FEATURE:
```

-continued

<223> OTHER INFORMATION: sgRNA with 2 mismatches with Respect to HBB locus sgRNA keeping mismatch at 2nd and 18th position of sgRNA

<400> SEQUENCE: 62
taatacgact cactatagtc acggcagact tctccacgtt tcagttgcgc cgaaaggcgc 60
tctgtaatca tt 72

<210> SEQ ID NO 63
<211> LENGTH: 72
<212> TYPE: DNA
<213> ORGANISM: Artificial Sequence
<220> FEATURE:
<223> OTHER INFORMATION: sgRNA with 2 mismatches with Respect to HBB locus sgRNA keeping mismatch at 2nd and 19th position of sgRNA

<400> SEQUENCE: 63
taatacgact cactatagaa acggcagact tctccacgtt tcagttgcgc cgaaaggcgc 60
tctgtaatca tt 72

<210> SEQ ID NO 64
<211> LENGTH: 20
<212> TYPE: DNA
<213> ORGANISM: Artificial Sequence
<220> FEATURE:
<223> OTHER INFORMATION: N gene crRNA sequence feluda

<400> SEQUENCE: 64
gtggcagtac gtttttgccg 20

<210> SEQ ID NO 65
<211> LENGTH: 56
<212> TYPE: DNA
<213> ORGANISM: Artificial Sequence
<220> FEATURE:
<223> OTHER INFORMATION: SARS_CoV2 N gene crRNA Forword primer oligo for IVT

<400> SEQUENCE: 65
taatacgact cactatagtg gcagtacgtt tttgccggtt tcagttgctg aattat 56

<210> SEQ ID NO 66
<211> LENGTH: 56
<212> TYPE: DNA
<213> ORGANISM: Artificial Sequence
<220> FEATURE:
<223> OTHER INFORMATION: SARS_CoV2 N gene crRNA reverse primer oligo for IVT

<400> SEQUENCE: 66
ataattcagc aactgaaacc gagggaattt aaggtcttct atagtgagtc gtatta 56

<210> SEQ ID NO 67
<211> LENGTH: 20
<212> TYPE: DNA
<213> ORGANISM: Artificial Sequence
<220> FEATURE:
<223> OTHER INFORMATION: S gene crRNA3 feluda

<400> SEQUENCE: 67
gacattacac catgttcttt 20

<210> SEQ ID NO 68
<211> LENGTH: 56
<212> TYPE: DNA
<213> ORGANISM: Artificial Sequence -continued
<220> FEATURE:
<223> OTHER INFORMATION: SARS_CoV2 S gene crRNA  Forward primer oligo
      for IVT feluda

<400> SEQUENCE: 68
taatacgact cactatagac attacaccat gttctttgtt tcagttgctg aattat        56

<210> SEQ ID NO 69
<211> LENGTH: 56
<212> TYPE: DNA
<213> ORGANISM: Artificial Sequence
<220> FEATURE:
<223> OTHER INFORMATION: SARS_CoV2 S gene crRNA reverse primer oligo for
      IVT feluda

<400> SEQUENCE: 69
ataattcagc aactgaaacc taattacaaa tgaatctgct atagtgagtc gtatta        56

<210> SEQ ID NO 70
<211> LENGTH: 39
<212> TYPE: RNA
<213> ORGANISM: Artificial Sequence
<220> FEATURE:
<223> OTHER INFORMATION: synthetic chimeric guide RNA part 1
<220> FEATURE:
<221> NAME/KEY: misc_feature
<222> LOCATION: (1)..(20)
<223> OTHER INFORMATION: n is a, c, g, or u

<400> SEQUENCE: 70
nnnnnnnnnn nnnnnnnnnn guuucaguug cugaauuau                              39

<210> SEQ ID NO 71
<211> LENGTH: 61
<212> TYPE: RNA
<213> ORGANISM: Artificial Sequence
<220> FEATURE:
<223> OTHER INFORMATION: Syntehtic chimerric guide RNA part 2

<400> SEQUENCE: 71
guaauuaaug cucuguaauc auuuaaaagu auuuugaacg gaccucuguu ugacacgucu     60
g                                                                     61

<210> SEQ ID NO 72
<211> LENGTH: 39
<212> TYPE: RNA
<213> ORGANISM: Artificial Sequence
<220> FEATURE:
<223> OTHER INFORMATION: Phosphorothioate modification between positions
      1 and 2, and 37 and 38

<400> SEQUENCE: 72
gacauuacac cauguucuuu guuucaguug cugaauuau                              39

<210> SEQ ID NO 73
<211> LENGTH: 61
<212> TYPE: RNA
<213> ORGANISM: Artificial Sequence
<220> FEATURE:
<223> OTHER INFORMATION: Phosphorothioate modification between positions
      1 and 2, and position 59 and 60. FAM modification at 3' position.

<400> SEQUENCE: 73
guaauuaaug cucuguaauc auuuaaaagu auuuugaacg gaccucuguu ugacacgucu     60
g                                                                     61

<210> SEQ ID NO 74
<211> LENGTH: 106
<212> TYPE: DNA
<213> ORGANISM: Artificial Sequence
<220> FEATURE:
<223> OTHER INFORMATION: Nucletide sequence corresponding to sgRNA for a
representative locus
<220> FEATURE:
<221> NAME/KEY: misc_feature
<222> LOCATION: (1)..(20)
<223> OTHER INFORMATION: n is a, c, g, or t

<400> SEQUENCE: 74
nnnnnnnnnn nnnnnnnnnn agggttttag agctagaaat agcaagttaa aataaggcta 60
gtccgttatc aacttgaaaa agtggcaccg agtcggtgct tttttt 106

<210> SEQ ID NO 75
<211> LENGTH: 106
<212> TYPE: DNA
<213> ORGANISM: Artificial Sequence
<220> FEATURE:
<223> OTHER INFORMATION: nucleotide sequence corresponding to a
representative example of sgRNA

<400> SEQUENCE: 75
gtaacggcag acttctcctc agggttttag agctagaaat agcaagttaa aataaggcta 60
gtccgttatc aacttgaaaa agtggcaccg agtcggtgct tttttt 106

<210> SEQ ID NO 76
<211> LENGTH: 96
<212> TYPE: DNA
<213> ORGANISM: Artificial Sequence
<220> FEATURE:
<223> OTHER INFORMATION: Nucleotide sequence corresponding to
representative sgRNA for HBB
<220> FEATURE:
<221> NAME/KEY: misc_feature
<222> LOCATION: (1)..(20)
<223> OTHER INFORMATION: n is a, c, g, or t

<400> SEQUENCE: 76
nnnnnnnnnn nnnnnnnnnn agggtttcag ttgcgccgaa aggcgctctg taatcattta 60
aaagtatttt gaacggacct ctgtttgaca cgtctg 96

<210> SEQ ID NO 77
<211> LENGTH: 96
<212> TYPE: DNA
<213> ORGANISM: Artificial Sequence
<220> FEATURE:
<223> OTHER INFORMATION: Nucleotide corresponding to representative
sgRNA for HBB locus

<400> SEQUENCE: 77
gtaacggcag acttctcctc agggtttcag ttgcgccgaa aggcgctctg taatcattta 60
aaagtatttt gaacggacct ctgtttgaca cgtctg 96

<210> SEQ ID NO 78
<211> LENGTH: 99
<212> TYPE: DNA
<213> ORGANISM: Artificial Sequence
<220> FEATURE:
<223> OTHER INFORMATION: Nucleotide corresponding to representative
sgRNA sequence for SpCas9

<400> SEQUENCE: 78

```
gtaacggcag acttatccac agggttttag agctagaaat agcaagttaa aataaggcta     60

gtccgttatc aacttgaaaa agtggcaccg agtcggtgc                            99


<210> SEQ ID NO 79
<211> LENGTH: 39
<212> TYPE: RNA
<213> ORGANISM: Artificial Sequence
<220> FEATURE:
<223> OTHER INFORMATION: Synthetic representative single guide RNA for
      FnCas9

<400> SEQUENCE: 79

gguccaccaa acguaaugcg guuucaguug cugaauuau                            39


<210> SEQ ID NO 80
<211> LENGTH: 96
<212> TYPE: DNA
<213> ORGANISM: Artificial Sequence
<220> FEATURE:
<223> OTHER INFORMATION: Generic FnCas9 sgRNA sequence for disease
      detection with one mismatch at positions 16 /17 /18 /19 bp away
      from PAM
<220> FEATURE:
<221> NAME/KEY: misc_feature
<222> LOCATION: (1)..(20)
<223> OTHER INFORMATION: n is a, c, g, or t

<400> SEQUENCE: 80

nnnnnnnnnn nnnnnnnnnn agggtttcag ttgcgccgaa aggcgctctg taatcattta     60

aaagtatttt gaacggacct ctgtttgaca cgtctg                               96


<210> SEQ ID NO 81
<211> LENGTH: 20
<212> TYPE: DNA
<213> ORGANISM: Helicobacter pylori

<400> SEQUENCE: 81

gaggagaagt ctgccgttac                                                 20


<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

gtaacggcag acttatccac                                                 20


<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

gtggagaagt ctgccgttac                                                 20


<210> SEQ ID NO 84
<211> LENGTH: 40
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 84
gtggagaagt ctgccgttac cacctattca gacggcaatg 40

<210> SEQ ID NO 85
<211> LENGTH: 20
<212> TYPE: DNA
<213> ORGANISM: Helicobacter pylori

<400> SEQUENCE: 85
gacggaaaga ccccgtggac 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gacgggaaga ccccgtggac 20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gacggagaga ccccgtggac 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gtccacgggg tcttcccggc 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gtccacgggg tctctccggc 20

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90

-continued

```
gaggagaagt ctgccgttac ctcctcttca gacggcaatg                          40


<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91

gaggagaagt ctgccattac ctcctcttca gacggcaatg                          40


<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92

gaggagaagt ctgccgttac ctcctcttca gacggcaatg                          40


<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93

gaggagaagt ctgccgttac cacctattca gacggcaatg                          40
```

METHOD AND KIT FOR DETECTION OF POLYNUCLEOTIDE

CROSS-REFERENCE TO RELATED APPLICATIONS

This is a national phase application that is based on and claims the benefit of International Application No. PCT/IN2020/050993, filed on Jan. 12, 2020, which is based on and claims the benefit under Indian Patent Application No. 201911049432 filed on Dec. 2, 2019, and Indian Patent Application No. 202011013418, filed on Mar. 27, 2020, the contents of each of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Dec. 10, 2025, is named 134839-00151_SL.txt and is 72,524 bytes in size.

FIELD OF INVENTION

The present invention relates to a kit for detection of a target polynucleotide using a CRISPR effector system comprising a CAS9 protein from *Francisella novicida*, and a single guide RNA. The present invention also relates to a method for detection of target polynucleotide.

BACKGROUND OF THE INVENTION

A large number of pathogenic diseases in humans are either caused by or associated with nucleic acid variations. Detecting these variations with high precision can allow disease diagnosis, suitable healthcare interventions and prediction of disease outcome. Additionally, they also find use in molecular biology applications. In the past, several methods have been described that can detect nucleic acid variations with varying degrees of efficacy in terms of speed, accuracy, complexity and cost [Li, Y., Li, S., Wang, J. & Liu, G. CRISPR/Cas Systems towards Next-Generation Biosensing. Trends in Biotechnology (2019); Terns, M. P. CRISPR-Based Technologies: Impact of RNA-Targeting Systems. Biesecker, L. G. & Green, R. C. Diagnostic clinical genome and exome sequencing. N. Engl. J. Med. (2014); Nayak, S., Blumenfeld, N. R., Laksanasopin, T. & Sia, S. K. Point-of-Care Diagnostics: Recent Developments in a Connected Age. Analytical Chemistry (2017)].

Further, emergence of diseases caused by novel pathogenic organisms also creates a need for a method of detecting the pathogenic organisms with high specificity. 2019 Novel Coronavirus (2019-nCoV or SARS-CoV-2) is such a virus recently identified as the cause of an outbreak of respiratory illness (Coronavirus disease 2019, COVID-19) with an increasing number of patients with severe symptoms and deaths. To monitor the presence of SARS-CoV-2 and to prevent its spread, it is highly important to detect infection as early and as fast as possible with a sensitive, reliable test, not only in the clinic, but also in remote locations, without the need for laboratory equipment.

While most of the low-cost techniques require critical design parameters and suffer from poor sensitivity and specificity issues, the more precise sequencing-based detection platforms often require significant time to assemble in addition to being unsuitable for large scale point-of-care (POC) applications due to costs for instrumentation and diagnostic experimentation. Currently, the available method for detecting the presence of the coronavirus in a sample is through quantitative or semi quantitative reverse transcription polymerase chain reaction (RT PCR). Although such a method is widely used and has proven effective for disease diagnosis, it suffers from limitations including need for specialized equipment, trained workforce, and operational costs.

Based on the method available in the art, there is a need for a method for detection of pathogenic nucleotides that is selective, sensitive, reliable, and easily integrated in different settings around the world. Such a test must be simple, cost-effective, portable, able to be mass-produced, and easy to use in low resource settings so that vital clinical decisions can be made in a significantly short period of time.

Clustered regularly interspaced short palindromic repeats (CRISPR)/CRISPR-associated (Cas) were originally discovered to act as immunity defense mechanisms against foreign pathogens in prokaryotic cells (Mojica et al. (2005) J. of Molecular Evolution 60:174-182). Cas9, a protein for the type II CRISPR/Cas system, was found to exhibit DNA cleavage activity. The nuclease activity of Cas9 can be guided by a CRISPR RNA complementary to a targeted sequence of DNA in the genome and a trans-activating CRISPR RNA that forms a complex with Cas9 (Jinek et al. (2012) Science 337:816-821). The CRISPR/Cas system has been modified for diagnosis of diseases. However, systems and methods known in art fail to provide the activity and specificity necessary for the purpose of confirmed diagnosis. The Cas9 from *Streptococcus pyogenes* shows variable levels of off targeting due to tolerance of mismatches predominantly in the "nonseed" region in the sgRNA, wherever these are encountered in the genome (P. D. Hsu et al., DNA targeting specificity of RNA-guided Cas9 nucleases. Nat. Biotechnology 31, 827-832 (2013). These off targeting due to tolerance of mismatch leads to misdiagnosis, specifically in case of genetic diseases caused by single point mutation. Therefore, there is a need in the art for an improved CRISPR/Cas system having very low tolerance for mismatch for confirming diagnosis of disease.

OBJECTIVES OF THE INVENTION

An objective of the present invention is to provide a kit for detection of a target polynucleotide using a CRISPR effector system comprising a CAS9 protein from *Francisella novicida*, and a single single guide RNA.

Another objective of the present invention is to provide a kit for detection of a single nucleotide variant of a polynucleotide using a CRISPR effector system comprising a CAS9 protein from *Francisella novicida*, and a single single guide RNA.

Yet another objective of the present invention is to provide a kit for detection of SARS-CoV2 using a CRISPR effector system comprising a CAS9 protein from *Francisella novicida*, and a single single guide RNA.

Still another objective of the present invention is to provide a method for detection of a target polynucleotide using the CRISPR system comprising a CAS9 protein and a single single guide RNA (sgRNA) that can specifically target nucleic acid molecules.

Yet another objective of the present invention is to utilize the method to distinguish between two nucleic acid molecules that are different by at least a single nucleotide.

Another objective of the present invention is to provide a method for detection of coronavirus using the CRISPR system comprising a CAS9 protein and a single single guide RNA (sgRNA).

Still another objective of the invention is to use the kit as a point of care (POC) application for quick detection of target polynucleotide from patient samples.

SUMMARY OF INVENTION

Accordingly, the present invention provides a kit for detection of a target polynucleotide comprising of a. Reverse and forward primers;
b. dNTPS;
c. PCR buffer;
d. DNA polymerase;
e. FnCas9 protein having SEQ ID NO. 2;
f. single guide RNA;
g. CRISPR-CAS9 Reaction buffer.

In an embodiment of the invention it provides a kit, wherein the single guide RNA is having sequence selected from the group consisting of SEQ ID NOS. 32, 33, 36, 39, 42, 45, 48, 51-64, 67, 76, 77, 79, 80.

In an embodiment of the invention it provides a kit, wherein the primers are selected from the sequences comprising of sequences having SEQ ID NOS. 37, 38, 40, 41, 43, 44, 46, 47, 49, 50, 65, 66, 68, 69.

In an embodiment of the invention it provides a kit, wherein the PCR buffer for Recombinase polymerase amplification comprises RPA Rehydration buffer and Magnesium Acetate.

In an embodiment of the invention it provides a kit, wherein the kit optionally comprises reverse transcriptase.

In an embodiment of the invention it provides a kit, wherein the reaction buffer comprises of buffers selected from the group comprising of HEPES, KCl, DTT, glycerol and $MgCl_2$.

In an embodiment of the invention it provides a kit, wherein the primers are labelled with biotin.

In an embodiment of the invention it provides a kit, wherein the FnCas9 protein complexed with a single guide RNA is labelled with a chemical group including, but not limited to, Fluorescein Amidite (FAM).

In an embodiment of the invention it provides a kit, wherein the cas9 protein is isolated from *Francisella novicida.*

In an embodiment of the invention it provides a kit, wherein the Fncas9 protein with a fluorophore tag is having SEQ ID NO: 3.

In an embodiment of the invention it provides a kit, wherein the kit optionally comprises a reaction tube, a dipstick buffer and a paper strip.

In an embodiment of the invention it provides a kit, wherein the dipstick buffer is Tris buffered saline.

In an embodiment of the invention it provides a kit, wherein the paper strip is made of nitrocellulose membrane coated with biotin-ligand and polyclonal (goat) digoxigenin antibody or polyclonal (rabbit) anti-FITC antibody in gold conjugate.

In an embodiment of the invention it provides a kit, wherein the method for detection of a target polynucleotide comprising:

(a) isolating a polynucleotide;
(b) providing FnCas9 protein with single guide RNA;
(c) providing primers having sequence selected from the group consisting of SEQ ID NOS. 37, 38, 40, 41, 43, 44, 46, 47, 49, 50, 65, 66, 68, 69;
(d) amplifying the isolated polynucleotide of step (a) using Recombinase Polymerase Amplification or PCR with forward and reverse primers obtained in step (c)to obtain a product;
(e) incubating the product obtained in step (d) with a FnCas9 ribonucleoprotein complex obtained in step (b) in a reaction tube comprising a reaction buffer for a time period in the range of 10 to 20 minutes at a temperature in the range of 35 to 37° C.; and
(f) visualizing the results obtained in step (e) by a method selected from the group consisting of agarose gel electrophoresis, lateral flow detection and Fluorescence detection.

In an embodiment of the invention it provides a kit, wherein the target polynucleotide is a DNA or a RNA.

In an embodiment of the invention it provides a kit, wherein the target polynucleotide is a pathogenic or non-pathogenic DNA or RNA.

In an embodiment of the invention it provides a kit, wherein the target polynucleotide is a SARS-COV2.

In an embodiment of the invention it provides a kit, wherein the target polynucleotide is a single nucleotide variant related to a disease selected from the group consisting of, but not limited to, sickle cell anemia, Glanzmann's Thrombasthenia, Glycogen Storage Disease Type I, Hemophilia A, X-linked myotubular myopathy.

In an embodiment of the invention it provides a kit, wherein the optionally Reverse transcription is carried out after step (a) when the polynucleotide is RNA.

In an embodiment of the invention it provides a kit, wherein the FnCas9 protein is isolated from *Francisella novicida* having SEQ ID NO: 2 and 3.

In an embodiment of the invention it provides a kit, wherein the single guide RNA has two parts having SEQ ID NO. 70 and 71.

In an embodiment of the invention it provides a kit, wherein the single guide RNA is having sequence selected from the group consisting of SEQ ID NOS. 32, 33, 36, 39, 42, 45, 48, 51-64, 67, 76, 77, 79, 80.

In an embodiment of the invention it provides a kit, wherein the method of lateral flow detection comprises, a) adding a paper strip and dipstick buffer to the reaction tube after step 14(c); and
b) incubating the tube obtained in step (a) for a period in the range of 5 to 10 minutes to observe a visible band on the paper strip, wherein the presence of the band on the paper strip confirms the presence of target polynucleotide.

In an embodiment of the invention it provides a kit, wherein the FnCas9 ribonucleoprotein complex comprising a cas9 protein from *Francisella novicida* having the amino acid sequence as set forth in SEQ ID NO.: 2, and a single guide RNA having SEQ ID NO. 79.

In an embodiment of the invention it provides a kit, wherein the single guide RNA or its corresponding sequence is selected from the group consisting of SEQ ID NOS.: 5, 6, 8, 9, 11, 12, 14, 15, 17, 18, 19-36, 39, 42, 45, 48, 76, 77, 79, 80.

In an embodiment of the invention it provides a kit, wherein the corresponding DNA targeting region in SARS-CoV2 has a sequence as set forth in SEQ ID NO.: 64, 67.

In an embodiment of the invention it provides a kit, wherein the system for detecting diseases caused by single nucleotide variants (SNVs) wherein the system consisting of:

a. Cas 9 effector protein;
b. Sg RNA;

c. PCR primers for amplification of a target;

d. Reverse transcriptase if the sequence is an RNA sequence and amplification enzymes like a Taq polymerase;

e. Lateral flow assay strip with its buffer.

In an embodiment of the invention it provides a kit, wherein the single guide RNA is selected from the group consisting of SEQ ID NOS 5, 6, 8, 9, 11, 12, 14, 15, 17, 18, 19-36, 39, 42, 45, 48, 64, 67, 76, 77, 79, 80.

In an embodiment of the invention it provides a kit, wherein the primers are selected from the group consisting of SEQ ID NOS. 37, 38, 40, 41, 43, 44, 46, 47, 49, 50, 65, 66, 68, 69.

In an embodiment of the invention it provides a kit, wherein the Cas9 protein is isolated from *Francisella novicida*.

In an embodiment of the invention it provides a kit, wherein the Cas9 protein is fluorescent labeled.

In an embodiment of the invention it provides a kit, wherein the target nucleic acid is selected from DNA and RNA having SEQ ID NOS. 4, 7, 10, 13, 16.

In an embodiment of the invention it provides use of the system for detecting diseases selected from the group comprising of Genetic disorders like sickle cell anemia, Glanzmann's Thrombasthenia, Glycogen Storage Disease Type I, Hemophilia A, X-linked myotubular myopathy and Pathogenic diseases caused by microbes selected from the group comprising of SARS-CoV2, SARS CoV1, *Helicobacter pylori* infection.

BRIEF DESCRIPTION OF THE DRAWINGS

FIG. 13. CAS9 based discrimination of sickle cell anemia variant in DNA II.

FIG. 14. Gel based detection of Heterozygous SNPs in DNA.

FIG. 41. Representative gel images showing successful cleavage of substrates at different temperatures (10° C.-50° C.).

FIG. 42. Representative image of a substrate cleavage reaction using FnCAS9 RNP complex. Complete match to intended substrate (COVID-19) produces cleavage of bound substrate (3 kb) to distinct signatures of 2.2 kb and 0.9 kb. Two different sgRNA forms (dual or single) produce similar readouts. ON represents specific sgRNAs while OFF represents non-specific sgRNAs. HBB (human haemoglobin locus targeting sgRNAs) is used as a positive control. Control represents substrate without RNP and is not cleaved.

BRIEF DESCRIPTION OF SEQUENCE LISTING

Figure 1:
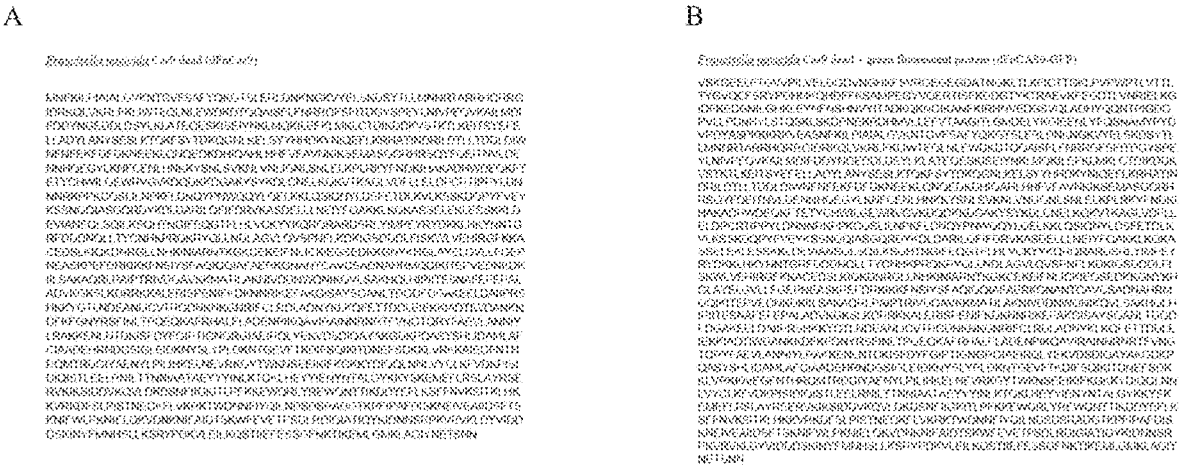
FIG. 1. Protein sequence of dead FnCas9 (A) and dFnCas9-GFP (B).

1. SEQ ID NO.1—Protein sequence of recombinant FnCas9 from *Francisella novicida.*
2. SEQ ID NO.2—Protein sequence of recombinant dead FnCas9 (dFnCas9) from *Francisella novicida.*
3. SEQ ID NO.3—Protein sequence of recombinant dFn-Cas 9 from *Francisella novicida* coupled with green Fluorescent protein.
4. SEQ ID NO.4—synthetic DNA containing portion of human gene encoding for Glycogen storage disease type I.
5. SEQ ID NO. 5—Synthetic DNA for SgRNA seq.1 against Glycogen storage disease type I.
6. SEQ ID NO 0.6—Synthetic DNA for SgRNA seq.2 against Glycogen storage disease type I.
7. SEQ ID NO.7—Synthetic DNA containing portion of human gene encoding for Glanzmann thrombasthenia.
8. SEQ ID NO.8—Synthetic DNA for SgRNA seq.1 against Glanzmann thrombasthenia.
9. SEQ ID NO.9—Synthetic DNA for SgRNA seq.2 against Glanzmann thrombasthenia.
10. SEQ ID NO.10—Synthetic DNA containing portion of human gene encoding for X-linked myotubular myopathy.
11. SEQ ID NO.11—Synthetic DNA for SgRNA seq.1 against X-linked myotubular myopathy.
12. SEQ ID NO.12—Synthetic DNA for SgRNA seq.2 against X-linked myotubular myopathy.
13. SEQ ID NO.13—Synthetic DNA containing portion of human gene encoding for Hereditary Factor VIII deficiency disease (HA).
14. SEQ ID NO.14—Synthetic DNA for SgRNA seq 1 against Hereditary factor VIII deficiency disease (HA).
15. SEQ ID NO.15—Synthetic DNA for SgRNA seq 2 against Hereditary factor VIII deficiency disease (HA).
16. SEQ ID NO.16—Synthetic DNA containing portion of human gene encoding for Sickle Cell Anemia.
17. SEQ ID NO.17—Synthetic DNA for SgRNA seq.1 against Sickle cell Anemia (SCA).
18. SEQ ID NO.18—Synthetic DNA for SgRNA seq.2 against Sickle cell Anemia (SCA).
19. SEQ ID NO.19—Synthetic DNA for double mismatch at HBB locus 1.
20. SEQ ID NO.20—Synthetic DNA for double mismatch at HBB locus 2.
21. SEQ ID NO.21—Synthetic DNA for double mismatch at HBB locus 3.
22. SEQ ID NO.22—Synthetic DNA for double mismatch at HBB locus 4.
23. SEQ ID NO.23—Synthetic DNA for double mismatch at HBB locus 5.
24. SEQ ID NO.24—Synthetic DNA for double mismatch at HBB locus 6.
25. SEQ ID NO.25—Synthetic DNA for double mismatch at HBB locus 7.
26. SEQ ID NO.26—Synthetic DNA for double mismatch at HBB locus 8.

27. SEQ ID NO.27—Synthetic DNA for double mismatch at HBB locus 9.
28. SEQ ID NO.28—Synthetic DNA for double mismatch at HBB locus 10.
29. SEQ ID NO.29—Synthetic DNA for double mismatch at HBB locus 11.
30. SEQ ID NO.30—Synthetic DNA for double mismatch at HBB locus 12.
31. SEQ ID NO.31—Synthetic DNA for double mismatch at HBB locus 13.
32. SEQ ID NO.32—Synthetic WT SgRNA Sequence for human HBB locus.
33. SEQ ID NO.33—Synthetic WT SgRNA Sequence with mismatches at PAM proximal 2 and 6 positions.
34. SEQ ID NO.34—Synthetic DNA sequence for HBB mismatched target 1.
35. SEQ ID NO.35—Synthetic DNA sequence for HBB mismatched target 2.
36. SEQ ID NO.36—SgRNA with 1 mismatch for Glycogen Storage disease type I SNV and 2 mismatch for wild type sequence at $6^{th}$ and $2^{nd}$ position.
37. SEQ ID NO.37— PCR Primer for Glycogen storage disease type I.
38. SEQ ID NO.38—PCR Primer for Glycogen storage disease type I.
39. SEQ ID NO. 39—SgRNA with 1 mismatch for Glanzmann Thrombasthenia SNV and 2 mismatch for wild type sequence at 6th and $2^{nd}$ position.
40. SEQ ID NO.40—PCR Primer for Glanzmann thrombasthenia disease.
41. SEQ ID NO.41—PCR Primer for Glanzmann thrombasthenia disease.
42. SEQ ID NO.42—SgRNA with mismatch for X-linked myotubular myopathy SNV and 2 mismatch for wild type sequence at $6^{th}$ and $2^{nd}$ position.
43. SEQ ID NO 0.43—PCR Primer for X-linked myotubular myopathy disease.
44. SEQ ID NO 0.44—PCR Primer for X-linked myotubular myopathy disease.
45. SEQ ID NO.45—SgRNA with 1 mismatch for Hemophilia A(Factor VIII) deficiency SNV and 2 mismatch for wild type sequence at $6^{th}$ and $2^{nd}$ position.
46. SEQ ID NO.46—PCR Primer for hereditary Factor VIII deficiency disease.
47. SEQ ID NO.47—PCR Primer for hereditary Factor VIII deficiency disease.
48. SEQ ID NO.48—SgRNA sequence for IVC against plasmid containing HBB sequence.
49. SEQ ID NO.49—PCR Primer for 228 bp HBB locus amplicon.
50. SEQ ID NO.50—PCR Primer for 228 bp HBB locus amplicon.
51. SEQ ID NO.51—SgRNA with 2 mismatches with respect to HBB locus SgRNA keeping mismatch at $2^{nd}$ and $3^{rd}$ position of SgRNA.
52. SEQ ID NO.52—SgRNA with 2 mismatches with respect to HBB locus SgRNA keeping mismatch at $2^{nd}$ and $4^{th}$ position of SgRNA.
53. SEQ ID NO.53—SgRNA with 2 mismatches with respect to HBB locus SgRNA keeping mismatch at $2^{nd}$ and $5^{th}$ position of SgRNA.
54. SEQ ID NO.54—SgRNA with 2 mismatches with respect to HBB locus SgRNA keeping mismatch at $2^{nd}$ and $6^{th}$ position of SgRNA.
55. SEQ ID NO.55—SgRNA with 2 mismatches with respect to HBB locus SgRNA keeping mismatch at $2^{nd}$ and $7^{th}$ position of SgRNA.
56. SEQ ID NO.56—SgRNA with 2 mismatches with respect to HBB locus SgRNA keeping mismatch at $2^{nd}$ and $8^{th}$ position of SgRNA.
57. SEQ ID NO.57—SgRNA with 2 mismatches with respect to HBB locus SgRNA keeping mismatch at $2^{nd}$ and $9^{th}$ position of SgRNA.
58. SEQ ID NO.58—SgRNA with 2 mismatches with respect to HBB locus SgRNA keeping mismatch at $2^{nd}$ and $10^{th}$ position of SgRNA.
59. SEQ ID NO.59—SgRNA with 2 mismatches with respect to HBB locus SgRNA keeping mismatch at $2^{nd}$ and $15^{th}$ position of SgRNA.
60. SEQ ID NO.60—SgRNA with 2 mismatches with respect to HBB locus SgRNA keeping mismatch at $2^{nd}$ and $16^{th}$ position of SgRNA.
61. SEQ ID NO.61—SgRNA with 2 mismatches with respect to HBB locus SgRNA keeping mismatch at $2^{nd}$ and $17^{th}$ position of SgRNA.
62. SEQ ID NO.62—SgRNA with 2 mismatches with respect to HBB locus SgRNA keeping mismatch at $2^{nd}$ and $18^{th}$ position of SgRNA.
63. SEQ ID NO.63—SgRNA with 2 mismatches with respect to HBB locus SgRNA keeping mismatch at $2^{nd}$ and $19^{th}$ position of SgRNA.
64. SEQ ID NO.64—N gene crRNA sequence FELUDA.
65. SEQ ID NO.65—SARS_CoV2 N gene crRNA Forward primer oligo for IVT.
66. SEQ ID NO.66—SARS_CoV2 N gene crRNA reverse primer oligo for IVT.
67. SEQ ID NO.67—S gene crRNA sequence FELUDA.
68. SEQ ID NO.68—SARS_CoV2 S gene crRNA Forward primer oligo for IVT feluda.
69. SEQ ID NO.69—SARS_CoV2 S gene crRNA reverse primer oligo for IVT feluda.
70. SEQ ID NO.70—Synthetic chimeric single guide RNA part 1.
71. SEQ ID NO.71—Synthetic chimeric single guide RNA part 2.
72. SEQ ID NO.72—Modified chimeric single guide RNA part 1.
73. SEQ ID NO.73—Modified chimeric single guide RNA part 2.
74. SEQ ID NO.74—Nucleotide sequence for sgRNA.
75. SEQ ID NO.75—Nucleotide sequence for sgRNA.
76. SEQ ID NO.76—Representative sgRNA for HBB locus.
77. SEQ ID NO.77—Representative sgRNA for HBB locus.
78. SEQ ID NO.78—Representative sgRNA for SpCas9.
79. SEQ ID NO.79—Representative sgRNA for FnCas9.
80. SEQ ID NO.80—Generic sgRNA for FnCas9 with one mismatch.

ABBREVIATIONS USED

FELUDA: FNCAS9 Editor-Limited Uniform Detection Assay

DETAILED DESCRIPTION OF INVENTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

A "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type DNA" is DNA that is naturally occurring in or endogenous to the organism.

Also as used herein, the terms "nucleic acid," "nucleic acid molecule," and "polynucleotide" refer to RNA or DNA that is linear or branched, single or double stranded, or a hybrid thereof. The term also encompasses RNA/DNA hybrids.

"Cas9" refers to a large group of endonucleases that catalyze the double stranded DNA cleavage in the CRISPR Cas system.

The CRISPR-Cas system does not require the generation of customized proteins to target specific sequences but rather a single Cas enzyme can be programmed by a short RNA molecule to recognize a specific DNA target. An exemplary CRISPR complex comprises a CRISPR enzyme complexed with a guide sequence hybridized to a target sequence within the target polynucleotide. The present invention provides methods for using one or more elements of a CRISPR system. The CRISPR complex of the invention provides an effective means for disease diagnosis.

The CRISPR effector system of the present invention comprises an effector protein and a single guide RNA designed to bind to corresponding target molecules. The CRISPR effector system of the present invention is used for distinguishing two nucleic acid molecules that differ by at least one nucleotide in their respective sequences. The present invention also provides a CRISPR effector system for rapidly identifying the COVID-19 nucleotide sequence in a sample for early diagnosis and preventive measures for community transmission.

In an embodiment of the present invention, target RNAs and/or DNAs may be amplified prior to activating the CRISPR effector protein. Any suitable RNA or DNA amplification technique may be used. The techniques include but are not limited to non-isothermal amplification PCR, isothermal PCR, multiple displacement amplification (MDA), rolling circle amplification (RCA), ligase chain reaction (LCR), or ramification amplification method (RAM).

In a preferred embodiment of isothermal PCR, recombinase polymerase amplification (RPA) reaction is used to amplify the target nucleic acids. RPA reactions employ recombinases which are capable of pairing sequence-specific primers with homologous sequence in duplex DNA. If target DNA is present, DNA amplification is initiated and no other sample manipulation such as thermal cycling or chemical melting is required. The entire RPA amplification system is stable as a dried formulation and can be transported safely without refrigeration. RPA reactions may also be carried out at isothermal temperatures with an optimum reaction temperature of 37-42° C. The sequence specific primers are designed to amplify a sequence comprising the target nucleic acid sequence to be detected. RPA reactions can also be used to amplify target RNA. The target RNA is first converted to cDNA using a reverse transcriptase, followed by second strand DNA synthesis, at which point the RPA reaction proceeds as outlined above.

In an embodiment, the present invention provides a detection system for detection of a target polynucleotide comprising of a CRISPR effector protein, a sgRNA molecule targeting a polynucleotide sequence, reagents to amplify the polynucleotide and a fluorescent or colorimetric detection system. The system comprises reagents for nucleic acid amplification. These include a pair of long primers, one of which contains a promoter sequence for an RNA polymerase. The two primers can be annealed and extended in a PCR reaction followed by transcription for producing sgRNAs.

The detection system consists of a CAS9 protein and a sgRNA consisting of two parts: a crRNA region that recognizes target polynucleotide and a tracrRNA region that is required for CAS9 protein binding and recruitment to target polynucleotide. The CAS9 protein can be from *Francisella novicida* or any other bacteria that show little to no affinity with polynucleotide harboring mismatches between crRNA and target. In a preferred embodiment of the present invention, the CAS9 protein is from *Francisella novicida*. The CAS9 protein can be engineered for inactivating its cleavage properties and additionally carrying fluorescent or biochemical tags to enable detection or purification of ribonucleoprotein complex (RNP complex) associated/dissociated from polynucleotide.

The detection system may consist of one or more mismatches incorporated in the crRNA region of the sgRNA to distinguish between two target polynucleotide molecules. These mismatches may be incorporated at defined positions with respect to the protospacer adjacent motif (PAM) sequence on the polynucleotide. The detection system distinguishes between targets on the basis of the differences in binding affinities to the individual polynucleotides that are different by at least one nucleotide. The CRISPR effector complex binds matched polynucleotide very efficiently while showing minimal binding at targets containing at least one mismatched nucleotide. The starting material for obtaining a target polynucleotide for CRISPR effector mediated cleavage may be genomic DNA of a subject. The starting material for obtaining a target polynucleotide for CRISPR effector mediated cleavage is a circular DNA or linear DNA. In a preferred embodiment of the present invention, the target polynucleotide to be detected can be COVID-19 RNA converted into complementary DNA (cDNA) prior to being used as a substrate for amplification.

In another embodiment of the present invention, the target polynucleotide may be amplified by Polymerase Chain Reaction (PCR) using primers specific to the target region. In a preferred embodiment, the conversion of RNA to DNA can be done using a Reverse Transcription (RT) reaction using appropriate enzymes. In a preferred embodiment, the DNA or cDNA target can be amplified using isothermal amplification method Recombinant Polymerase Amplification (RPA) using specific primers that can amplify the target polynucleotide at a single temperature.

In still another embodiment of the present invention, a synthetic PAM site may be introduced in one of the PCR primers to facilitate the detection of single nucleotide variants (SNVs) that do not have an adjacent PAM. In a preferred embodiment, the RNA can be reverse transcribed to cDNA with a PAM containing reverse primer and then a PCR step can be performed on the DNA resulting in the amplicon that can be targeted by CRISPR components.

In another embodiment of the present invention, the target to be detected can be isolated from body fluids of an individual organism. The bodily fluids are selected from the group consisting of saliva, sputum, serum, plasma, blood, pharyngeal, nasal/nasal pharyngeal and sinus secretions, urine, mucous, gastric juices, pancreatic juices, bone marrow aspirates, cerebral spinal fluid, feces, semen, products of lactation or menstruation, cervical secretions, vaginal fluid, tears and lymph.

In an embodiment of the present invention, the primers used for amplification are biotin-labelled to enable downstream product purification using streptavidin. The polynucleotide amplified by PCR may be purified before subjected to CRISPR effector system mediated cleavage to ensure externally added components of the PCR reaction do not hamper the cleavage reaction.

In another embodiment of the present invention, the target polynucleotide cleavage or binding reactions using purified effector protein and sgRNA can occur within an hour. The detection system can cleave polynucleotide matching the crRNA sequence completely and not cleave polynucleotide that do not match the crRNA sequence completely leading to a visually distinct pattern of DNA products resolved by agarose gel electrophoresis. The agarose gel electrophoresis pattern of polynucleotide cleavage can rapidly determine the presence of an SNV in a target incubated with the CRISPR effector complex.

In still another embodiment the amplified polynucleotide can be incubated with the CRISPR effector complex and a readout based on interaction of the complex with the polynucleotide can be obtained. The CAS9 protein used can be active (intact nuclease domains) or inactive (mutated nuclease domains). If an intact CAS9 protein is used, the target polynucleotide will be cleaved, and a distinct agarose gel electrophoresis signature will be obtained for COVID-19 sequence. The electrophoresis signature will be different if assayed with a sequence other than COVID-19. If an inactive CAS9 protein is used, the target polynucleotide will be bound (but not cleaved) if an sgRNA containing a perfectly matched sequence is used while not bound if an sgRNA with mismatches is used. A control non-targeting sgRNA can give an alternate signature thereby distinguishing COVID-19 from a different viral strain.

In another embodiment of the present invention, the agarose gel electrophoresis may be substituted by a system that can analyze bio-fragments generating a distinguishable pattern read out on a detection device. The device for analyzing the bio-fragments can be portable and field-deployable. Further, the inactive CAS9 protein can be fluorescently labelled so that a fluorescent readout can be obtained after interaction with the target polynucleotide. The fluorescent label can be added to the tracrRNA part of the dual sgRNA. The fluorescence detection system can be adapted to a lateral flow device such as a paper strip for rapid detection of COVID-19 identity or single nucleotide variant causing genetic diseases. The paper strip system can give a distinct band upon accumulation of biotin tagged substrate on a streptavidin line.

In yet another embodiment, the detection can be through a fluorescence reader based on the binding of CAS9 RNP and an immobilized substrate complex. The detection can be fluorometric based on fluorescence emitted by CAS9-RNP upon association or dissociation with its target polynucleotide without the need for cleavage.

The detection system can be simplified into a point-of-care device for rapid genotyping from patient samples. The detection system can be optimized for discriminating both homozygous and heterozygous SNVs. The detection system can be optimized for identifying carriers of a disease mutation.

In an embodiment of the present invention, the detection system can use synthetic sgRNAs containing chemical modifications. The chemical modifications can improve the binding of the sgRNA to its substrate and improve the overall detection efficiency. The detection system can use engineered protein that gives a more robust readout due to enhanced properties of DNA interrogation. The detection system can be converted into a kit capable of multiplexed detection of target polynucleotide.

In another embodiment of the present invention, the detection system can be used to generate a rapid readout of multiple point mutations in a sample. The detection system can be used to distinguish DNA or RNA from strains of pathogenic microorganisms different by at least 1 nucleotide.

In another embodiment of the present invention, the detection system can be used to identify a nucleotide at a given position in a polynucleotide sequence. The identity can be generated by binding affinity of the CAS9-RNP complex with the polynucleotide with position specific modifications in the sgRNA.

In the method for detection of a target polynucleotide of the present invention, the target polynucleotide is a DNA or RNA. The target polynucleotide can be a pathogenic or non-pathogenic DNA or RNA. In the preferred embodiment of the present invention, the target polynucleotide is a COVID-19 RNA. In another preferred embodiment, the target polynucleotide is a single nucleotide variant related to a disease selected from the group consisting of, but not limited to, sickle cell anemia, Glanzmann's Thrombasthenia, Glycogen Storage Disease Type I, Hemophilia A, X-linked myotubular myopathy.

For the detection of a target polynucleotide, the polynucleotide is isolated from bodily fluids selected from the group consisting of saliva, sputum, serum, plasma, blood, pharyngeal, nasal/nasal pharyngeal and sinus secretions, urine, mucous, gastric juices, pancreatic juices, bone marrow aspirates, cerebral spinal fluid, feces, semen, products of lactation or menstruation, cervical secretions, vaginal fluid, tears and lymph. In the preferred embodiment, the bodily fluid is blood. In another preferred embodiment, the bodily fluid is nasal/nasal pharyngeal and sinus secretions.

In an embodiment of the present invention, there is provided a method for detection of a target polynucleotide, wherein optionally Reverse transcription is carried out before step (b) when the polynucleotide is an RNA.

In the method for detection of a target polynucleotide of the present invention, the FnCas9 ribonucleoprotein complex comprises a cas9 protein from *Francisella novicida*, a single single guide RNA (sgRNA), In the single single guide RNA (sg RNA), the crRNA is specific towards the target polynucleotide. Further, the tracrRNA can be labeled with a chemical modification selected from the group consisting of amidites, biotin, streptavidin or digoxigenin. In the method for detection of a target polynucleotide of the present invention, the cas9 protein is catalytically inactive having the amino acid sequence as set forth in SEQ ID NO.: 2.

The present invention also provides a FnCas9 ribonucleoprotein complex comprising a cas9 protein from *Francisella novicida* which is catalytically inactive having the amino acid sequence as set forth in SEQ ID NO.: 2, and a single single guide RNA (sg RNA).

Figure 10:
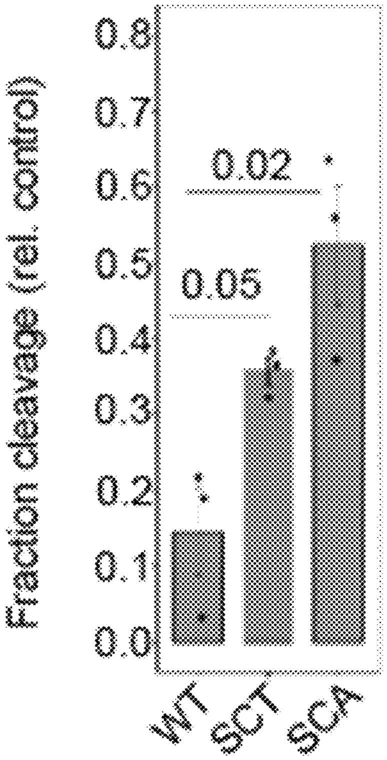
FIG. 10. Outcome of FELUDA on WT, SCT or SCA substrates. Error bars represent s.e.m (n=3 independent replicates, student t-test p values are shown).

An embodiment of the present invention is FELUDA (FNCAS9 Editor-Limited Uniform Detection Assay), wherein FELUDA accurately genotypes carriers of single nucleotide variants. Although sickle cell trait (SCT) individuals are generally non-symptomatic, carrier screening is vital to prevent the spread of SCA in successive generations and is widely employed in SCA control programs in various parts of the world. Since FELUDA outcomes are reflected by binding to substrate molecules, it resulted in clearly distinguishable signatures between the SCA, SCT and WT DNA obtained from patient's saliva samples (FIG. 10). FELUDA is able to identify all three genotypes with 100% accuracy and the results perfectly matched with Sanger sequencing data generated on the same samples.

Figure 15:
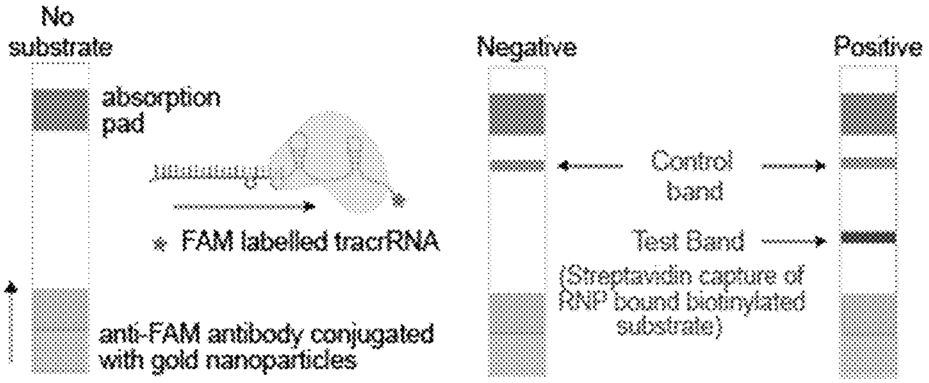
FIG. 15. Outline of lateral flow assay using FELUDA showing positions of control and test bands.
Figure 16:
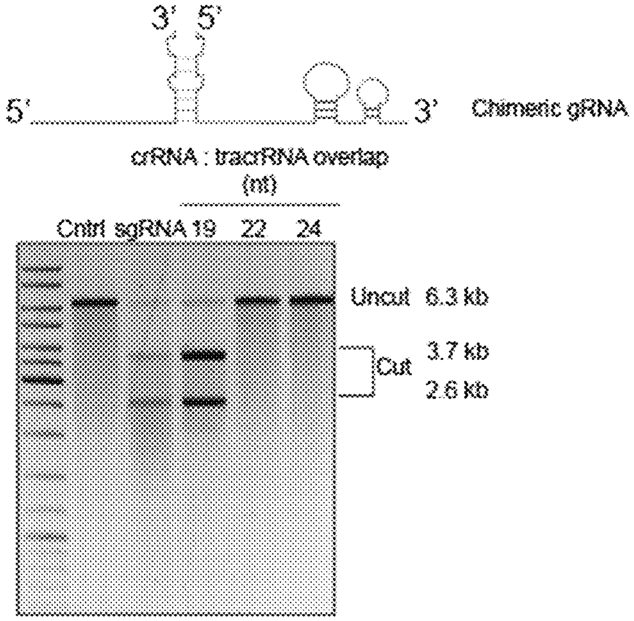
FIG. 16. Adaptation of chimeric gRNA for FELUDA. Cleavage outcomes with different lengths of overlap between crRNA and tracrRNA are shown.
Figure 17:
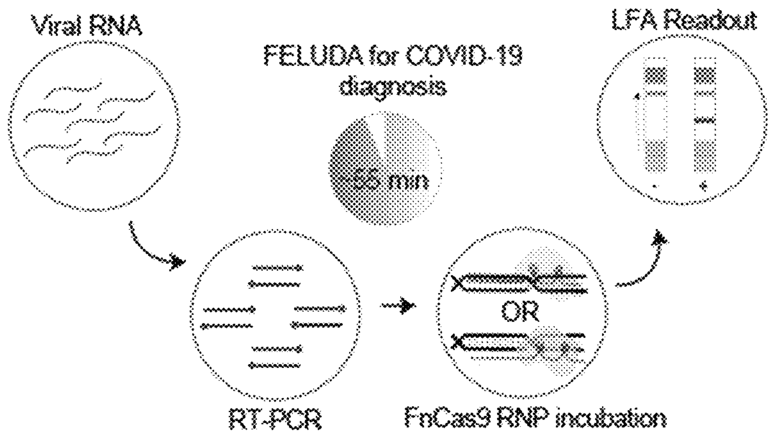
FIG. 17. Pipeline of FELUDA based detection for SARS-CoV-2 infection in samples obtained from patients. Individual steps are depicted.
Figure 18:
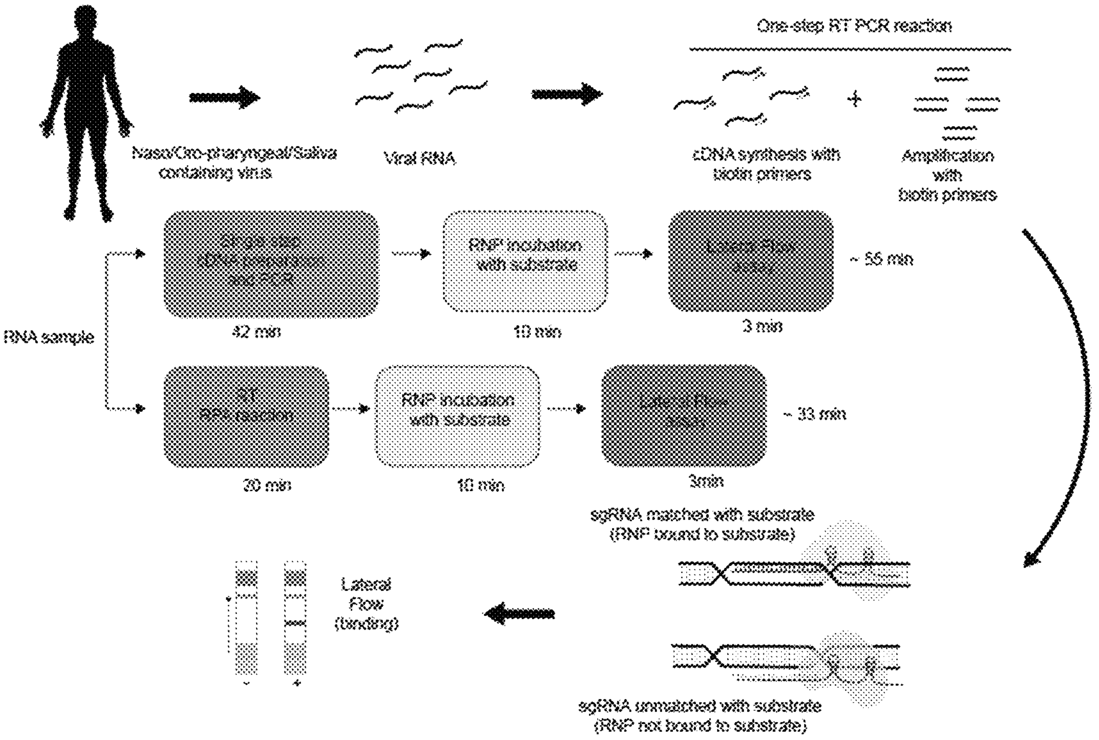
FIG. 18. FELUDA for COVID-19 diagnosis with time duration of individual steps are shown.
Figure 19:
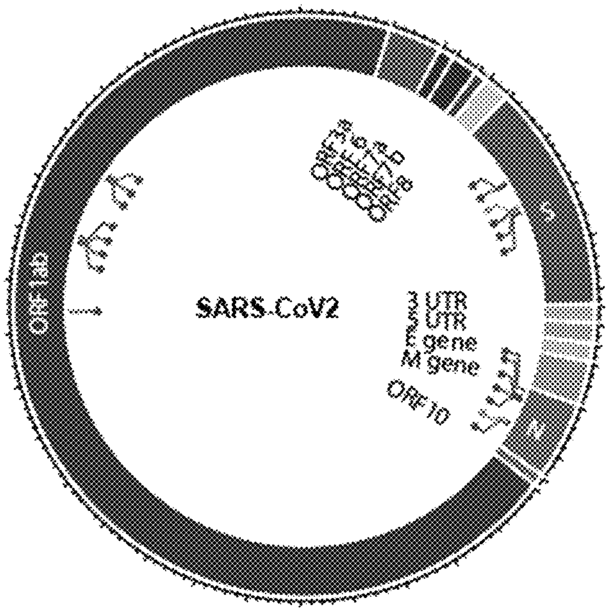
FIG. 19. Plot showing the regions of nCoV-2 RNA genome tested for FELUDA, successful regions represented in red.
Figure 20:
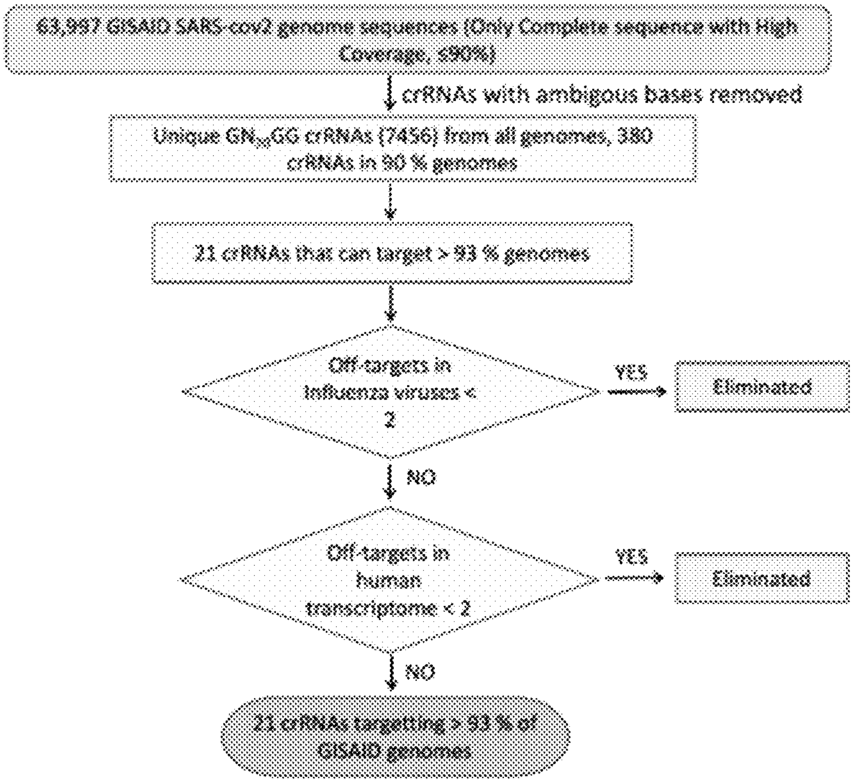
FIG. 20. sgRNA design strategy ensuring inclusivity of all known strains of SARS-CoV2 and no cross reactivity with other respiratory viruses like Influenza virus.
Figure 21:
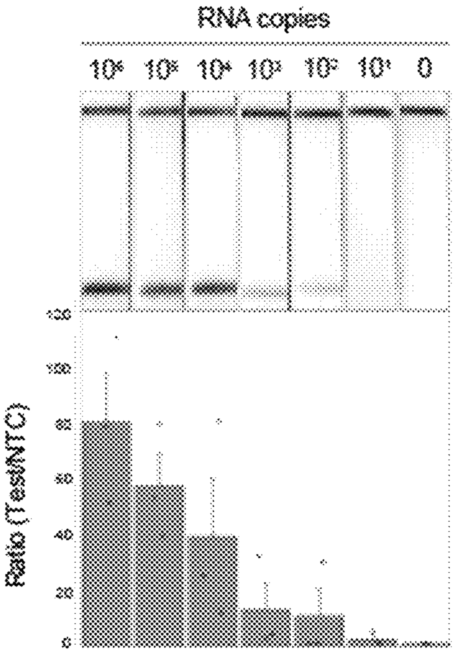
FIG. 21. LOD of FELUDA in purified target RNA. Top panel shows representative LFA readout on strips, bottom panel shows Fluorescent intensity ratios. Error bars s.e.m. (n=3 independent experiments).
Figure 22:
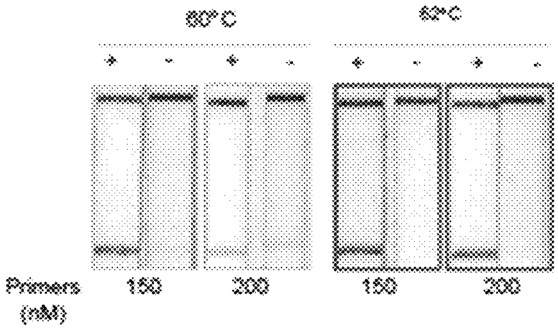
FIG. 22. Representative LFA strips showing optimized temperature and primer concentrations for FELUDA for COVID-19.
Figure 23:
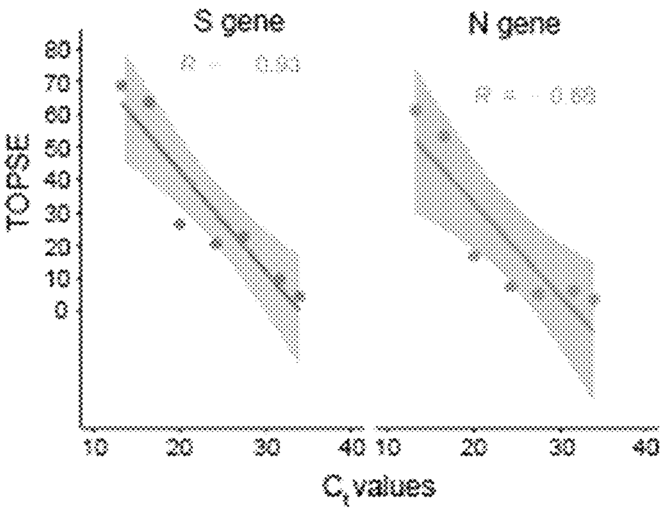
FIG. 23. Plot showing distribution of LFA intensities (y-axis) with dilution of patient RNA (Ct value, x-axis) for S gene and N gene. Correlation between the two are represented as R values.

In the embodiment, FELUDA is repurposed as a lateral flow assay (LFA) for the detection of SARS-CoV-2 that is low-cost, does not need complex instrumentation, and is highly accurate in diagnosis. To enable such a diagnosis on commercially available paper strips, the chemistry of capturing RNP-bound biotinylated substrate molecules is enabled on a distinct test line of the paper strip using FAM labeled chimeric gRNA (FIG. 15, FIG. 16). Using an optimized single step Reverse Transcription-PCR protocol followed by FELUDA, an assay has been developed that can detect SARS-CoV-2 sequences from RNA samples within an hour (FIG. 17 and FIG. 18). Up to 21 targets were tested across the SARS-CoV-2 RNA genome and identified two regions (in the viral N and S genes) which are present at high copy numbers and reported negligible number of mutations in publicly available datasets (63,997, GISAID submissions till Sep. 7, 2020) (FIG. 19, FIG. 20). Through extensive optimization of PCR and reaction components, FELUDA reached a limit of detection (LOD) of ~10 copies of purified viral sequence (FIG. 21, FIG. 22). Upon gradual dilution of patient RNA, both FELUDA and qRT-PCR was able to detect samples till the same dilution range (FIG. 23).

In the embodiment, FELUDA based detection can work robustly across a wide temperature range and up to 3 days post thawing of reaction components (at room temperature). Thus, field studies using FELUDA can be conducted in diverse climatic conditions and reaction components can be successfully used following cold chain transportation (FIG. 41).

EXAMPLES

The following examples are given by way of illustration and therefore should not be construed to limit the scope of the invention.

Example 1

CAS9 Protein and sgRNA Purification

The proteins used in the present invention were purified as reported in [Jinek, M. et al. A programmable dual-RNA-guided DNA endonuclease in adaptive bacterial immunity. *Science* (80) (2012)]. Briefly, plasmids for CAS9 from *Francisella novicida* were expressed in *Escherichia coli* Rosetta2 (DE3) (Novagen®). The protein expressing Rosetta2 (DE3) cells were cultured at 37° C. in LB medium (supplemented with 50 mg/l kanamycin) until $OD_{600}$ reached 0.6 and protein expression was induced by addition of 0.5 mM isopropyl β-D-thiogalactopyranoside (IPTG). The Rosetta2 (DE3) cells were further cultured at 18° C. overnight and harvested by centrifugation. The *E. coli* cells were resuspended in lysis buffer (20 mM Hepes, pH7.5, 250 mM NaCl, 5% glycerol, 1 mM DTT, 1 mM PMSF) supplemented with 1×PIC (Roche®), 100 ug/ml lysozyme and lysed by sonication and centrifuged. The lysate was affinity purified by Ni-NTA beads (Roche®) and the eluted protein (SEQ ID NO 1-3) was further purified by size-exclusion chromatography HiLoad® Superdex® 200 16/600 column (GE Healthcare™) in 20 mM HEPES pH 7.5, 150 mM KCl, 10% glycerol, 1 mM DTT, 10 mM $MgCl_2$. The concentrations of purified proteins were measured by Pierce BCA protein assay kit (Thermo Fisher Scientific©). The purified proteins were stored at −80° C. until further use.

Figure 2:
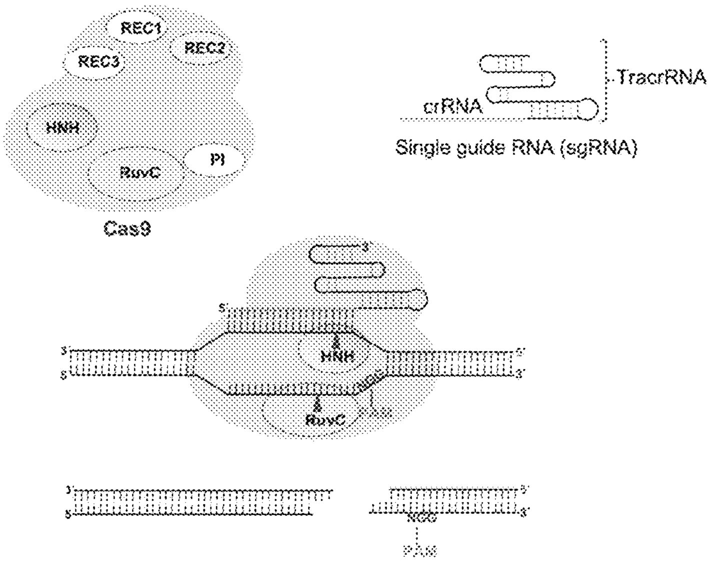
FIG. 2. Schematic showing components of a representative CAS9 Ribonucleoprotein complex.

In vitro transcribed sgRNA's were synthesized using MegaScript™ T7 Transcription kit's (Thermo Fisher Scientific®) using a T7 promoter containing template as substrates. IVT reactions were incubated overnight at 37° C. followed by NucAway spin column (Thermo Fisher Scientific®) purification. IVT sgRNAs were stored at −20° C. until further use. FIG. 2 shows the schematic representation of components of a representative CAS9 Ribonucleoprotein (RNP) complex.

Example 2

Figure 3:
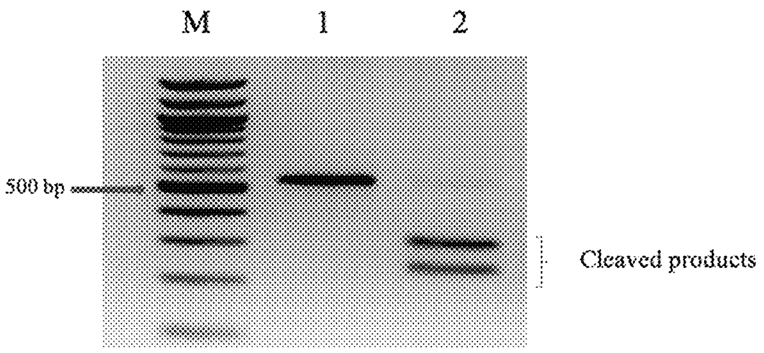
FIG. 3. In vitro cleavage of a target polynucleotide with CAS9.
Figure 4A:
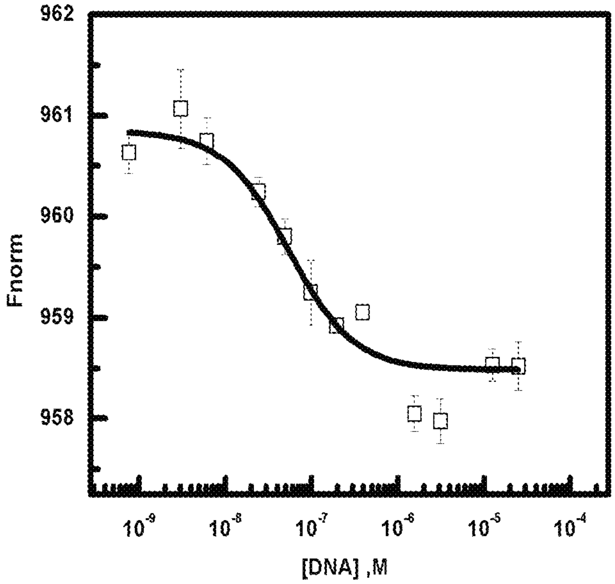
FIG. 4. (A-D) Binding affinity measurements of CAS9 with mismatched polynucleotide.
Figure 4B:
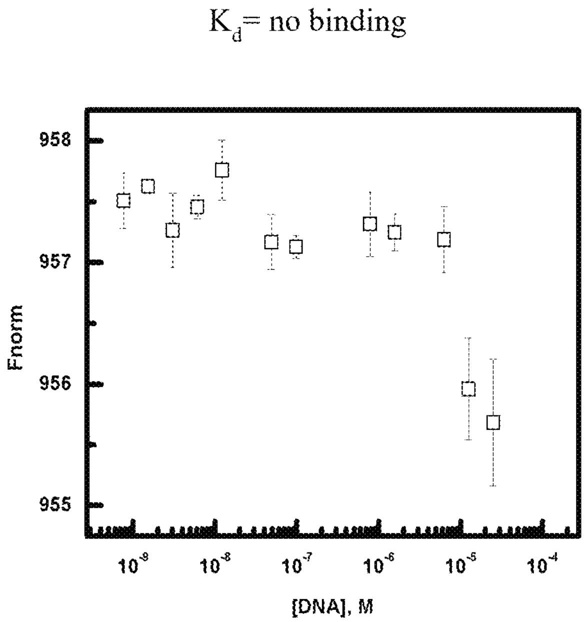
Figure 4C:
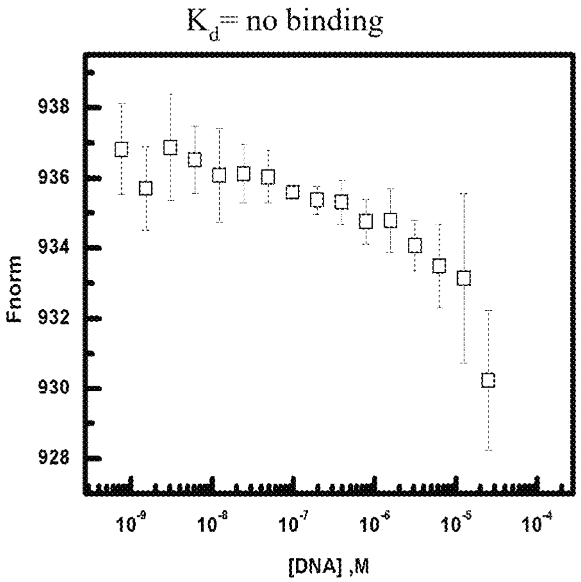
Figure 4D:
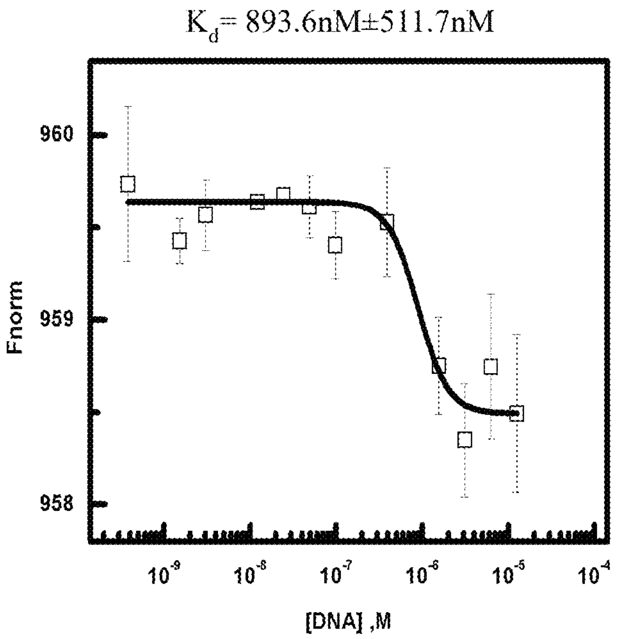

In Vitro Cleavage Reactions of Target with CAS9 RNP Complex 250 nM CAS9-sgRNA complex, (wherein the Cas9 could be one of the sequences in SEQ ID NO. 1-3, and a representative sgRNA sequence SEQ ID NO. 48) was reconstituted at 25° C. for 10 mins in reaction buffer (20 mM HEPES, pH7.5, 150 mM KCl, 1 mM DTT, 10% glycerol, 10 mM $MgCl_2$). 100 ng of PCR amplified substrate was incubated in reaction buffer with reconstituted RNP complex at 37° C. The reaction was then treated with 1 ul of 20 mg/ml Proteinase K in 15 ul reaction for 15 mins at 55° C. followed by the heat inactivation at 70° C. for 10 minutes. After then 1 ul of 20 mg/ml RNase treatment was given at 37° C. for 10 minutes, the reaction products were resolved in EtBr-stained 1.5% agarose gel, visualized by Syngene® Gel Doc. FIG. 3. shows In vitro cleavage of a target polynucleotide with CAS9 (SEQ ID NO. 1-3), which shows that FnCas9 can specifically identify and cleave DNA sequences that are targeted by sgRNA.

Example 3

Binding Affinity of a Representative CAS9 Complex (FnCAS9) with Target sgRNAs and Mismatched sgRNAs MST was performed as reported previously [Dong, D. et al. The crystal structure of Cpf1 in complex with CRISPR RNA. Nature (2016); Wienken, C. J., Baaske, P., Rothbauer, U., Braun, D. & Duhr, S. Protein-binding assays in biological liquids using microscale thermophoresis. Nat. Commun. (2010)]. Briefly, dFnCAS9-GFP (SEQ ID NO: 3) protein was complexed with PAGE purified respective IVT sgRNAs (purified by 12% Urea-PAGE). The binding affinities of the CAS9 proteins and sgRNA RNP complexes were calculated using Monolith NT. 115 (NanoTemper® Technologies GmbH, Munich, Germany). RNP complex (Protein:sgRNA molar ratio,1:1) was reconstituted at 25° C. for 10 mins in reaction buffer (20 mM HEPES, pH7.5, 150 mM KCl, 1 mM DTT, 10 mM $MgCl_2$). HPLC purified 30 bp dsDNA (IDT) of different genomic loci with varying concentrations (ranging from 0.09 nM to 30 μM) were incubated with RNP complex at 37° C. temperature for 30 min in reaction buffer. The sample was loaded into NanoTemper® standard treated capillaries and measurements were performed at 25° C. using 20% LED power and 40% MST power. Data analyses were done using NanoTemper® analysis software. FIG. 4 shows the binding affinity of FnCas9 with WT (SEQ ID NO: 32) and mismatched substrates (SEQ ID NO: 33-35). A low dissociation constant was seen for SEQ ID NO: 32 while, no binding was seen for SEQ ID NO: 33 and SEQ ID NO:34 and a very high dissociation constant for SEQ ID NO:35, thereby the presence of mismatches between sgRNA and target sequence abolishes binding of FnCas9, confirming its very high specificity.

Example 4

Figure 5:
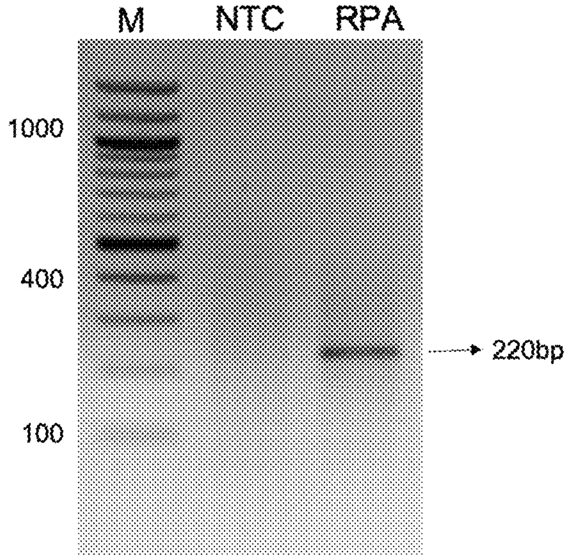
FIG. 5. Isothermal amplification of a target using Recombination Polymerase Amplification (RPA).

RPA for Amplifying Target and its Subsequent Cleavage Using FnCAS9 Complex 47.5 ul reaction mixes was reconstituted in 2.4 ul each of 10 uM stock of forward and reverse primers of Emxl gene, 29.5 ul of Primer Free Rehydration buffer (TwistAmp® Basic kit), 3-5 ng of genomic DNA and remaining reaction volume was made up by Nuclease Free Water. The reaction was added to a TwistAmp® Basic reaction (supplied with the TwistAmp® Basic kit) and mixed well. 2.5 ul of 280 mM Magnesium Acetate (MgOAc) was added to start the reaction. The reaction was then incubated at 39° C. for 20 minutes and then the amplicons were cleaned up by the Qiagen® PCR clean up kit. The amplicon was resolved in EtBr-stained 2.5% agarose gel, visualized by Syngene® Gel Documentation apparatus. FIG. 5 shows the Isothermal amplification of a target using Recombination Polymerase Amplification (RPA).

Figure 6:
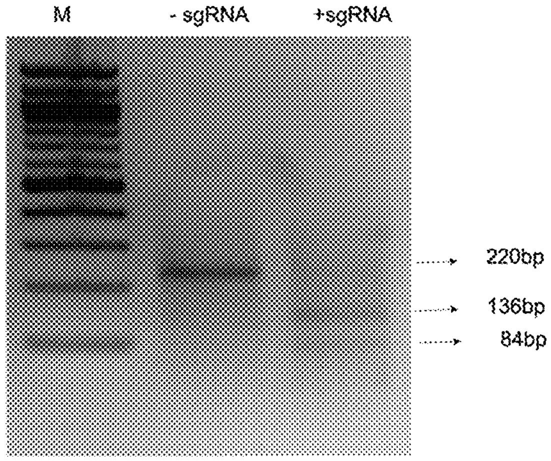
FIG. 6. In vitro cleavage of product obtained by RPA reaction.

250 nM CAS9-sgRNA complex was reconstituted at 25° C. for 10 mins in reaction buffer (20 mM HEPES, pH7.5, 150 mM KCl, 1 mM DTT, 10% glycerol, 10 mM $MgCl_2$). 100 ng of 220 bp EMX1 amplicon was incubated in reaction buffer with reconstituted RNP complex for 60 minutes at 37° C. The reaction was then treated with 1 ul of 20 mg/ml Proteinase K in 15 ul reaction for 15 mins at 55° C. followed by the heat inactivation at 70° C. for 10 minutes. After the 1 ul of 20 mg/ml RNase treatment at 37° C. for 10 minutes, the reaction products were resolved in EtBr-stained 2.5% agarose gel and visualized by Syngene® Gel Documentation apparatus. FIG. 6. In vitro cleavage of product obtained by RPA reaction, which confirms the activity of FnCas9 after RPA and maintains the specificity for binding and cleavage of target.

Example 5

Fluorescent Detection of Monogenic Variants

50 μL of Dynabeads™ MyOne™ Streptavidin C1 (Thermo Fisher Scientific®) were washed three times with 1 ml of buffer containing 50 mM TrisCl pH 7.5, 5 mM EDTA, 1M NaCl. 5 μL of the washed beads were incubated with 222 ng of 228 bp biotin labelled Hbb PCR amplicon (wild type and Sickle cell sample, SEQ ID NOs 49-50) for 30 minutes in 50 μL previously mentioned buffer. 200 nM (dFnCas9 GFP): 400 nM (sgRNA) RNP complex was reconstituted at 25° C. for 10 mins in 30 μL reaction buffer (20 mM HEPES, pH7.5, 150 mM KCl, 1 mM DTT, 10% glycerol, 10 mM MgCl2). 30 μL of the reconstituted RNP complex {200 nM (dFnCas9-GFP, SEQ ID NO. 3): 400 nM (sgRNA)} was incubated with the streptavidin beads bound with biotin labelled PCR amplicon for 20 minutes. Unbound dFnCas9 GFP emission spectra (495 nm-555 nm) were measured after 20 minutes incubation excitation at 408 nm.

Figure 7:
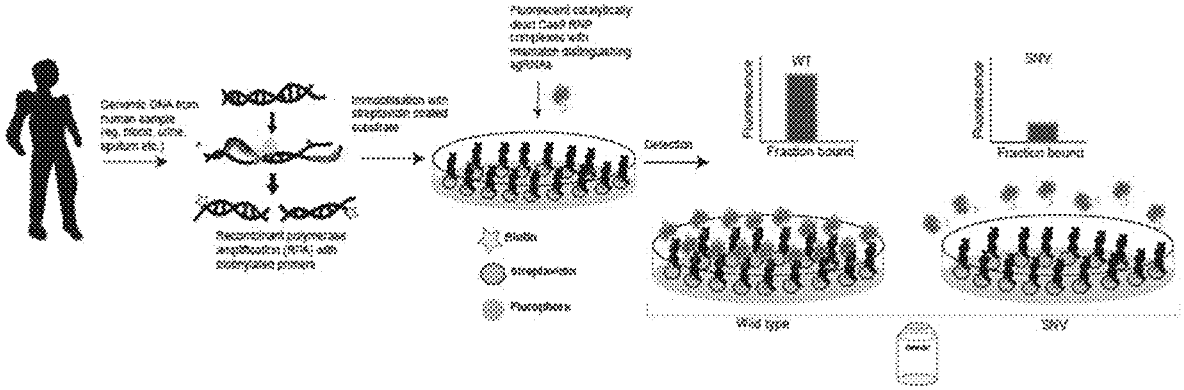
FIG. 7. Schematic showing the adaptation of the system for cleavage-free detection.
Figure 8:
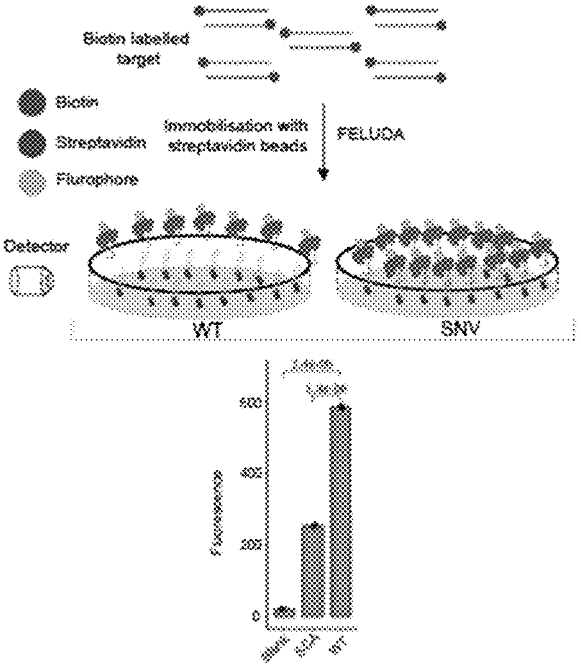
FIG. 8. Schematic for fluorescence-based detection of sickle cell anemia mutation using FELUDA. Error bars represent SD (3 independent experiments).
Figure 9:
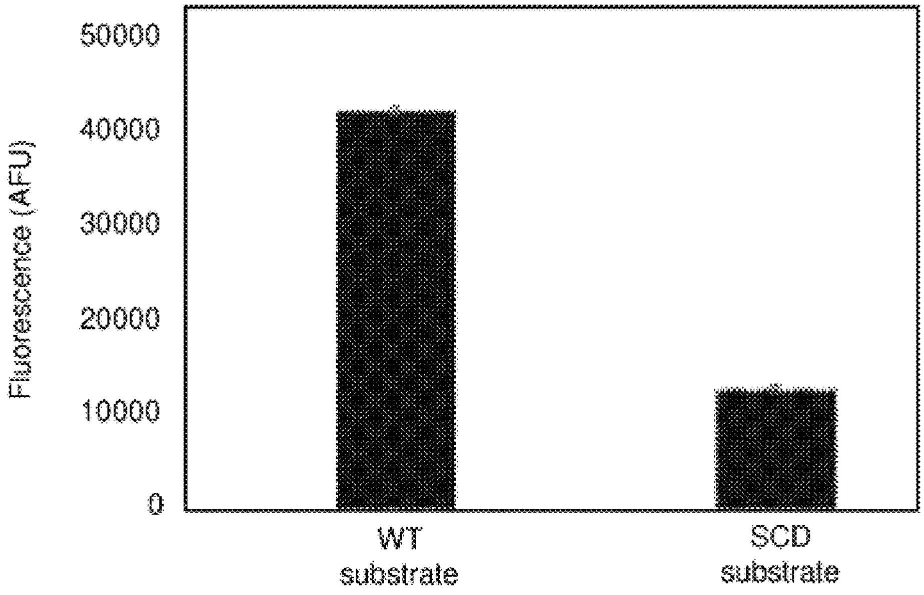
FIG. 9. Quantification of fluorescence readout for cleavage-free detection for WT and homozygous Sickle cell anemia mutation.

FIGS. 7 and 8 show the schematic representation showing the adaptation of the system for cleavage-free detection. FIG. 9 shows the quantification of fluorescence readout for cleavage-free detection for WT and homozygous Sickle cell anemia mutation. FnCas, thus could distinguish between the wt and scd substrates that have a single bp difference confirming the very high specificity of FnCas9, that can be measured using fluorescence values. It also demonstrated the successful binding-based detection of a single mismatch using FnCas9.

To enable robust readout and longer shelf-life, a chimeric sgRNA was developed in two parts with 19 nucleotide overlap (Part1 and Part 2 to be annealed to make full length sgRNA).

Part 1:

```
                                     (SEQ ID No: 70)
NNNNNNNNNNNNNNNNNNNNGUUUCAGUUGCUGAAUUAU
3'
```

Part 2:

```
                                     (SEQ ID NO: 71)
5'-GUAAUUAAUGCUCUGUAAUCAUUUAAAAGUAUU
UUGAACGGACCUCUGUUUGACACGUCUG
3'
```

N Corresponds to the Nucleotide Stretch in the Target. An Example is as Follows:

```
                                     (SEQ ID NO: 79)
5'-GGUCCACCAAACGUAAUGCGGUUUCAGUUGCUGAAUUAU-3'
```

The chimeric design performed similar to that of a full length sgRNA showing no loss of activity due to the split-sgRNA synthesis and also without any loss of specificity for 1 mismatch discrimination (FIG. 42).

Example 6

SCA FELUDA Detection Assay

Figure 11:
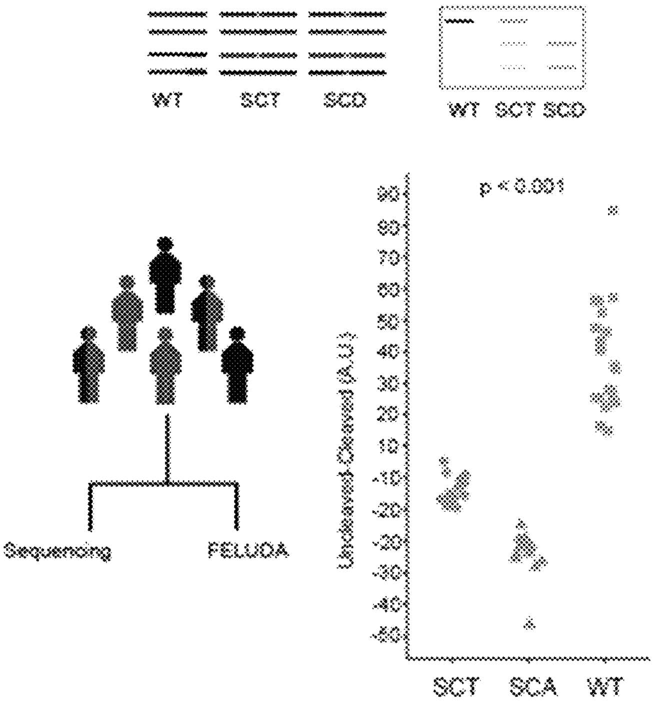
FIG. 11. Upper panel shows schematic of FELUDA for identifying carriers of SCA mutation. Lower panel shows blinded FELUDA results in a mixed cohort of individuals (n=49, one-way ANOVA p value is shown).

FELUDA accurately genotypes carriers of Mendelian variants. Although sickle cell trait (SCT) individuals are generally non-symptomatic, carrier screening is vital to prevent the spread of SCA (Sickle cell anemia) in successive generations and is widely employed in SCA control programs in various parts of the world. Since FELUDA outcomes are reflected by binding to substrate molecules, it resulted in clearly distinguishable signatures between the SCA, SCT and WT DNA obtained from patient's saliva samples (FIG. 10). To address the robustness of detecting the 3 genotype categories, a blinded experiment was performed using DNA obtained from 49 subjects with all three SCA genotypes from a CSIR-Sickle Cell Anaemia Mission Laboratory in Chhattisgarh, India. Remarkably, FELUDA identified all three genotypes with 100% accuracy and the results perfectly matched with Sanger sequencing data generated on same samples in a different laboratory (CSIR-Center for Cellular and Molecular Biology, Genome Research on Complex Diseases Lab) (FIG. 11).

Sequences containing WT, SCT and SCA were amplified using primers with/without 5' biotinylation from genomic DNA extracted from saliva or blood samples. Detection via In vitro Cleavage (IVC): DNA or RNA converted to DNA were PCR amplified to be used as a substrate in in vitro cleavage assay. ~100 ng of purified DNA amplicon was incubated in reaction buffer (20 mM HEPES, pH7.5, 150 mM KCl, 1 mM DTT, 10% glycerol, 10 mM MgCl2) along with reconstituted RNP complex (500 nM) at 37° C. for 30 minutes and cleaved products were visualized on agarose gel. Detection via Fluorescence Detection: DNA regions from Hbb locus (WT & SCA) were amplified using biotinylated primers. dFnCas9-GFP: sgRNA (180 nM:540 nM) RNP complex was reconstituted at 25° C. for 10 mins in reaction buffer (20 mM HEPES, pH7.5, 150 mM KCl, 1 mM DTT, 10% glycerol, 10 mM MgCl2). Meanwhile, 6 μL of the Dynabeads™ MyOne™ Streptavidin C1 (Thermo Fisher Scientific®) were prepared. Beads were incubated with 1 μM of biotinylated Hbb amplicon (WT & SCA) for 30 minutes in the reaction buffer. Further, dFnCas9-GFP RNP complex was incubated with the streptavidin bound PCR amplicon for 30 minutes. Emission spectra of unbound dFnCas9-GFP was measured using Monolith NT. 115 (NanoTemper® Technologies GmbH, Munich, Germany) under 60% excitation power in blue filter (465-490 nm excitation wavelength; 500-550 nm emission wavelength) with medium MST power.

Figure 12:
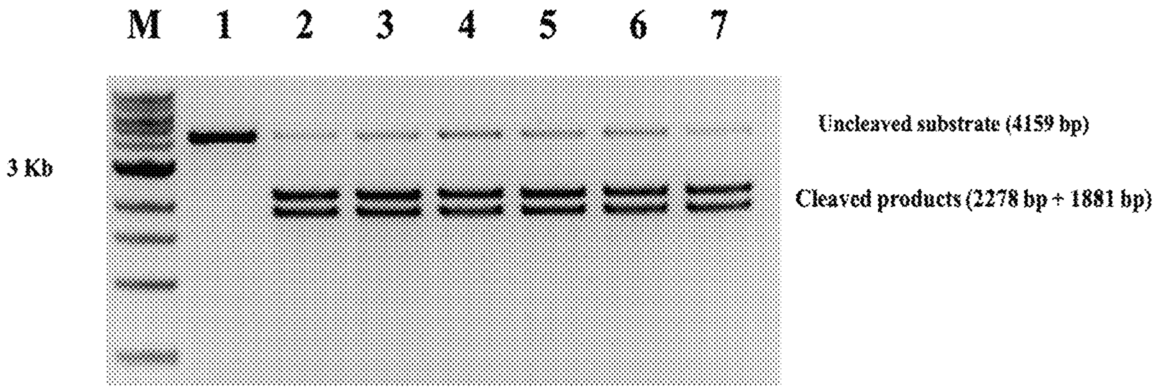
FIG. 12. CAS9 based discrimination of sickle cell anemia variant in DNA I.

CAS9 based detection of Sickle cell anemia SNP in amplified patient (versus control) DNA leads to characteristic cleavage pattern in case of mutation and absence in case of wild type DNA as provided in Figure. 12. CAS9 based discrimination of Sickle cell anemia SNP in amplified patient (versus control) DNA leads to cleavage pattern in case of wild type DNA and absence in case of sickle cell mutation as provided in FIG. 13. Gel based detection of Heterozygous SNPs in DNA can be seen in FIG. 14 (SEQ ID NOs. 16-18, 32).

Example 7

Lateral Flow Detection of COVID-19

FELUDA was sought to be repurposed as a lateral flow assay (LFA) for the detection of SARS-CoV-2 that is low-cost, does not need complex instrumentation, and is highly accurate in diagnosis. To enable such a diagnosis on commercially available paper strips, the chemistry of capturing RNP-bound biotinylated substrate molecules was enabled on a distinct test line of the paper strip using FAM labeled chimeric gRNA (FIG. 15, FIG. 16). Using an optimized single step Reverse Transcription-PCR protocol followed by FELUDA, an assay was developed that can detect SARS-CoV-2 sequences from RNA samples within an hour (FIG. 17 and FIG. 18). Up to 21 targets were tested across the SARS-CoV-2 RNA genome and identified two regions (in the viral N and S genes) which are present at high copy numbers and reported negligible number of mutations in publicly available datasets (63,997, GISAID submissions till Sep. 7, 2020) (FIG. 19, FIG. 20). Through careful optimization of PCR and reaction components, FELUDA reached a limit of detection (LOD) of ~10 copies of purified viral sequence (FIG. 21, FIG. 22). Upon gradual dilution of patient RNA, both FELUDA and qRT-PCR was able to detect samples till the same dilution range (FIG. 23). Since visual detection can occasionally have an operator-bias, particularly when the signal is very faint, a smartphone app TOPSE (True Outcome Predicted via Strip Evaluation) was developed to assist detection by returning a predictive score based on background correction.

Biotin Labelled Amplification of the substrate: Amplification of the COVID 19 polynucleotide with the biotin labelled primers by RPA (TwistDx™) or Thermal Cycler (Reverse transcription 50° C. for 15 minute, Initial denaturation 95° C. for 1 min, 5 Pre-amplification cycles of 95° C. for 5 sec; 60° C. for 40 sec followed by 40 amplification cycles of 95° C. for 5 sec; 60° C. for 40 sec) was carried out. After the confirmation of amplicon, PCR clean-up was done (Qiagen®) followed by quantification of the product. 4 μM of the COVID 19 specific crRNA along with the FnCas9 FAM labelled tracrRNA was reconstituted in a buffer containing 100 mM NaCl, 50 mM Tris HCl pH 8 and 1 mM MgCl2 by placing the reaction at room temperature for 15 mins followed by heating at 95° C. for 5 minutes. For binding of Cas9 complex to substrate, 500 nM of the chimeric FAM labelled sgRNA and inactive FnCas9 was reconstituted in a buffer (20 mM HEPES, pH7.5, 150 mM KCl, 1 mM DTT, 10% glycerol, 10 mM MgCl2) at 25° C. for 10 minutes. Following this, 2.2 nM of the PCR product was incubated with the RNP complex for 15 minutes at 37° C. in a reaction tube. Then, dipstick buffer was added in the reaction and the strips were added into the reaction tube. Gold nanoparticles are bound on the strip. Streptavidin is bound on the test line in the strip which captures the gold nanoparticle bound FELUDA complex. Visible bands can be visualised after 5-10 minutes of the incubation. Intensity of the bands gets darker with time.

Figure 24:
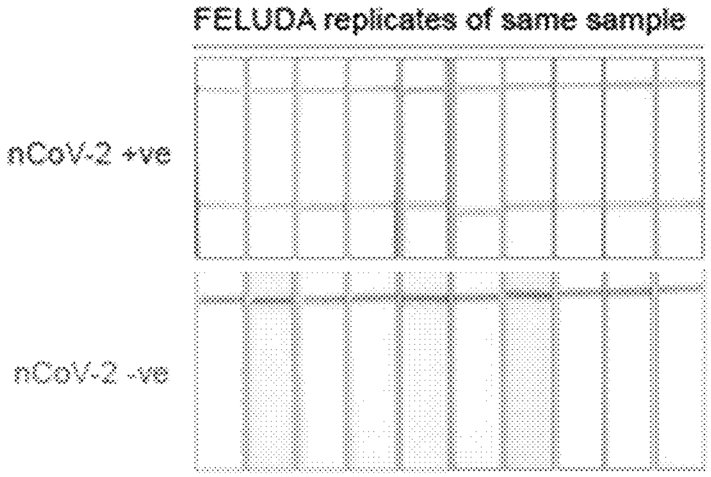
FIG. 24. Strong reproducibility between repeated FELUDA (RNP incubation and readout) on the same positive or negative sample is shown.

FIG. 15 shows the outline of lateral flow assay using FELUDA showing positions of control and test bands. FIG. 17 shows the pipeline of FELUDA based detection for SARS-CoV-2 infection in samples obtained from patients. Individual steps are depicted. FIG. 24 shows the strong reproducibility between repeated FELUDA (RNP incubation and readout) on the same positive or negative sample is shown. 10 replicates for SARS-CoV2 positive and negative samples are shown in this figure.

Example 8

FELUDA Limit of Detection (LOD)

Synthetic genomic Target for N gene was serially diluted (1:10, 7 times) from ~4×106 copies/μl to perform FELUDA reaction. Test band intensity was calculated using TOPSE app (Repeated in three independent experiments). FELUDA detection is semi-quantitative (due to stoichiometric binding of FnCas9 RNP: target) and therefore shows a strong negative correlation between Ct values and signal intensities (FIG. 21). This makes it uniquely placed among CRISPRDx platforms to accurately predict the viral load in patient samples with high reproducibility between assays. Through extensive optimization of PCR and reaction components, FELUDA reached a limit of detection (LOD) of ~10 copies of purified viral sequence (FIG. 22, 26). Upon gradual dilution of patient RNA, both FELUDA and qRT-PCR were able to detect samples till the same dilution range (FIG. 23).

Example 9

COVID-19 Detection Using 2 Gene FELUDA Assay

Figure 27:
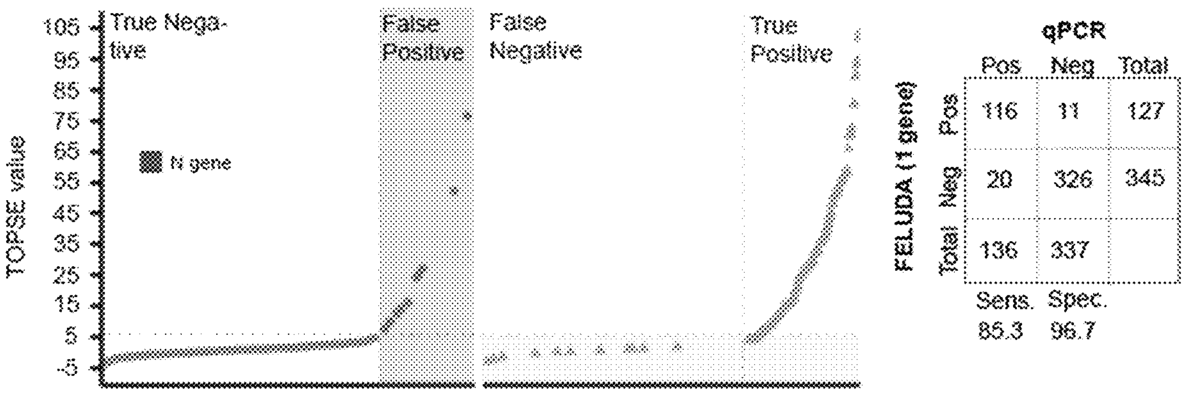
FIG. 27. One gene FELUDA on clinical samples (x axis) showing distribution of TOPSE values (y axis). Analyzed results represented on the right.
Figure 28:
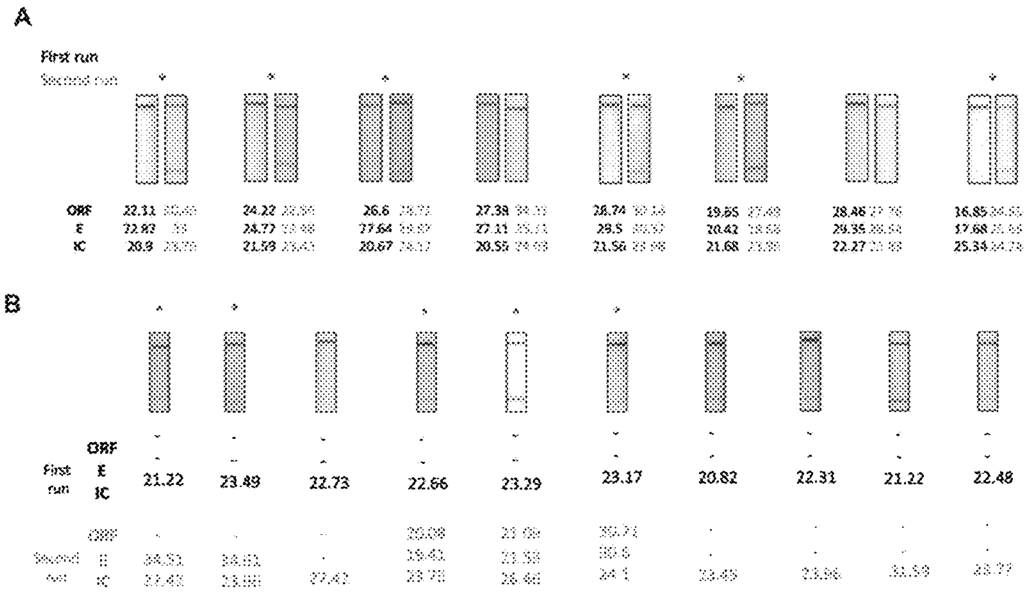
FIG. 28. Optimization of 2 gene FELUDA. (A) LFA readout of samples with a repeat FELUDA (N gene) and corresponding Ct values for E and ORF genes. IC, internal controls. Values in black and green are from $1^{st}$ run and $2^{nd}$ run respectively. Red asterisk denotes samples which became FELUDA positive on a repeat run. (B) Samples classified as negative in one qPCR run (shown in black) but showing $C_t$ values of E gene or E/ORF both genes on a second run (shown in green). LFA strips of such samples are marked with red asterisk.
Figure 29:
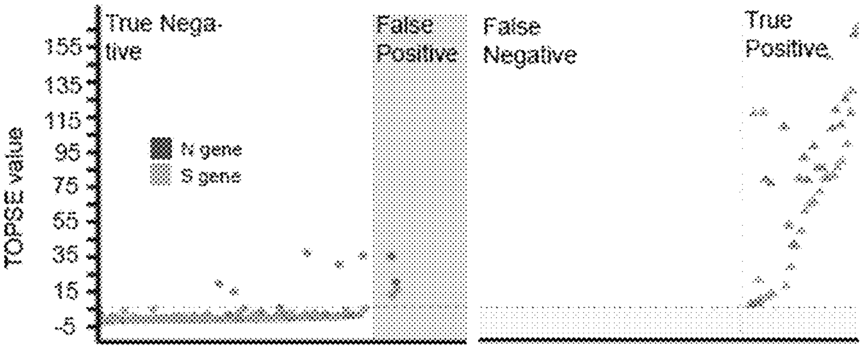
FIG. 29. Two gene FELUDA on clinical samples (x axis) showing distribution of TOPSE values (y axis). Analyzed results represented on the right.
Figure 30:
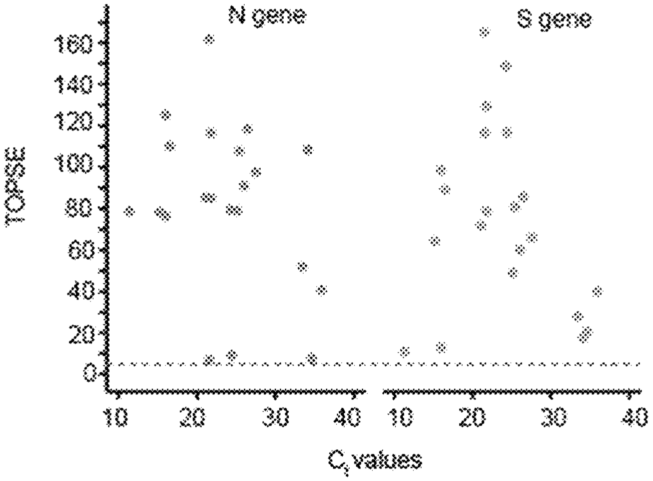
FIG. 30. Samples identified by N and S genes in 2 gene FELUDA. Ct value distribution is shown on x-axis, TOPSE values depicted on y-axis.

FELUDA using one gene (N), single pass assay was first performed on qRT-PCR confirmed 473 samples and obtained a sensitivity of 85.3% (116/136) and specificity of 96.7% (326/337) with qRT-PCR (FIG. 27). Among the samples that showed discordance between FELUDA with qRT-PCR, 8 false negative FELUDA samples and 10 false positive FELUDA samples were picked up for a repeat evaluation by FELUDA and qRT-PCR. Surprisingly, a repetition of FELUDA with double the amount of RNA yielded positive signals in 6/8 (75%) of samples and a repeat qPCR yielded positive signals in 5/10 (50%) of initially classified negative samples (FIG. 28). This underscores the error rates seen in a single run assay and has been reported elsewhere Bhoyar et al; [*BioRxiv* doi.org/10.1101/2020.08.10.242677 (2020)]. To improve FELUDA accuracy, assays for both N and S genes were combined, the starting RNA amount doubled and FELUDA was performed with 81 qRT-PCR confirmed samples. A sensitivity of 100% and a specificity of 97% was obtained and it accurately detected samples up to a high $C_t$ value of 37 showing the robustness of the assay (FIG. 29, FIG. 30).

Example 10

Home Testing Assay Based on FELUDA

Figure 25:
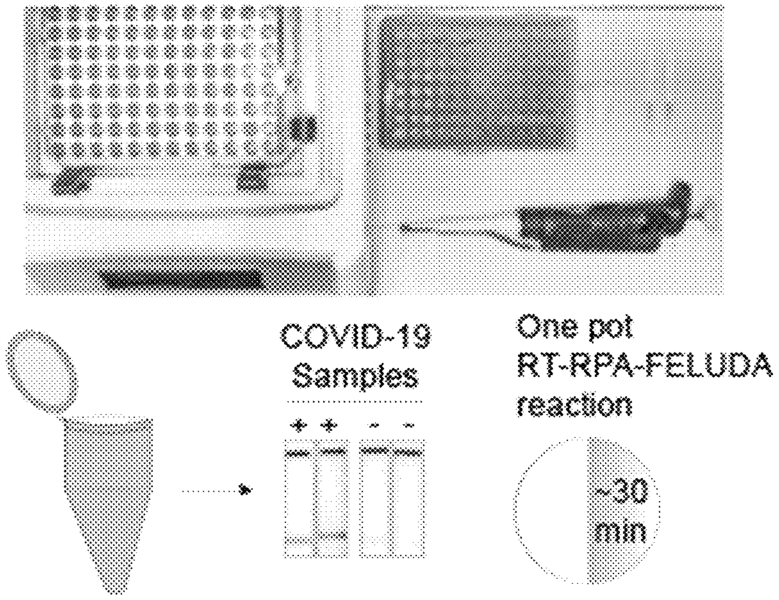
FIG. 25. One pot RT-RPA FELUDA. Top panel shows minimum requirements, bottom panel shows outcome for 2 representative samples.
Figure 26:
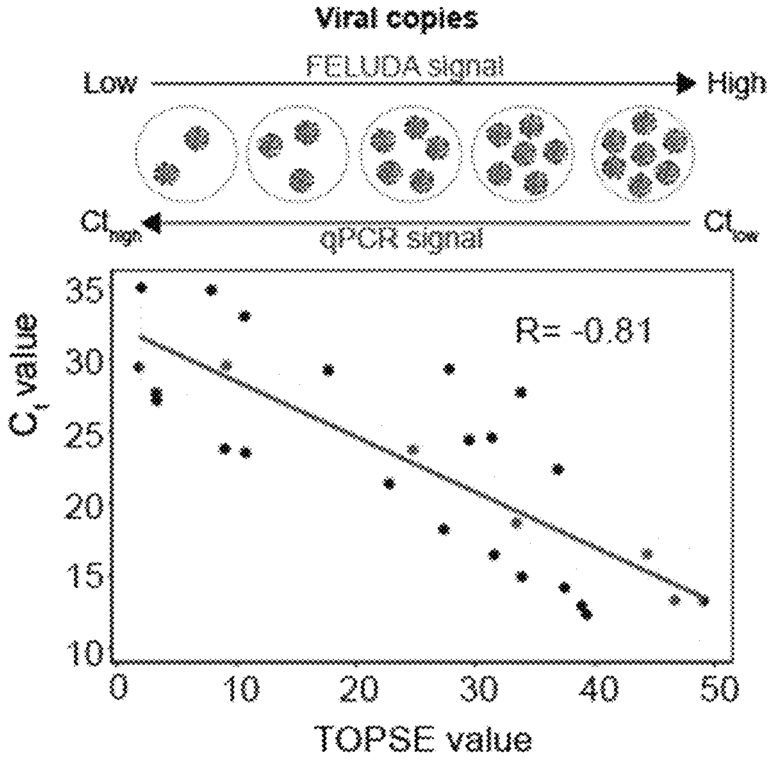
FIG. 26. FELUDA readouts are semiquantitative. Correlation between Ct values (E gene) and TOPSE values are shown (n=27).
Figure 31:
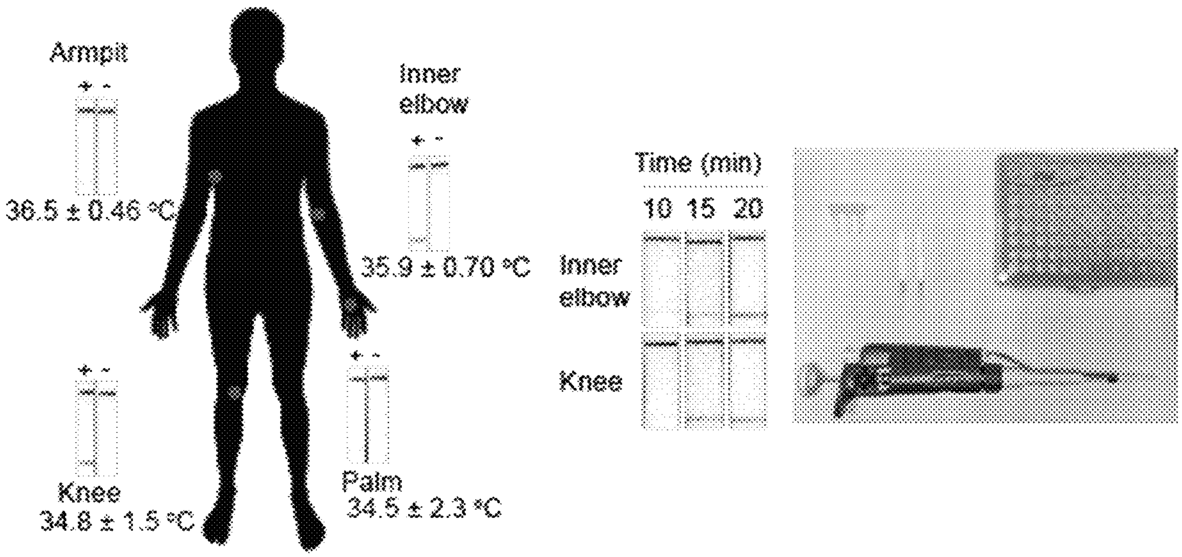
FIG. 31. On-body RT-RPA-FELUDA, left figure shows variation of temperature in different zones of the body marked in red dots and corresponding RPA-FELUDA for a synthetic RNA fragment as starting material. Center panel shows representative FELUDA using on body RT-RPA from samples incubated in two different parts of the body. Right panel represents minimum requirements for FELUDA using on-body RT-RPA.

FELUDA can be adapted to a point-of-care or home testing assay Understanding the need for more testing, especially in the wake of rising numbers and predictions of a second wave of infection [Xu et al., *Lancet.* 395, 1321-1322 (2020)], a PCR machine free version of FELUDA was implemented using Recombinase Polymerase Amplification (RPA) [Zhao et al., *Chem. Rev.* 115, 12491-12545 (2015); Lobato et al., *Trends Analyt. Chem.* 98, 19-35 (2018)] that can detect SARS-CoV2 RNA in biological samples within 30 min (FIG. 25 SEQ ID NOs 64-69). Finally, to adapt FELUDA for possible home testing in the future, an on-body 30 min RPA-FELUDA (tested using synthetic RNA fragments) was developed, thus generating an end-to-end instrumentation free testing protocol (FIG. 31).

Example 11

FELUDA can be Adapted for any SNV (Development of Bioinformatics Tool JATAYU)

Figure 32:
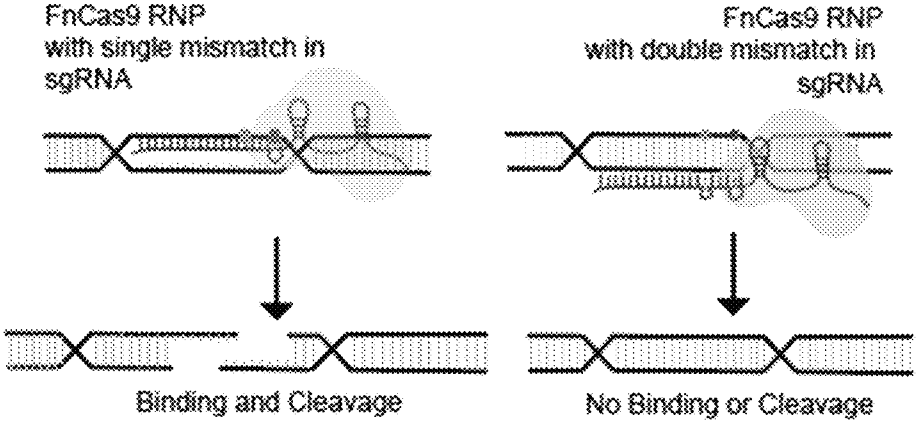
FIG. 32. Strategy for discrimination of substrates differing by single mismatch using FnCas9. Presence of 2 mismatches (marked in red and green) at defined positions on the sgRNA prevents the enzyme from binding to the target leading to different binding and cleavage outcomes.
Figure 33:
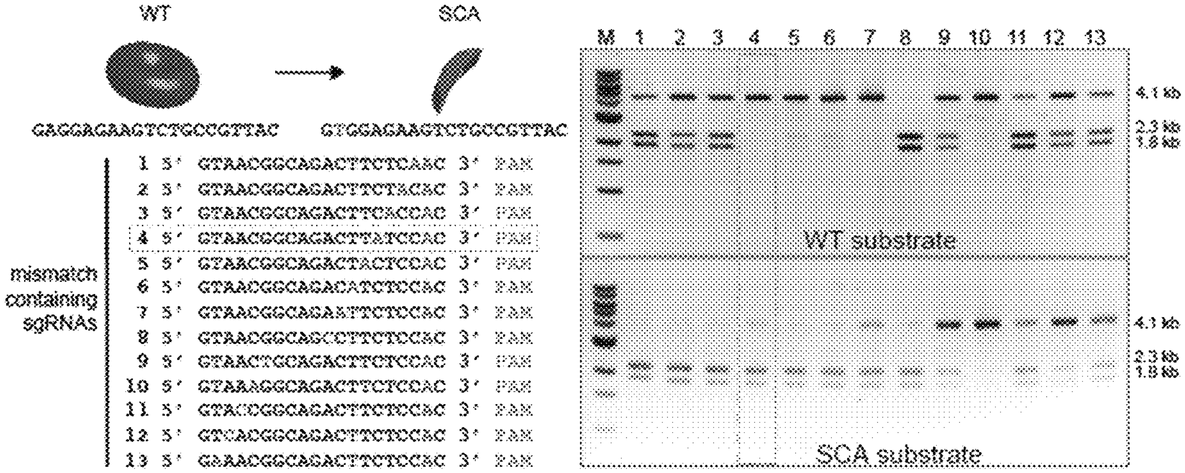
FIG. 33. Left panel shows positions of mismatches sgRNAs containing two mismatches at different positions along their lengths. Representative in-vitro cleavage outcomes on wild type (WT) or sickle cell anemia (SCA) substrates (4.1 kb) are shown on the right. Cleavage with FnCas9 produces 2 products (2.3 kb and 1.8 kb). Red dotted box denotes the sgRNA showing negligible cleavage for WT substrate and maximum cleavage for SCA substrate.
Figure 34:
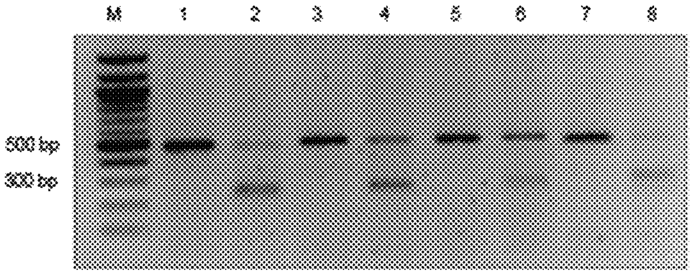
FIG. 34. FELUDA design can universally discriminate SNVs across diverse targets. Representative gel image showing synthetic targets containing either WT or pathogenic SNVs. FELUDA can distinguish between the two variants.
Figure 35:
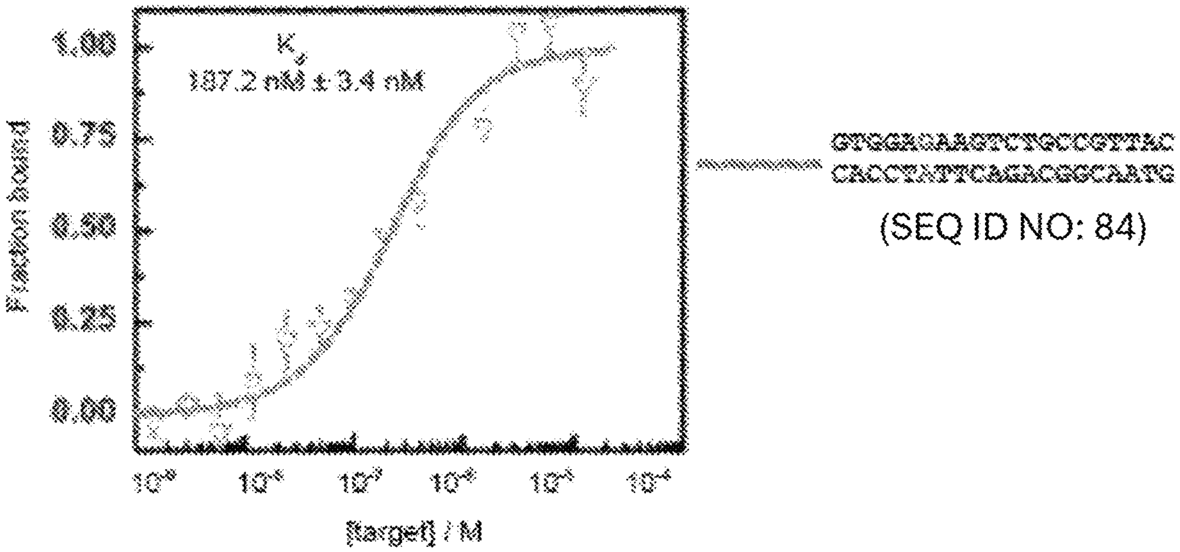
FIG. 35. Binding experiments using Microscale Thermophoresis showing interaction of FnCas9 with substrates with 1 mismatch (MM) on the left and 2 mismatches on the right. Values are expressed as fraction bound protein (y-axis) with respect to varying concentrations of purified DNA substrate (Molar units, M, x-axis). Error bars represent SEM (2 independent experiments).

To identify a SNV with high accuracy, it was first investigated if FnCas9 can be directed to cleave the wild type (WT) allele at a SNV by placing an additional MM in the sgRNA sequence specific to the SNV (FIG. 32). To test this, sickle cell anemia (SCA), a global autosomal recessive genetic disorder caused by a point mutation (GAG>GTG) was selected [Soler and Soler *Curr. Opin. Hematol.* 27 (2020) D. C. Rees, *New England J. Med.,* 1561-1573 (2017)]. By fixing the position of the SNV and walking along the entire length of the sgRNA, it was discovered that two mismatches at the PAM proximal 2nd and 6th positions completely abrogated the cleavage of the SNV target while leaving the WT target intact (FIG. 33, Targets represented by SEQ ID NOs. 19-32 using sgRNAs represented by SEQ ID NOs. 51-63). FELUDA was tested on DNA cloned from 6 SCA patients and a healthy control and obtained a clearly identifiable signature for SNV in every case (FIG. 34 SEQ ID NOs. 36-47). Importantly, the same design principle for searching and discriminating can be universally applied to other Mendelian SNVs without the need for optimization (FIG. 35). To aid users for quick design and implement FELUDA for a target SNV, a web tool JATAYU (Junction for Analysis and Target Design for Your FELUDA assay) has been developed that incorporates the above features and generates primer sequences for amplicon and sgRNA synthesis (https://jatayu.igib.res.in).

Figure 36:
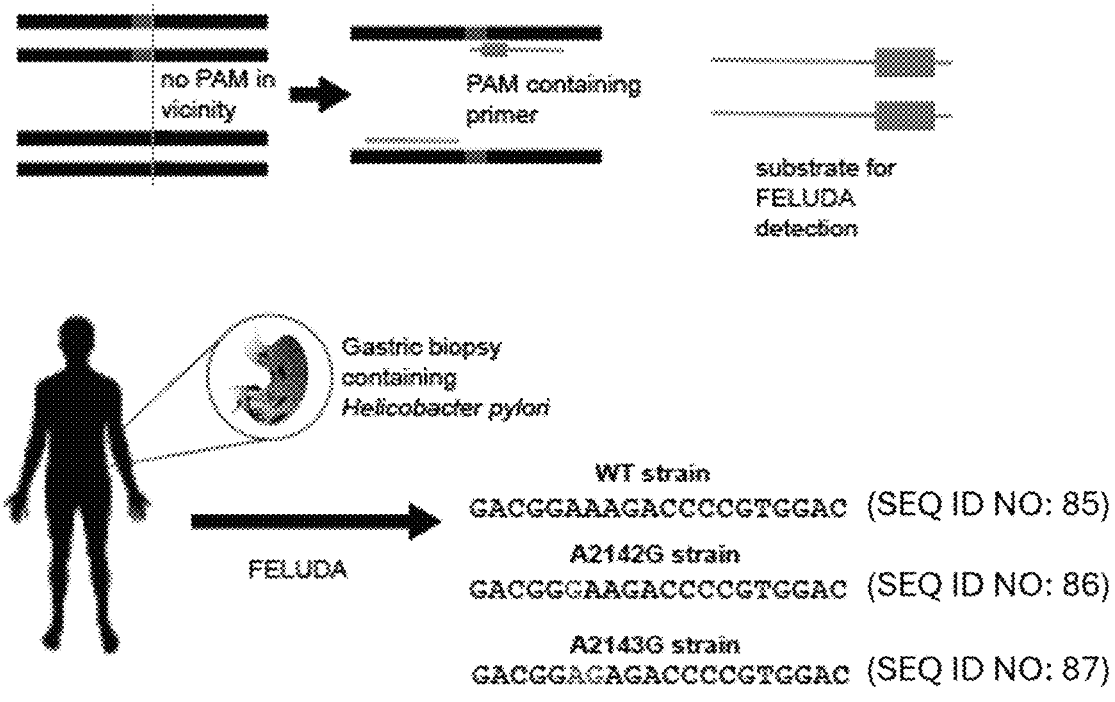
FIG. 36. Top, strategy for detection of SNVs with an in-built PAM (PAM-mer) in primer sequence. Bottom, closely related strains of H. *Pylori* showing the mutations they are associated with in red.
Figure 37:
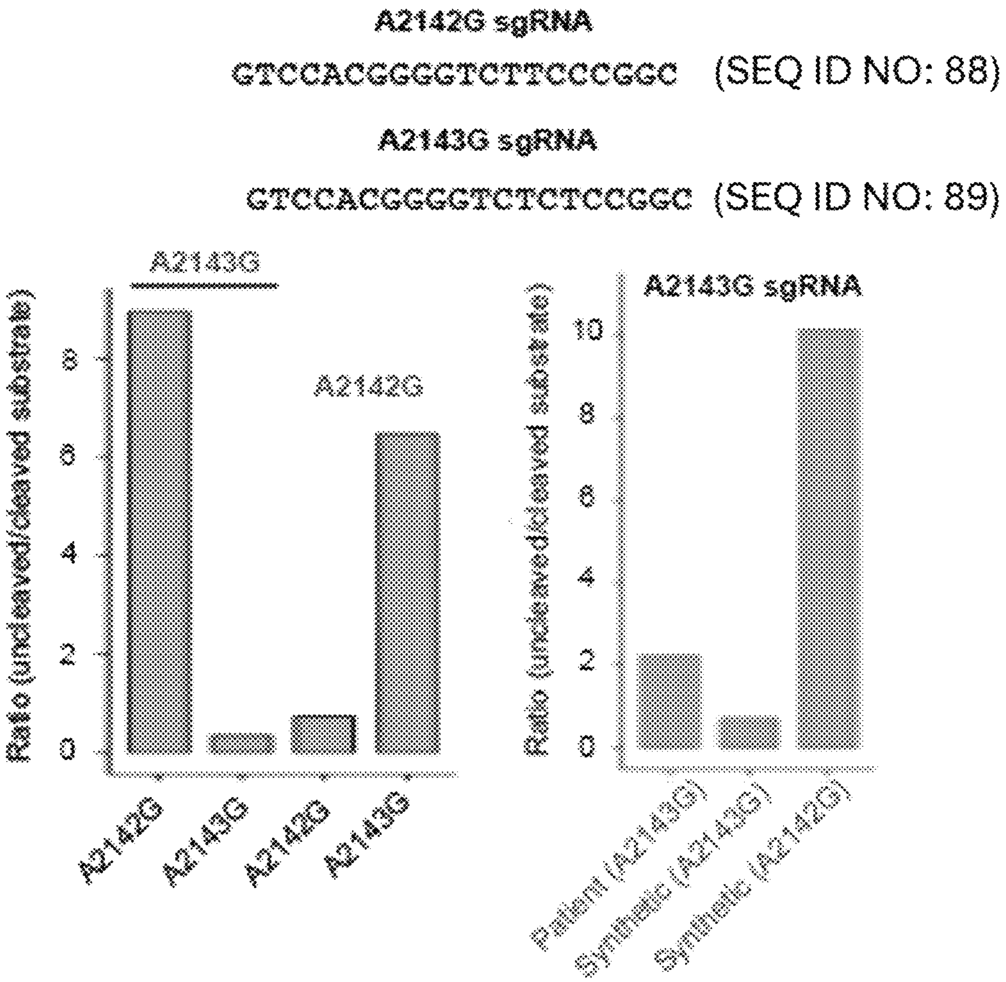
FIG. 37. Two different sgRNAs, A2142G and A2143G can produce distinct cleavage outcomes with their respective substrates (left). FELUDA based detection of A2143G genotype of H *Pylori* from gut biopsy of a patient (right). Cleavage outcomes with synthetic substrates for A2143G and A2142G are also shown.
Figure 38:
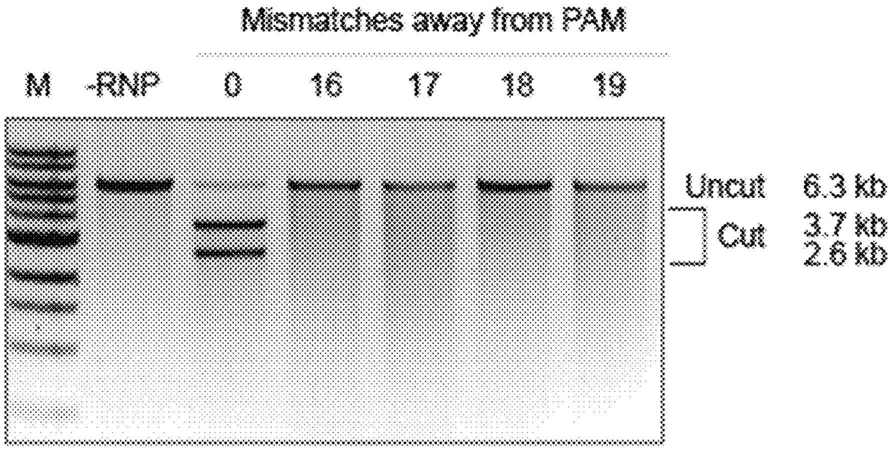
FIG. 38. Representative agarose gel showing GFP substrate cleaved with sgRNAs harboring mismatches at PAM distal 16-19th position. WT sgRNA (0) shows successful cleavage.
Figure 39:
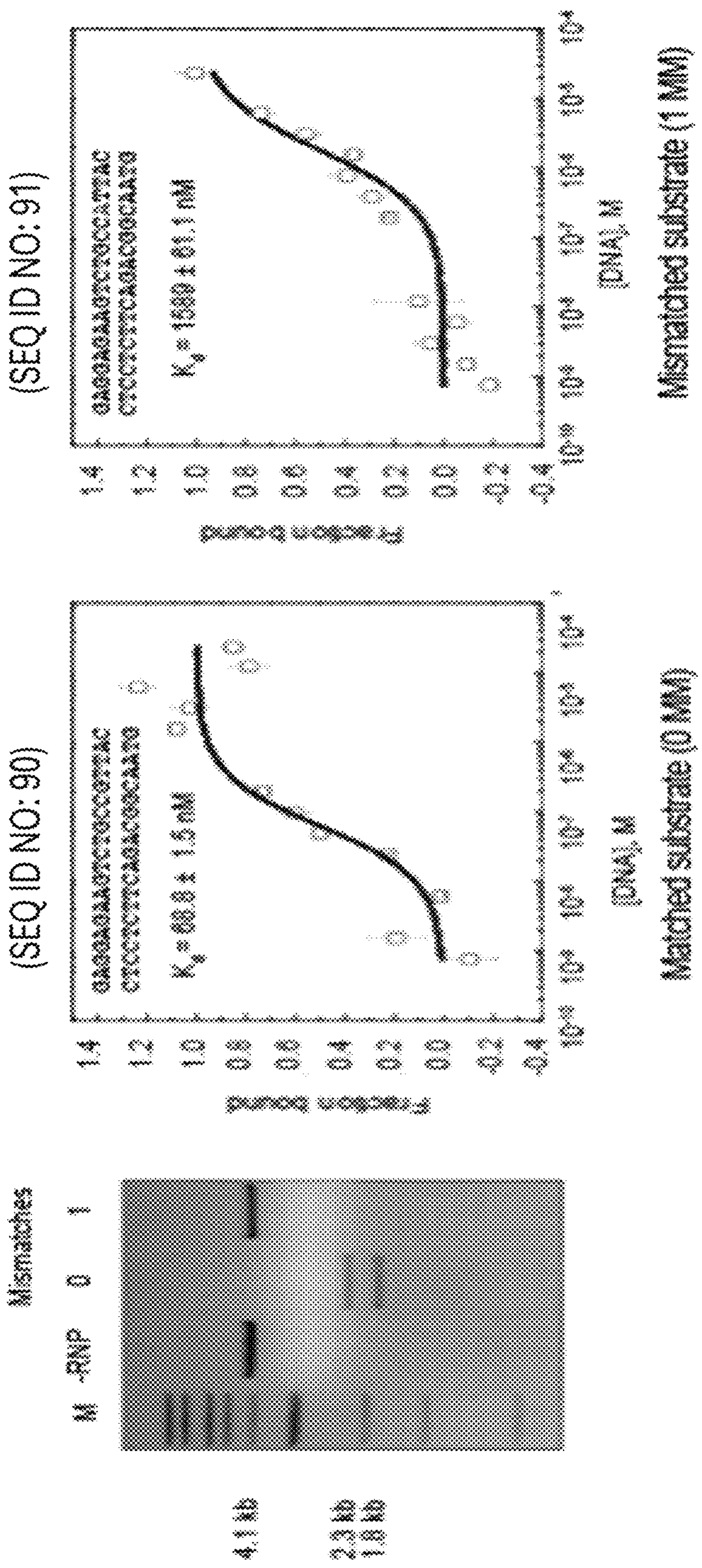
FIG. 39. Representative gel image showing no cleavage of HBB substrate with sgRNA containing 1 mismatch (16th position, PAM distal). Binding experiments using Microscale Thermophoresis showing high binding affinity with no mismatches to substrate and negligible binding affinity when 1 mismatch at 16th position (PAM distal) is present (MM, mismatches). Values are expressed as fraction bound protein (y-axis) with respect to varying concentrations of purified DNA substrate (Molar units, M, x-axis). Error bars represent SEM (2 independent experiments).
Figure 40:
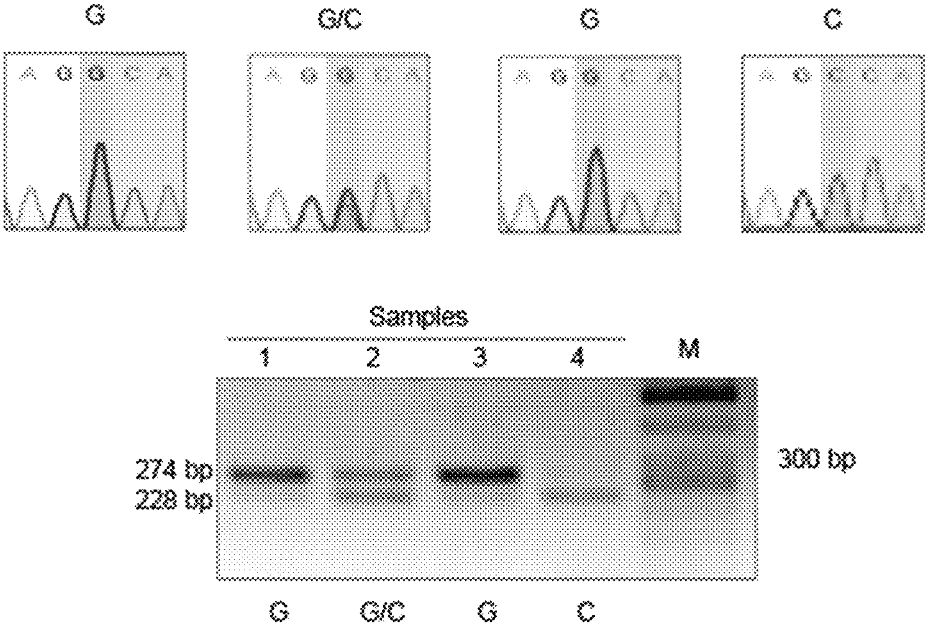
FIG. 40. Sanger sequencing confirming the allelic variants obtained from 4 individuals and FELUDA design based on placing mismatch at 16th position enables detection of variants. Negligible cleavage is seen with G variant, maximum cleavage is seen with C variant and intermediate cleavage seen with G/C variant.

Several improvements were made to FELUDA for expanding and simplifying its detection spectrum. To detect non-PAM proximal SNVs, an in-built PAM site was installed in the amplification step of FELUDA (PAMmer) and successfully validated this approach using 2 SNVs (A2142G and A2143G) present in *Helicobacter* pylon 23s rRNA gene which confers variable clarithromycin resistance in patients with gastric ulcers [Landrum et al., *Nucleic Acids Res.* 42, D980-5 (2014); Ribeiro et al., *Ann. Clin. Microbiol. Antimicrob.* 2, 11 (2003); Binkowska et al., *Front. Microbiol.* 9, 1-10 (2018)](FIGS. 36-37) Next, it was tried to reduce PAM dependency on sgRNA design further by exploring if FELUDA could be performed with a single mismatch in the sgRNA. In line with previous reports, it was found that FnCas9 shows negligible cleavage with sgRNAs containing mismatches at the PAM distal end and in particular, mismatch at PAM distal 16th base showed complete absence of cleavage or binding (FIGS. 38-39). This strategy was confirmed by targeting the SNV rs713598 (G>C) in different individuals and successfully identified their genotypes 30 (FIG. 40). It was also shown that FELUDA based detection can work robustly across a wide temperature range and up to 3 days post thawing of reaction components (at room temperature). Thus, field studies using FELUDA can be conducted in diverse climatic conditions and reaction components can be successfully used following cold chain transportation (FIG. 41)

COMPARATIVE EXAMPLE

To show the higher efficiency of the FnCas9 ribonucleoprotein complex of the present invention comprising a cas9 protein from *Francisella novicida* and a single single guide RNA (FnCas9:sgRNA) over the known ribonucleoprotein complex in the art (Sp:Cas9 sgRNA), comparative tests were done.

The nucleotide sequence corresponding to the sgRNA for a representative locus for targeting by SpCas9 and its derivatives from Ran et al, (Nat Protoc. 8, 2281-2308 (2013)

(SEQ ID NO: 74)

5'

NNNNNNNNNNNNNNNNNNNNAGGGTTTTAGAGCTAGAAATAGCAAGTTAA

AATAAGGCTAGTCCGTTATCAACTTGAAAAAGTGGCACCGAGTCGGTGCTT

TTTTT 3' where N stretch corresponds to 20 nucleotides of target sequence of the form (SEQ ID NO: 75)

GTAACGGCAGACTTCTCCTCAGGGTTTTAGAGCTAGAAATAGCAAGTTAAA
ATAAGGCTAGTCCGTTATCAACTTGAAAAAGTGGCACCGAGTCGGTGCTTT
TTTT

The sgRNA sequence for Hemoglobin locus for FnCas9 from Hirano et al. [Cell, 164(5), 950-961 (2016)]:

(SEQ ID NO: 76)

5'
NNNNNNNNNNNNNNNNNNNNAGGGTTTCAGTTGCGCCGAAAGGCGCTCTG
TAATCATTTAAAAGTATTTTGAACGGACCTCTGTTTGACACGTCTG 3' where N stretch corresponds to 20 nucleotides of target sequence, of the form (SEQ ID NO: 77)
5'
GTAACGGCAGACTTCTCCTCAGGGTTTCAGTTGCGCCGAAAGGCGCTCTGT
AATCATTTAAAAGTATTTTGAACGGACCTCTGTTTGACACGTCTG 3'

These sgRNAs show complete binding to the target. In order to efficiently differentiate between 2 targets that are different by 1 mismatch, in the present application, sgRNA was designed in two strategies for FnCas9. The comparative test show that the same strategy of design cannot discriminate between substrates using SpCas9 used in the prior art.

The First Strategy

The first strategy of mismatch discrimination comprises of 2 mismatches in the FnCas9 sgRNA, at PAM proximal 2nd and 6th position. This was achieved by systematically changing the position of mismatches in the sgRNA in duplex fashion till a completely opposite cleavage outcome was achieved as disclosed in FIGS. 32 and 33. FIG. 32 shows a schematic showing the differences in outcome when FnCas9 encounters a target with 1 mismatch vs 2 mismatch. FIG. 33 shows the positions with 2 mismatches tested on 2 substrates (corresponding to Wildtype, WT Hemoglobin sequence and SCA, Sickle Cell Anemia Hemoglobin sequence). Mismatch positions with respect to PAM (green) are shown in red and the red dotted box shows the most optimal region for placing mismatches that are able to distinguish the two substrates.

The representative sequence of sgRNA for disease detection as provided in the present application (2 mismatches): Mismatches in 2nd and 6th position PAM (AGG) proximal (SEQ ID NO: 54)
5'
GTAACGGCAGACTTATCCACAGGGTTTCAGTTGCGCCGAAAGGCGCTCTGT
AATCATTTAAAAGTATTTTGAACGGACCTCTGTTTGACACGTCTG 3'

To compare between the efficiency of SNP dissection between this design strategy of the present invention and that of known Cas9 RNP (SpCas9) or its high fidelity derivative (SpCas9-HF1), corresponding sgRNAs with mismatches at identical positions were designed for SpCas9 and SpCas9-HF.

Representative sequence of sgRNA for SpCas9 and SpCas9-HF1 using identical strategy (2 mismatches): Mismatches in 2nd and 6th position PAM (AGG) proximal (SEQ ID NO: 78)
5'
GTAACGGCAGACTTATCCACAGGGTTTTAGAGCTAGAAATAGCAAGTTAAA
ATAAGGCTAGTCCGTTATCAACTTGAAAAAGTGGCACCGAGTCGGTGC
3'

Figure 43:
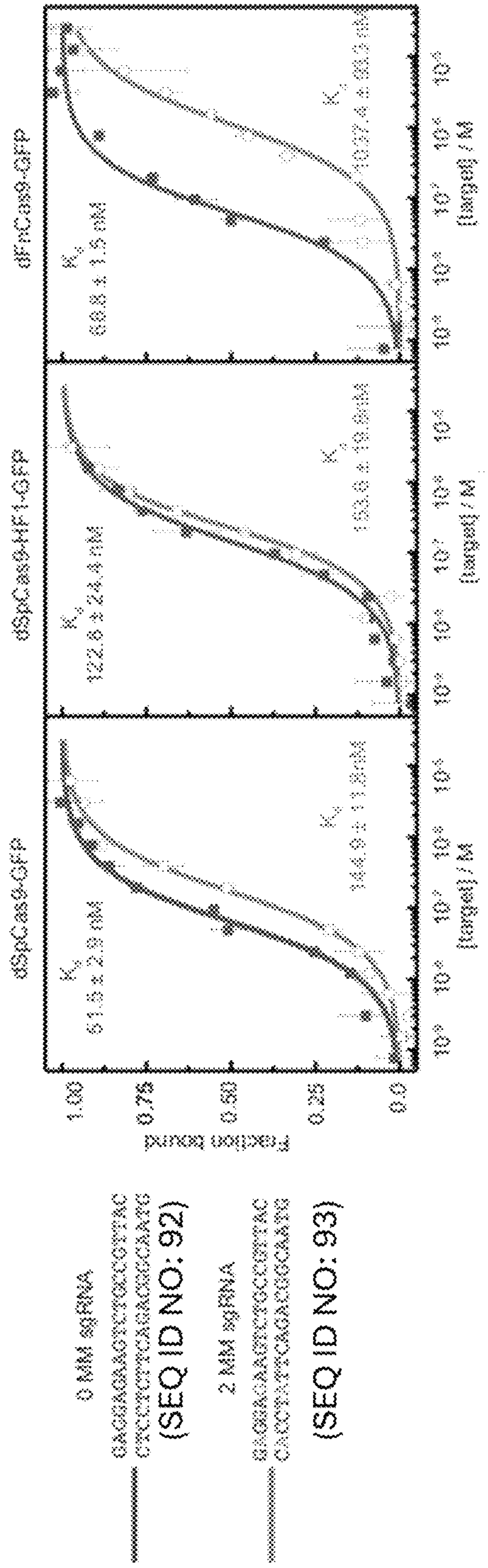
FIG. 43. Binding affinity experiments using Microscale Thermophoresis showing interaction of dSpCas9-GFP, dSpCas9-HF1-GFP and dFnCas9-GFP with substrates with 0 (■) or 2 (○) mismatch (MM). Values are expressed as fraction bound protein (y-axis) with respect to varying concentrations of purified DNA substrate (Molar units, M, x-axis). Error bars represent SEM (2 independent experiments).

FIG. 43 shows the binding affinity experiments using Microscale Thermophoresis showing interaction of dSpCas9-GFP, dSpCas9-HF1-GFP and dFnCas9-GFP with substrates with 0 (■) or 2 (○) mismatch (MM). Values are expressed as fraction bound protein (y-axis) with respect to varying concentrations of purified DNA substrate (Molar units, M, x-axis). Error bars represent SEM (2 independent experiments). It was observed that only in the case of FnCas9, the binding with substrate was lost (very high Kd of 1037.4+/−93.3 nM signifies negligible binding). In case of both SpCas9 and SpCas9-HF1 the kd of mismatched targets are 144.9+/−11.8 nM and 153.6+/−19.8 nM respectively showing very strong binding. All proteins are tagged with GFP to enable fluorescence measurement of binding affinities. These results indicate that the sgRNA design parameters for distinguishing mismatches are specific to FnCas9 and cannot be demonstrated by other proteins reported in prior art.

Taken together, these experiments show that the design principle of the present invention (2 mismatches at PAM proximal 2nd and 6th positions) applies only to FnCas9 and its sgRNA and not for SpCas9 or even its high fidelity derivatives mentioned in literature [Kleinstiver et al. Nature 529, 490-495(2016)].

The Second Strategy

The second strategy of mismatch discrimination comprises of a single nucleotide position mismatch at the PAM distal end which can also lead to efficient discrimination between 2 substrates as shown below.

FIG. 38 shows cleavage outcomes on a DNA substrate with 1 bp mismatch at PAM distal 16, 17, 18 and 19 positions (sequences provided below). It can be observed that a nucleotide mismatch at each of these positions can render the FnCas9:RNP complex incapable of cleaving a target. Thus a mismatch at any of these positions can be used to distinguish between 2 substrates different by 1 nucleotide. FIG. 39 shows cleavage outcomes on a DNA substrate with 1 bp mismatch at PAM distal 16th position. As it can be observed, a single nucleotide mismatch at the 16th position is able to render the FnCas9:RNP complex incapable of cleaving the same target. Further, the binding affinity experiments using Microscale Thermophoresis show high binding affinity with no mismatches to the substrate and negligible binding affinity when one mismatch at 16th position (PAM distal) is present (MM, mismatches). Values are expressed as fraction bound protein (y-axis) with respect to varying concentrations of purified DNA substrate (Molar units, M, x-axis). Error bars represent SEM (2 independent experiments). Using FnCas9 and a single mismatch (16th position, PAM distal) in the sgRNA, the binding with substrate was lost (very high Kd of 1589+/−61.1 nM signifies negligible binding). The zero (0) mismatch values are shown in the figure.

Taken together, these experiments show that the design principle of the present application i.e. 1 mismatches at PAM distal 16th position can be used to distinguish two substrates different by 1 nucleotide.

Generic FnCas9 sgRNA for disease detection mentioned in present application (1 mismatch): position 16 bp away from PAM denoted by X (SEQ ID NO: 80)
5'
NNNNXNNNNNNNNNNNNNNNAGGGTTTCAGTTGCGCCGAAAGGCGCTCTG
TAATCATTTAAAAGTATTTTGAACGGACCTCTGTTTGACACGTCTG'
3'

Generic FnCas9 sgRNA for disease detection mentioned in present application (1 mismatch): position 17 bp away from PAM denoted by X (SEQ ID NO: 80)
5'
NNNXNNNNNNNNNNNNNNNNNAGGGTTTCAGTTGCGCCGAAAGGCGCTCTG
TAATCATTTAAAAGTATTTTGAACGGACCTCTGTTTGACACGTCTG'
3'

Generic FnCas9 sgRNA for disease detection mentioned in present application (1 mismatch): position 18 bp away from PAM denoted by X (SEQ ID NO: 80)
5'
NNNXNNNNNNNNNNNNNNNNNAGGGTTTCAGTTGCGCCGAAAGGCGCTCTG
TAATCATTTAAAAGTATTTTGAACGGACCTCTGTTTGACACGTCTG'
3'

Generic FnCas9 sgRNA for disease detection mentioned in present application (1 mismatch): position 19 bp away from PAM denoted by X (SEQ ID NO: 80)
5'
NNNXNNNNNNNNNNNNNNNNNAGGGTTTCAGTTGCGCCGAAAGGCGCTCTG
TAATCATTTAAAAGTATTTTGAACGGACCTCTGTTTGACACGTCTG'
3'

In order to make the discrimination amenable to point of care diagnostic kits such as fluorescence readout or paper strip readout as described in the present invention, the sgRNA was further modified to enable binding based discrimination either by fluorescence or on a paper strip. FIG. 16 shows that adaptation of chimeric gRNA for FELUDA. Cleavage outcomes with different lengths of overlap between crRNA and tracrRNA are shown. 19nt overlap performs most optimally when used in an in vitro cleavage reaction.

To enable fluorescent tagging of the sgRNA, a chimeric sgRNA in two parts with 19 nucleotide overlap is designed (SEQ ID NO: 36 and SEQ ID NO: 37 to be annealed to make full length sgRNA). This chimeric design performed catalytic function similar to that of a full length sgRNA showing no loss of activity due to the split-sgRNA synthesis and also without any loss of specificity for 1 mismatch discrimination. FIG. 42 sows gel showing cleavage outcomes for SARS CoV2 on-target and 1 mismatch off-target for either the single single guide RNA or the chimeric (dual) single guide RNA using FnCas9 RNP. No loss of activity or specificity is seen. A different locus is shown as control.

Figure 44:
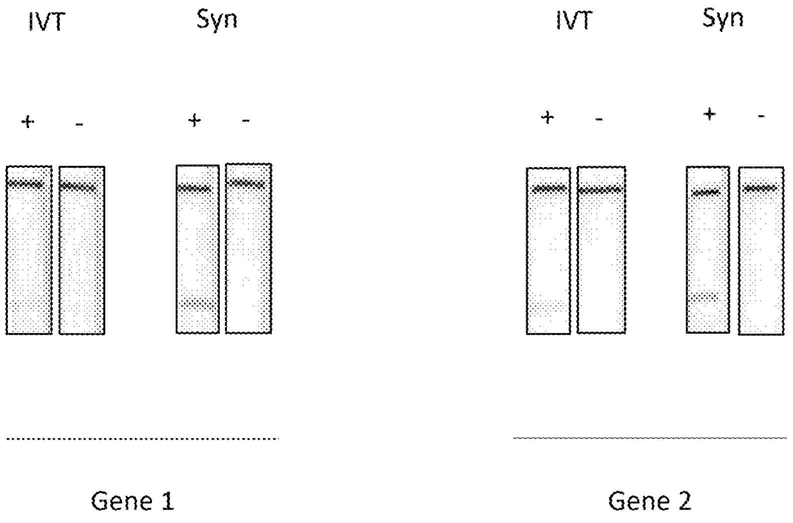
FIG. 44. Representative images showing differences between unmodified (IVT, in vitro transcribed) vs Phosphorothioate modified (syn, synthetic) gRNA (Genes 1 and 2) [stored at −20 and after undergoing multiple freeze thaw processes].

The design was further modified to suit the possibility of detecting polynucleotides on a paper strip using 3' FAM labelled Part 2 of the gRNA. Additionally, both parts were modified with Phosphorothioate backbone (SEQ ID no. 72, 73). These modifications resulted in more robust, accurate and sensitive detection of SARS CoV2 in patient samples. FIG. 15 shows the outline of lateral flow assay using FELUDA showing positions of control and test bands. FIG. 44 shows the representative images showing differences between unmodified (IVT, in vitro transcribed) vs Phosphorothioate modified (syn, synthetic) gRNA (Genes 1 and 2) [stored at −20 and after undergoing multiple freeze thaw processes].

Advantages of the Present Invention

The main advantages of the present invention are as follows.

1.) The kit of the present invention comprising the CAS9 CRISPR effector system can be used to identify any mutation in an amplified polynucleotide and produce a read out that can be used for genotyping the target with respect to that single nucleotide variant without the need for sequencing.
2.) The kit of the present invention can be used for rapid, point of care diagnostic for COVID-19 presence in a biological sample.
3.) The time taken for isothermal amplification and enzymatic cleavage is extremely short, leading to very quick detection. Results can be obtained within a couple of hours which allows the initiation of quick prophylactic measures and community transfer steps.
4.) The kit and method of the present invention can be used for multiple targets where the only variable component of the system is the crRNA harboring mismatches to the target. By careful design, the minimum additional binding sequence for CAS9-RNP to the target (namely, the PAM sequence) can be synthetically added to the primers for target amplification, which expands the detection ability to any SNV.
5.) The kit of the present invention is highly specific towards the results with very few false positive or false negative results obtained.
6.) By combining different sgRNA sequences in a systematic manner, the kit of the present invention allows detection of both heterozygous as well as homozygous single nucleotide variants (SNVs). Thus, both carriers as well as diseased individuals can be genotyped for recessive disorders in addition to genotyping homozygous dominant individuals.
7.) As the reaction components of the kit can be assembled in very small quantities, the cost of running the reaction is reduced.
8.) The kit and method of the present invention requires minimum time for sample preparation and hence, can be adapted to low cost, highly efficient, point of care assays that can benefit patients in remote areas without the access to sequencing platforms.

We claim:

1. A kit for detecting a target polynucleotide, the kit comprising:

a. reverse and forward primers;

b. dNTPS;

c. a PCR buffer;

d. a DNA polymerase;

e. a FnCas9 protein having SEQ ID NO. 2;

f. a single guide RNA; and g. a CRISPR-CAS9 reaction buffer.

2. The kit of claim 1, wherein the single guide RNA has a sequence selected from the group consisting of SEQ ID NOS.: 32, 33, 36, 39, 42, 45, 48, 51-64, 67, 76, 77, 79, and 80.

3. The kit of claim 1, wherein the primers are selected from sequences having SEQ ID NOS.: 37, 38, 40, 41, 43, 44, 46, 47, 49, 50, 65, 66, 68, or 69.

4. The kit of claim 1, wherein the PCR buffer comprises Recombinase Polymerase Amplification (RPA) Rehydration buffer and Magnesium Acetate.

5. The kit of claim 1, wherein the kit further comprises reverse transcriptase.

6. The kit of claim 1, wherein the CRISPR-CAS9 reaction buffer comprises one or more of HEPES, KCl, DTT, glycerol and $MgCl_2$.

7. The kit of claim 1, wherein the primers are labelled with biotin.

8. The kit of claim 1, wherein the FnCas9 protein is complexed with a single guide RNA and labelled with a chemical.

9. The kit of claim 1, wherein the FnCas9 protein is isolated from *Francisella novicida.*

10. The kit of claim 1, wherein the FnCas9 protein is coupled with a fluorophore tag and has SEQ ID NO: 3.

11. The kit of claim 1, wherein the kit further comprises a reaction tube, a dipstick buffer and a paper strip.

12. The kit of claim 11, wherein the dipstick buffer is a Tris buffered saline.

13. The kit of claim 11, wherein the paper strip is made of a nitrocellulose membrane coated with a biotin-ligand and polyclonal (goat) digoxigenin antibody or polyclonal (rabbit) anti-FITC antibody in gold conjugate.

14. A FnCas9 ribonucleoprotein complex comprising a Cas9 protein from *Francisella novicida* having the amino acid sequence as set forth in SEQ ID NO. 2, and a single guide RNA having SEQ ID NO. 79.

15. The FnCas9 ribonucleoprotein complex of claim 14, wherein the single guide RNA or its corresponding sequence is selected from the group consisting of SEQ ID NOS.: 5, 6, 8, 9, 11, 12, 14, 15, 17, 18, 19-36, 39, 42, 45, 48, 76, 77, 79, 80.

16. The FnCas9 ribonucleoprotein complex of claim 14, wherein the corresponding DNA targeting region in SARS-CoV2 has a sequence as set forth in SEQ ID NOS.: 64, 67.

* * * * *